US007267819B2

(12) United States Patent
Ferrara et al.

(10) Patent No.: US 7,267,819 B2
(45) Date of Patent: Sep. 11, 2007

(54) COMPOSITION COMPRISING AND METHOD OF USING ANGIOPOIETIN-LIKE PROTEIN 3 ANGPTL3

(75) Inventors: Napoleone Ferrara, San Francisco, CA (US); Hans-Peter Gerber, San Francisco, CA (US); Joe Kowalski, Redwood City, CA (US); Maria Teresa Pisabarro, Dresden (DE); Daniel Eric Sherman, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 120 days.

(21) Appl. No.: 10/298,461

(22) Filed: Nov. 15, 2002

(65) Prior Publication Data

US 2003/0215451 A1 Nov. 20, 2003

Related U.S. Application Data

(60) Provisional application No. 60/332,429, filed on Nov. 16, 2001.

(51) Int. Cl.
*A61K 39/395* (2006.01)
*A61K 39/00* (2006.01)

(52) U.S. Cl. .............................. 424/130.1; 424/133.1; 424/135.1; 424/139.1; 424/141.1; 424/142.1; 424/152.1; 424/172.1

(58) Field of Classification Search .................. 514/44
See application file for complete search history.

(56) References Cited

U.S. PATENT DOCUMENTS

| 5,972,338 A | * | 10/1999 | Godowski et al. ....... 424/185.1 |
| 6,074,873 A | * | 6/2000 | Fong et al. ................. 435/325 |
| 6,596,850 B1 | * | 7/2003 | Huse ....................... 530/387.3 |
| 2003/0077809 A1 | * | 4/2003 | Ruben et al. ............... 435/226 |

FOREIGN PATENT DOCUMENTS

| WO | WO99/15654 | 4/1999 |
| WO | WO99/55869 | * 11/1999 |
| WO | WO99/67382 | 12/1999 |
| WO | WO 99/67382 | 12/1999 |
| WO | WO 00/53757 | 9/2000 |

OTHER PUBLICATIONS

Kiang et al., Pharmacol Ther. 1998, vol. 80(2): 183-201.*
Brooks et al., Cell 1994, vol. 79(7): pp. 1157-1164.*
Sun et al., J Cancer Res Clin Oncol. 1999, vol. 125(7): pp. 419-426.*
Philip S., Cancer Pract. 2000, vol. 8(3): pp. 148-150.*
Medina et al. 2004. Hepatology 39:1185-1195.*
Andersen et al. 1997. Electrophoresis 18:533-537.*
Camenisch G et al. 2002. JBC 277:17281-17290.*
Goodman and Gilman, The Pharmacological Basis of Therapeutics. 10th edition, McGraw-Hill, 2001, p. 3-29.*
Charnow et al. 1996 Trends Biotech 14:52-60.*
Carter P. 2001. J Immunol Methods 248:7-15.*
Camenisch Gieri et al., 2002, *Journal of Biological Chemistry*, 277(19):17281-17290 "ANGPTL3 Stimulates Endothelial Cell Adhesion and Migration via Integrin $a_v\beta_3$ and Induces Blood Vessel Formation in Vivo".
Conklin D et al., 1999, *Genomics*, 62(3):477-482 "Identification of a Mammalian Angiopoietin-Related Protein Expressed Specifically in Liver".
Yokoyama Kenji et al., 2000, *Journal of Biological Chemistry*, 275(22):16891-16898 "Identification of Amino Acid Sequences in Fibrinogen γ-Chain And Tenascin C C-terminal Domains Critical for Binding to Integrin $a_v\beta_3$".
Supplementary Partial European Search Report dated Jun. 29, 2005, for European Patent Application No. EP 02 78 2310.
Camenisch, et al., 2002, *The Journal of Biological Chemistry*, 277(19):17281-17290 "ANGPTL3 Stimulates Endothelial Cell Adhesion and Migration via Integrin $\alpha_v\beta_3$ and Induces Blood Vessel Formation in Vivo".
Carron et al., 1998, *Cancer Research*, 58:1930-1935 "A Peptidomimetic Antagonist of the Integrin $\alpha_v\beta_3$ Inhibits Leydig Cell Tumor Growth and the Development of Hypercalcemia of Malignancy".
Conklin et al., 1999, *Genomics*, Academic Press, San Diego, U.S., 62(3):477-482 "Identification of a Mammalian Angiopoietin-Related Protein Expressed Sepcifically in Liver".
Friedlander et al., 1996, *Proc. Natl. Acad. Sci. USA*, 93:9764-9769 "Involvement of integrins $\alpha_v\beta_3$ and $\alpha_v\beta_5$ in ocular neovascular diseases".
Kerr et al., 1999, *Anticancer Research*, 19:959-968 "Novel Small Molecule αv Integrin Antagonists: Comparative Anti-Cancer Efficacy with Known Angiogenesis Inhibitors".
Kumar et al., 2001, *Cancer Research*, 61:2232-2238 "Inhibition of Angiogenesis and Tumor Growth by SCH221153, a Duial $\alpha_v\beta_3$ and $\alpha_v\beta_5$ Integrin Receptor Antagonist".
Lark et al., 2001, *Journal of Bone and Mineral Research*, 16(2):319-325 "Antagonism of the Osteoclast Vitronectin Receptor with an Orally Active Nonpeptide Inhibitor Prevents Cancellous Bone Loss in the Ovariectomized Rat".
Xiong et al., 2001, *Science*, 294:339-345 "Crystal Structure of the Extracellular Segment of Integrin αVβ3".
Xiong et al., 2002, *Science*, 296:151-155 Crystal Strucutre of the Extracellular Segment of Integrin αVβ3 in Complex with an Arg-Gly-Asp Ligand.
Yokoyama et al., 2000, *Journal of Biological Chemistry*, 275(22):16891-16898 "Identification of amino acid sequences in fibrinogen gamma-chain and tenascin C C-terminal domains critical for binding to integrin alphavbeta3".
Supplementary Partial European Search Report dated Jun. 29, 2005 and mailed Dec. 19, 2005.

* cited by examiner

*Primary Examiner*—Lorraine Spector
*Assistant Examiner*—Shulamith H. Shafer
(74) *Attorney, Agent, or Firm*—Merchant & Gould P.C.

(57) ABSTRACT

The present invention is directed to methods and means for making and using Angptl3 polypeptides. The invention specifically concerns the use of Angptl3 polypeptides in inducing liver regeneration and angiogenesis. Further methods include the use of Angptl3 polypeptides in the diagnosis and treatment of liver disease. Also provided herein are antibodies which bind to the polypeptides of the present invention.

17 Claims, 27 Drawing Sheets

FIGURE 1

```
GCGGACGCGT GGGTGAAATT GAAAATCAAG ATAAAAATGT TCACAATTAA   50
GCTCCTTCTT TTTATTGTTC CTCTAGTTAT TTCCTCCAGA ATTGATCAAG  100
ACAATTCATC ATTTGATTCT CTATCTCCAG AGCCAAAATC AAGATTTGCT  150
ATGTTAGACG ATGTAAAAAT TTTAGCCAAT GGCCTCCTTC AGTTGGGACA  200
TGGTCTTAAA GACTTTGTCC ATAAGACGAA GGGCCAAATT AATGACATAT  250
TTCAAAAACT CAACATATTT GATCAGTCTT TTTATGATCT ATCGCTGCAA  300
ACCAGTGAAA TCAAAGAAGA AGAAAAGGAA CTGAGAAGAA CTACATATAA  350
ACTACAAGTC AAAAATGAAG AGGTAAAGAA TATGTCACTT GAACTCAACT  400
CAAAACTTGA AAGCCTCCTA GAAGAAAAAA TTCTACTTCA ACAAAAGTG  450
AAATATTTAG AAGAGCAACT AACTAACTTA ATTCAAAATC AACCTGAAAC  500
TCCAGAACAC CCAGAAGTAA CTTCACTTAA AACTTTTGTA GAAAACAAG   550
ATAATAGCAT CAAAGACCTT CTCCAGACCG TGGAAGACCA ATATAAACAA  600
TTAAACCAAC AGCATAGTCA AATAAAGAA ATAGAAAATC AGCTCAGAAG   650
GACTAGTATT CAAGAACCCA CAGAAATTTC TCTATCTTCC AAGCCAAGAG  700
CACCAAGAAC TACTCCCTTT CTTCAGTTGA ATGAAATAAG AAATGTAAAA  750
CATGATGGCA TTCCTGCTGA ATGTACCACC ATTTATAACA GAGGTGAACA  800
TACAAGTGGC ATGTATGCCA TCAGACCCAG CAACTCTCAA GTTTTCATG   850
TCTACTGTGA TGTTATATCA GGTAGTCCAT GGACATTAAT TCAACATCGA  900
ATAGATGGAT CACAAAACTT CAATGAAACG TGGGAGAACT ACAAATATGG  950
TTTTGGGAGG CTTGATGGAG AATTTTGGTT GGGCCTAGAG AAGATATACT 1000
CCATAGTGAA GCAATCTAAT TATGTTTTAC GAATTGAGTT GGAAGACTGG 1050
AAAGACAACA AACATTATAT TGAATATTCT TTTTACTTGG GAAATCACGA 1100
AACCAACTAT ACGCTACATC TAGTTGCGAT TACTGGCAAT GTCCCCAATG 1150
CAATCCCGGA AAACAAAGAT TTGGTGTTTT CTACTTGGGA TCACAAAGCA 1200
AAAGGACACT TCAACTGTCC AGAGGGTTAT TCAGGAGGCT GGTGGTGGCA 1250
TGATGAGTGT GGAGAAAACA ACCTAAATGG TAAATATAAC AAACCAAGAG 1300
CAAAATCTAA GCCAGAGAGG AGAAGAGGAT TATCTTGGAA GTCTCAAAAT 1350
GGAAGGTTAT ACTCTATAAA ATCAACCAAA ATGTTGATCC ATCCAACAGA 1400
TTCAGAAAGC TTTGAATGAA CTGAGGCAAT TTAAAGGCAT ATTTAACCAT 1450
TAACTCATTC CAAGTTAATG TGGTCTAATA ATCTGGTATA AATCCTTAAG 1500
AGAAAGCTTG AGAAATAGAT TTTTTTTATC TTAAAGTCAC TGTCTATTTA 1550
AGATTAAACA TACAATCACA TAACCTTAAA GAATACCGTT TACATTTCTC 1600
AATCAAAATT CTTATAATAC TATTTGTTTT AAATTTTGTG ATGTGGGAAT 1650
CAATTTTAGA TGGTCACAAT CTAGATTATA ATCAATAGGT GAACTTATTA 1700
AATAACTTTT CTAAATAAAA AATTTAGAGA CTTTTATTTT AAAAGGCATC 1750
ATATGAGCTA ATATCACAAC TTTCCCAGTT TAAAAAACTA GTACTCTTGT 1800
TAAAACTCTA AACTTGACTA AATACAGAGG ACTGGTAATT GTACAGTTCT 1850
TAAATGTTGT AGTATTAATT TCAAAACTAA AAATCGTCAG CACAGAGTAT 1900
GTGTAAAAAT CTGTAATACA AATTTTTAAA CTGATGCTTC ATTTTGCTAC 1950
AAAATAATTT GGAGTAAATG TTTGATATGA TTTATTTATG AAACCTAATG 2000
AAGCAGAATT AAATACTGTA TTAAAATAAG TTCGCTGTCT TT          2042
```

FIGURE 2A

| | | | | | | | | | | | | | | |
|---|---|---|---|---|---|---|---|---|---|---|---|---|---|---|
| MET | PHE | THR | ILE | LYS | LEU | LEU | LEU | PHE | ILE | VAL | PRO | LEU | VAL | ILE |
| 1 | | | | 5 | | | | | 10 | | | | | 15 |
| SER | SER | ARG | ILE | ASP | GLN | ASP | ASN | SER | SER | PHE | ASP | SER | LEU | SER |
| | | | | 20 | | | | | 25 | | | | | 30 |
| PRO | GLU | PRO | LYS | SER | ARG | PHE | ALA | MET | LEU | ASP | ASP | VAL | LYS | ILE |
| | | | | 35 | | | | | 40 | | | | | 45 |
| LEU | ALA | ASN | GLY | LEU | LEU | GLN | LEU | GLY | HIS | GLY | LEU | LYS | ASP | PHE |
| | | | | 50 | | | | | 55 | | | | | 60 |
| VAL | HIS | LYS | THR | LYS | GLY | GLN | ILE | ASN | ASP | ILE | PHE | GLN | LYS | LEU |
| | | | | 65 | | | | | 70 | | | | | 75 |
| ASN | ILE | PHE | ASP | GLN | SER | PHE | TYR | ASP | LEU | SER | LEU | GLN | THR | SER |
| | | | | 80 | | | | | 85 | | | | | 90 |
| GLU | ILE | LYS | GLU | GLU | GLU | LYS | GLU | LEU | ARG | ARG | THR | THR | TYR | LYS |
| | | | | 95 | | | | | 100 | | | | | 105 |
| LEU | GLN | VAL | LYS | ASN | GLU | GLU | VAL | LYS | ASN | MET | SER | LEU | GLU | LEU |
| | | | | 110 | | | | | 115 | | | | | 120 |
| ASN | SER | LYS | LEU | GLU | SER | LEU | LEU | GLU | GLU | LYS | ILE | LEU | LEU | GLN |
| | | | | 125 | | | | | 130 | | | | | 135 |
| GLN | LYS | VAL | LYS | TYR | LEU | GLU | GLU | GLN | LEU | THR | ASN | LEU | ILE | GLN |
| | | | | 140 | | | | | 145 | | | | | 150 |
| ASN | GLN | PRO | GLU | THR | PRO | GLU | HIS | PRO | GLU | VAL | THR | SER | LEU | LYS |
| | | | | 155 | | | | | 160 | | | | | 165 |
| THR | PHE | VAL | GLU | LYS | GLN | ASP | ASN | SER | ILE | LYS | ASP | LEU | LEU | GLN |
| | | | | 170 | | | | | 175 | | | | | 180 |
| THR | VAL | GLU | ASP | GLN | TYR | LYS | GLN | LEU | ASN | GLN | GLN | HIS | SER | GLN |
| | | | | 185 | | | | | 190 | | | | | 195 |
| ILE | LYS | GLU | ILE | GLU | ASN | GLN | LEU | ARG | ARG | THR | SER | ILE | GLN | GLU |
| | | | | 200 | | | | | 205 | | | | | 210 |
| PRO | THR | GLU | ILE | SER | LEU | SER | SER | LYS | PRO | ARG | ALA | PRO | ARG | THR |
| | | | | 215 | | | | | 220 | | | | | 225 |
| THR | PRO | PHE | LEU | GLN | LEU | ASN | GLU | ILE | ARG | ASN | VAL | LYS | HIS | ASP |
| | | | | 230 | | | | | 235 | | | | | 240 |
| GLY | ILE | PRO | ALA | GLU | CYS | THR | THR | ILE | TYR | ASN | ARG | GLY | GLU | HIS |
| | | | | 245 | | | | | 250 | | | | | 255 |
| THR | SER | GLY | MET | TYR | ALA | ILE | ARG | PRO | SER | ASN | SER | GLN | VAL | PHE |
| | | | | 260 | | | | | 265 | | | | | 270 |
| HIS | VAL | TYR | CYS | ASP | VAL | ILE | SER | GLY | SER | PRO | TRP | THR | LEU | ILE |
| | | | | 275 | | | | | 280 | | | | | 285 |
| GLN | HIS | ARG | ILE | ASP | GLY | SER | GLN | ASN | PHE | ASN | GLU | THR | TRP | GLU |
| | | | | 290 | | | | | 295 | | | | | 300 |
| ASN | TYR | LYS | TYR | GLY | PHE | GLY | ARG | LEU | ASP | GLY | GLU | PHE | TRP | LEU |
| | | | | 305 | | | | | 310 | | | | | 315 |
| GLY | LEU | GLU | LYS | ILE | TYR | SER | ILE | VAL | LYS | GLN | SER | ASN | TYR | VAL |
| | | | | 320 | | | | | 325 | | | | | 330 |
| LEU | ARG | ILE | GLU | LEU | GLU | ASP | TRP | LYS | ASP | ASN | LYS | HIS | TYR | ILE |
| | | | | 335 | | | | | 340 | | | | | 345 |

FIGURE 2B

```
GLU TYR SER PHE TYR LEU GLY ASN HIS GLU THR ASN TYR THR LEU
                350                 355                 360
HIS LEU VAL ALA ILE THR GLY ASN VAL PRO ASN ALA ILE PRO GLU
                365                 370                 375
ASN LYS ASP LEU VAL PHE SER THR TRP ASP HIS LYS ALA LYS GLY
                380                 385                 390
HIS PHE ASN CYS PRO GLU GLY TYR SER GLY GLY TRP TRP TRP HIS
                395                 400                 405
ASP GLU CYS GLY GLU ASN ASN LEU ASN GLY LYS TYR ASN LYS PRO
                410                 415                 420
ARG ALA LYS SER LYS PRO GLU ARG ARG ARG GLY LEU SER TRP LYS
                425                 430                 435
SER GLN ASN GLY ARG LEU TYR SER ILE LYS SER THR LYS MET LEU
                440                 445                 450
ILE HIS PRO THR ASP SER GLU SER PHE GLU
                455                 460
```

FIGURE 5A-C
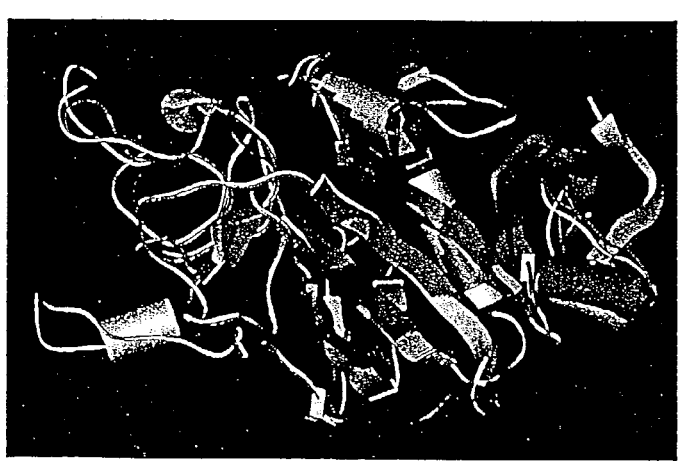

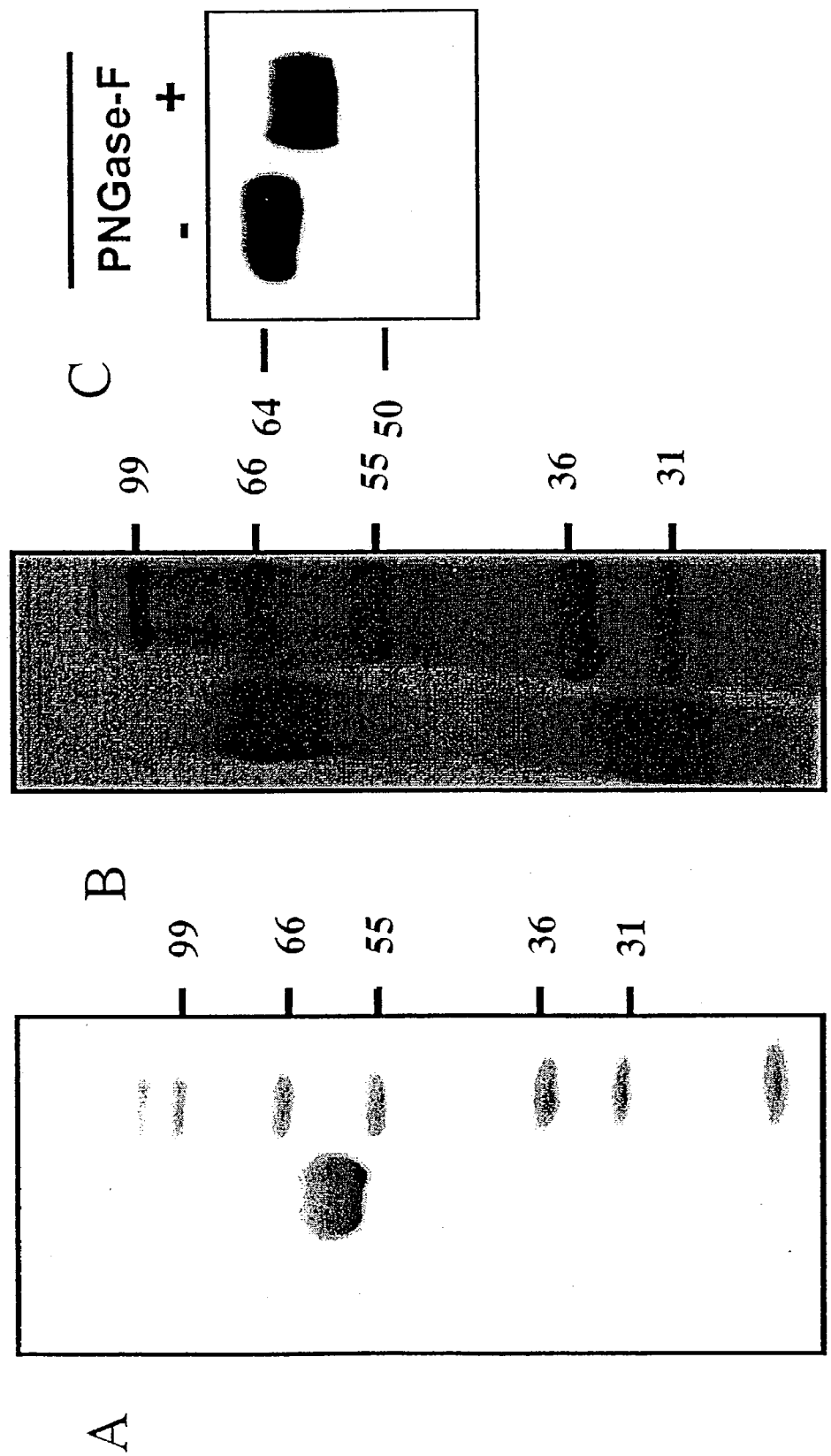
FIGURE 6A-C

FIGURE 9A-D
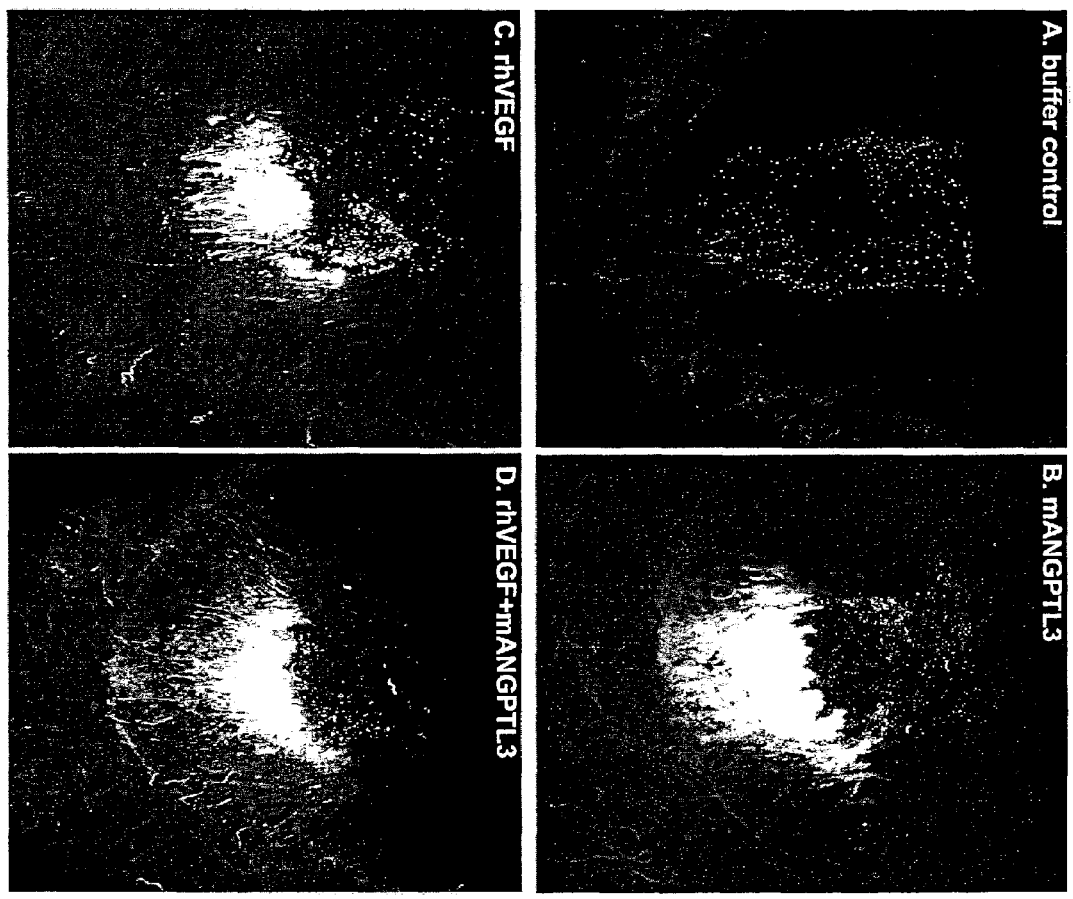

Means Table for AST
Effect: Column 1
Row exclusion: blood chem/stats/dat

| | Count | Mean | Std. Dev. | Std. Err. |
|---|---|---|---|---|
| Ad-gDmCCFL1 10^9 | 6 | 93.167 | 28.833 | 11.771 |
| Ad-gDmCCFL1 10^9 +CCl4 | 6 | 8146.167 | 5053.651 | 2063.144 |
| Ad-lacZ 10^9 | 5 | 112.400 | 56.853 | 25.426 |
| Ad-lacZ 10^9+CCl4 | 6 | 17508.167 | 9315.235 | 3802.929 |
| Ad-VEGF 10^7 | 6 | 777.333 | 1503.013 | 613.603 |
| Ad-VEGF 10^7+ CCl4 | 6 | 15646.333 | 2150.884 | 878.095 |
| NA | 6 | 192.833 | 134.847 | 55.051 |
| NA+CCl4 | 6 | 14713.000 | 3141.098 | 1282.348 |

$P<0.0001$

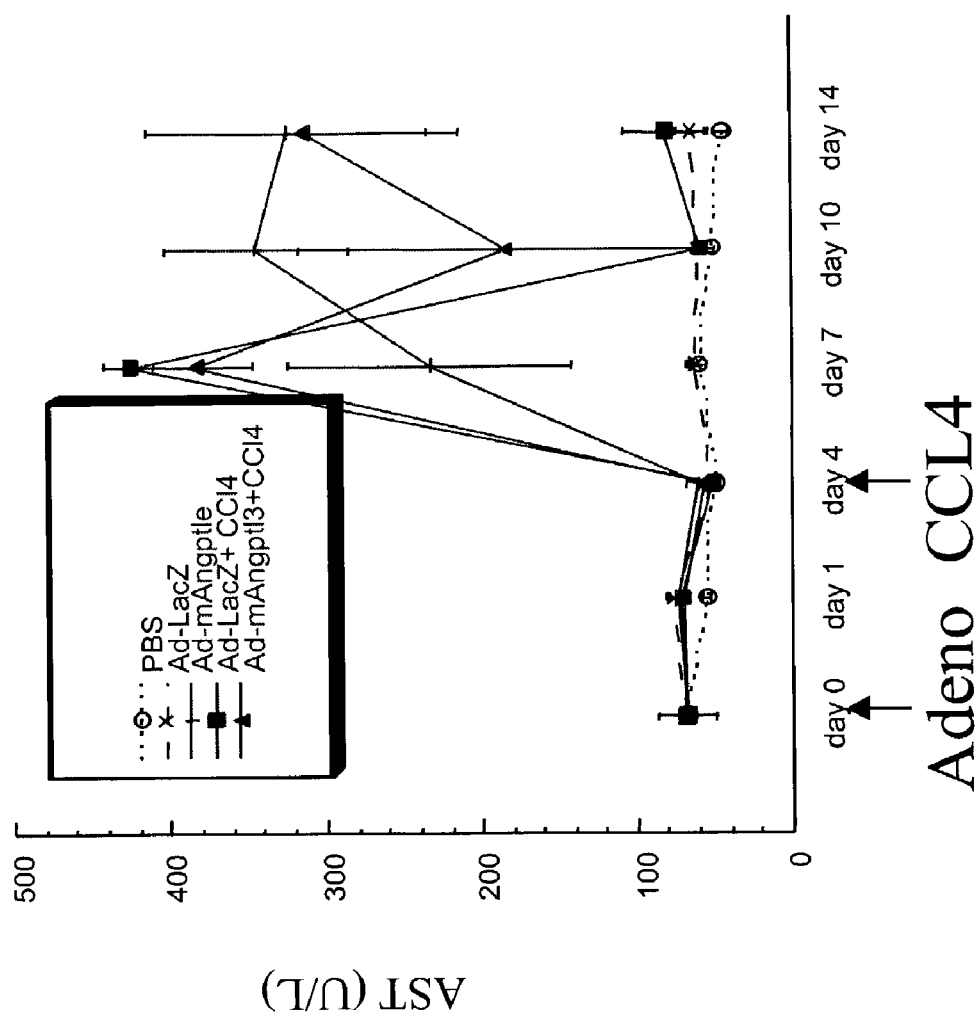

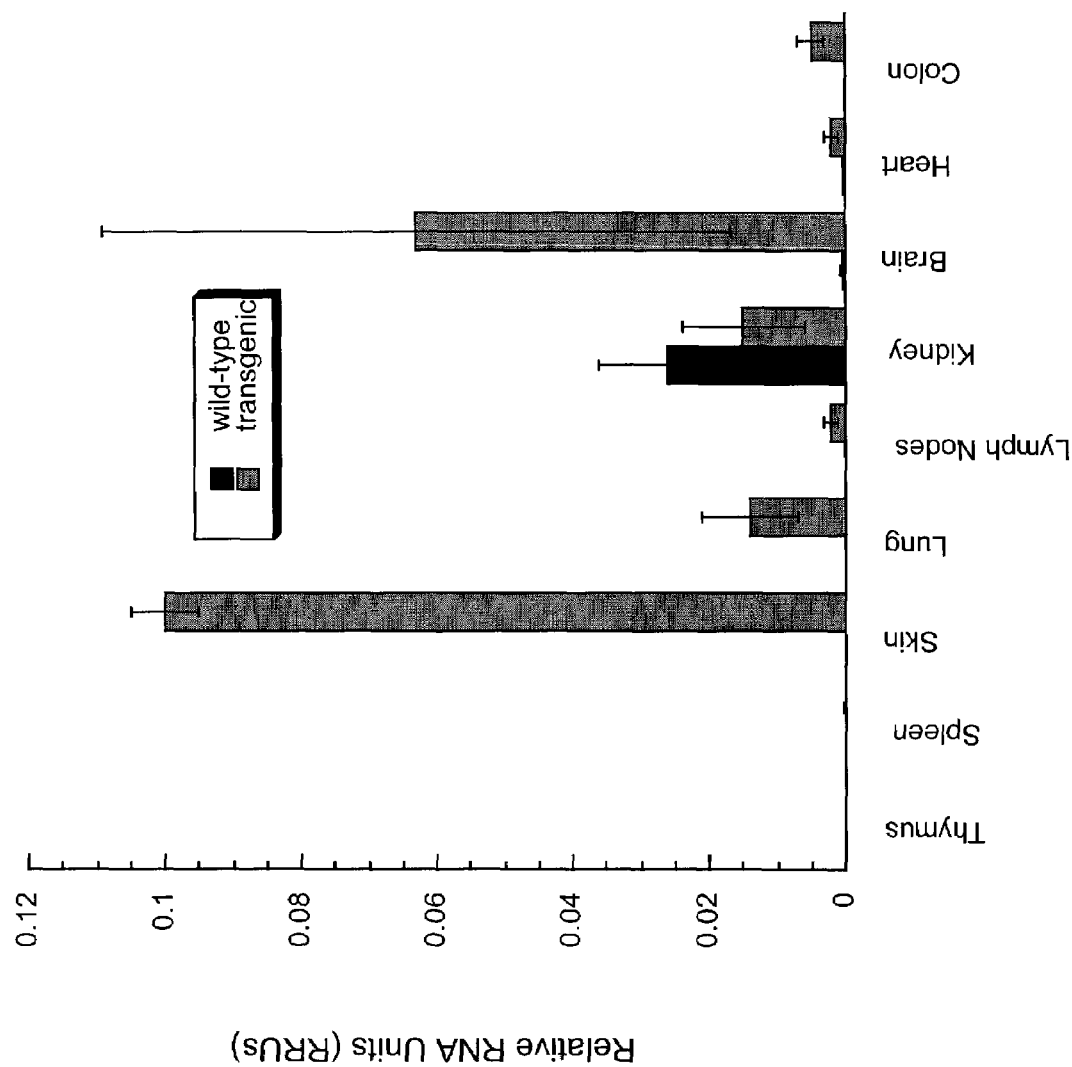

COMPOSITION COMPRISING AND METHOD OF USING ANGIOPOIETIN-LIKE PROTEIN 3 ANGPTL3

RELATED APPLICATIONS

This is a continuation in part application that claims priority under 35 U.S.C. §119(e) to U.S. provisional application No. 60/332,429, filed on Nov. 16, 2001.

BACKGROUND OF THE INVENTION

1. Field of the Invention

The present invention concerns Angptl3 polypeptides as well as methods and means for making and using such protein molecules, and antibodies binding Angptl3 polypeptides.

2. Description of the Related Art

The growth of new blood vessels is a prerequisite during normal physiological processes of embryonic and postnatal development. Such proliferation of new blood vessels from pre-existing capillaries, a process termed angiogenesis, additionally plays a key role in the pathological development of solid tumors, diabetic retinopathies, psoriasis, inflammation and rheumatoid arthritis (Ferrara, *Recent Prog. Horm. Res.* 55:15-35 (2000), discussion 35-6).

Angiogenesis not only depends on growth factors, such as vascular endothelial growth factor (VEGF) and fibroblast growth factor (FGF), but is also influenced by cell adhesion molecules (CAMs), including integrins. Inactivation of various genes encoding specific adhesion receptors or administration of blocking antibodies in animal models had profound effects on the angiogenic response of endothelial cells (Elicieri and Cheresh, *Mol. Med.*, 4:741-50 (1998)).

The integrin family of cell adhesion proteins is composed of 15 α and 8 β subunits that are expressed in at least 22 different αβ heterodimeric combinations (Byzova et al., *Mol. Cell.*, 6(4):851-60 (2000)). Among these, at least six (αvβ3, αvβ5, α5β1, α2β1, αvβ1 and α1β1) of the combinations have been implicated in angiogenesis (Hynes and Bader, *Thromb. Haemost.*, 78(1):83-7 (1997); Hynes et al., *Braz. J. Med. Biol. Res.*, 32(5):501-10 (1999)). Integrins facilitate cellular adhesion to and migration on the extracellular matrix proteins found in intercellular spaces and basement membranes.

Integrin αvβ3 is a receptor for a wide variety of extracellular matrix proteins including vitronectin, fibronectin, fibrinogen, laminin, collagen, Van Willebrand factor, osteopontin and a fragment of MMP2 (PEX) among others (for review see Eliceiri and Cheresh, *Cancer J. Sci. Am.* 6 Suppl 3:S245-9 (2000)). Despite its promiscuous ligand binding behavior, αvβ3 is not widely expressed in adult tissues, is found on some vascular, intestinal and uterine smooth muscle cells (Brem et al., *Invest. Ophthalmol. Vis. Sci.*, 35:3466-74 (1994). This receptor is also expressed on certain activated leukocytes, on macrophages and osteoclasts, where plays a crucial role during bone resorption (McHugh, et al, *J. Clin. Invest.*, 105:433-40 (2000)). Most prominently, αvβ3 becomes upregulated on endothelial cells exposed to hypoxia and cytokines such as vascular endothelial growth factor A (VEGF-A) (Suzuma et al., *Invest Ophthalmol. Vis. Sci.* 39:1029-35 (1998); Walton et al., *J. Cell. Biochem.* 78:674-80 (2000)). In vivo, increased expression of αvβ3 was observed on vascular cells within tumor granulation tissues, during wound healing, macular degeneration and other neovascular diseases. In a variety of in vitro and in vivo models of tumor angiogenesis, blockade of αvβ3 with monoclonal antibodies or ligand antagonists led to blunted blood vessel formation (Brooks et al., *Cell* 79:1157-64 (1994); Eliceiri and Cheresh, *Mol. Med.* 4:741-50 (1998)).

While there is a vast number of reports focusing on the mechanism involved in regulation of angiogenesis in pathological conditions such as tumor growth or collateral vessel formation after myocardial ischemia, surprisingly little is known about the role of the angiogenic process during liver regeneration. After partial hepatectomy (PH), both hepatocytes and nonparenchymal cells expressed vascular endothelial growth factor (VEGF) mRNA (Mochida et al. *Biochem. Biophys. Res. Commun.* 226:176-9 issn: 0006-291× (1996)), implicating that VEGF, by means of inducing angiogenesis, might play a role in liver regeneration. However, neutralizing antisera against VEGF did not alter recovery rates after injury but led to a reduction of proliferating endothelial cells and hepatocytes in this model (Taniguchi et al., *J. Histochem. Cytochem.* 49:121-30 (2001)). In support of this, the addition of the angiogenesis inhibitor TNP-470 did not impair wound healing after partial hepatectomy, suggesting that TNP470-sensitive angiogenesis is not required during liver regeneration (Tanaka et al., *Br. J. Surg.*, 83(10):1444-7 (1996)).

There is a need for the identification of novel factors which are involved in liver regeneration, and in particular in the process of angiogenesis during liver regeneration.

SUMMARY OF THE INVENTION

The present invention concerns the use of polypeptides comprising an amino acid sequence having sequence identity to the human Angptl3 sequence, or an agonist thereof, to treat tissue damage characterized by overexpression of Angptl3. In particular, the invention concerns the use of Angptl3 in the treatment (including prevention) or the identification of a human subject at risk of tissue damage, preferably liver or heart tissue damage. Accordingly, Angptl3 is believed to be involved in regulation of the angiogenic process during liver regeneration.

The present invention concerns a method of treating tissue damage characterized by overexpression of Angptl3 which comprises the treatment of tissue with an antagonist of Angptl3 of SEQ ID NO: 2 or a mammalian homologue thereof. In one embodiment, the treatment includes prevention and more specifically, the prevention of the progression of tissue damage.

In a preferred embodiment, the tissue is preferably human liver tissue. The antagonist is preferably an antagonist of Angptl3 of SEQ ID NO: 2. The tissue damage is preferably associated with inflammation or a liver tumor. The inflammation is preferably associated with a chronic liver disease selected from the group consisting of liver cirrhosis, liver fibrosis, chronic hepatitis, viral hepatitis A, B, C, D, E and G, toxic metabolic liver damage, fatty liver, ischemia reperfusion injury of the liver and sepsis. The liver cirrhosis is alcoholic liver cirrhosis or primary biliary cirrhosis (PBC). The hepatitis is selected from the group consisting of chronic autoimmune hepatitis, chronic alcoholic hepatitis and non-alcoholic steatohepatits (NASH). The liver tumor is selected from the group consisting of hepatocellular carcinoma, cholangiocarcinoma and metastatic cancer of the liver.

In another embodiment, the tissue is preferably heart tissue. The tissue damage is preferably associated with inflammation. The tissue damage is preferably associated with a cardiac disease characterized by elevated expression of Angptl3. In another aspect, the tissue damage is associated with a cardiac disease the pathogenesis of which includes an inflammatory response, or in the development of which inflammation is a risk factor. The cardiac disease is preferably selected from the group consisting of coronary artery disease, cardiomyopathy, myocarditis, congestive heart failure (CHF), and myocardial infarction. The cardiomyopathy is preferably selected from the group consisting of non-specific hypertrophy and dilated cardiomyopathy.

In another embodiment, the antagonist is an anti-Angptl3 antibody, an anti-αvβ3 antibody, an immunoadhesin or a small molecule. The antibody is preferably a monoclonal antibody, an antibody fragment or a single-chain antibody that is selected from the group consisting of Fab, Fab', F(ab')$_2$ and Fv fragments. The monoclonal antibody is preferably chimeric, humanized or human. The immunoadhesin comprises at least the ligand-binding region of αvβ3 fused to an immunoglobulin sequence or comprises at least the receptor-binding region of Angptl3 used to an immunoglobulin sequence.

In another aspect, the present invention includes a method for the treatment of a chronic liver disease in a mammalian subject, comprising administering to a mammalian subject in need of an effective amount of an antagonist of Angptl3 of SEQ ID NO: 2, or a mammalian homologue thereof. In one embodiment, the mammalian subject is human. The treatment includes prevention and more specifically, the prevention of the progression of liver disease. The antagonist administered is an antagonist of Angptl3 of SEQ ID NO: 2 or an antibody, in particular, an anti-Angptl3 antibody or an anti-αvβ3 antibody. The chronic liver is characterized by the elevated expression of Angptl3. The liver disease is selected from the group consisting of liver cirrhosis, liver fibrosis, chronic hepatitis, viral hepatitis A, B, C, D, E and G, toxic metabolic liver damage, fatty liver, ischemia reperfusion injury of the liver and sepsis.

In another aspect, the present invention includes a method for the treatment of a heart disease in a mammalian subject, comprising administering to the subject an effective amount of an antagonist of Angptl3 of SEQ ID NO: 2, or a mammalian homologue thereof. In one embodiment, the mammalian subject is human. The treatment includes prevention and more specifically, the prevention of the progression of heart disease. The antagonist administered is an antagonist of Angptl3 of SEQ ID NO: 2. The heart disease is selected from the group consisting of coronary artery disease, cardiomyopathy, myocarditis, congestive heart failure (CHF), and myocardial infarction. The antagonist is an anti-Angptl3 antibody or an anti-αvβ3 antibody.

In another aspect, the present invention includes a method for the treatment of acute liver disease, comprising administering to a mammalian subject in need of a therapeutically effective amount of a polypeptide comprising an amino acid sequence having at least 80% sequence identity to the human Angptl3 sequence of SEQ ID NO: 2, or an agonist thereof. In one embodiment, the mammalian subject is human. The treatment includes prevention and more specifically, the prevention of the progression of acute liver disease. The polypeptide comprises an amino acid sequence having at least 98% identity to the human Angptl3 sequence of SEQ ID NO: 2, or an agonist thereof. In a preferred embodiment, the polypeptide comprises amino acid regions 281-293 (P1, SEQ ID NO: 14), 442-460 (P2, SEQ ID NO: 15), and 415-430 (P3, SEQ ID NO: 17) of the human Angptl3 sequence of SEQ ID NO: 2. In a further preferred embodiment, the polypeptide comprises the fibrinogen domain of the human Angptl3 sequence of SEQ ID NO: 2.

In an even further preferred embodiment, the method comprises the administration of an additional therapeutic agent. The additional therapeutic agent is a vascular endothelial growth factor (VEGF) or fibroblast growth factor (FGF). The agonist is an agonist antibody specifically binding Angptl3 or αvβ3.

In another aspect, the present invention includes a method of inducing liver regeneration following acute liver injury, comprising administering to a mammalian subject in need a therapeutically effective amount of a polypeptide comprising an amino acid sequence having at least 80% sequence identity to the human Angptl3 sequence of SEQ ID NO: 2, or an agonist thereof. The mammalian subject is preferably human. The human subject may have been diagnosed with an inflammatory liver disease, such as chronic, alcoholic or viral hepatitis, sepsis, primary biliary cirrhosis (PBC) or primary or metastatic liver cancer, has suffered chemical or mechanical injury to the liver or has been subject to hepatectomy, due to any cause, such as chronic hepatitis, liver cirrhosis, primary or metastatic liver cancer, or gallbladder cancer. Alternatively, the patient may have been exposed to chemical agents or other environmental or other known factors to cause liver injury, and treated before such injury develops. Preventative treatment is specifically within the scope of the invention.

In another aspect, the present invention includes a method for inducing angiogenesis in a tissue comprising treating the tissue with an effective amount of a polypeptide comprising an amino acid sequence having at least 80% sequence identity to the human Angptl3 sequence of SEQ ID NO: 2, or an agonist thereof. In one embodiment, the tissue is cardiac tissue or liver tissue which may be diseased liver tissue that has been injured as a result of an infectious or autoimmune process, mechanical or chemical injury or cancer or metastatic cancer. Preventative treatment and more specifically the prevention of the progression of the disease is specifically within the scope of the invention.

In another aspect, the present invention includes a method for inhibiting an undesired increase in vascular permeability in a tissue comprising administering an effective amount of an antagonist of a Angptl3 of SEQ ID NO: 2, or a mammalian homologue thereof. The increase in vascular permeability may be an increase in permeability of small vessels following tissue damage or may follow necrosis of vascular endothelium due to exposure to toxins. The increased vascular permeability is associated with inflammation, preferably chronic inflammation. The tissue is liver tissue or heart tissue. Preventative treatment and more specifically the prevention of the progression of the disease is specifically within the scope of the invention.

In another aspect, the present invention includes a method for identifying a human subject at risk of cardiovascular disease, preferably before serious damage occurs. The method comprises determining the level of Angptl3 mRNA or its expression product in the heart tissue of said subject, relative to the level of Angptl3 or its expression product in the heart tissue of said subject, relative to the level of Angptl3 or its expression product in normal heart tissue, and identifying the subject as being at risk if the level of Angptl3 mRNA or its expression product in the heart tissue of the subject is elevated relative to the normal heart tissue. The heart tissue sample may be taken from a subject suspected of being at risk of cardiovascular disease, preferably from a human patient, and may be subjected to differential gene expression analysis to detect upregulation of a human Angptl3 gene of SEQ ID NO: 1, comparing the expression of Angptl3 in the at risk heart tissue sample to expression in a second heart sample taken from normal heart tissue. The differential gene expression analysis may be performed by known techniques, including northern blotting, in situ hybridization, reverse transcription polymerase chain reaction (RT-PCR) or by using microarray technique.

In another aspect, the present invention includes a method for identifying a human subject at risk of liver damage, preferably before serious damage occurs. The method comprises determining the level of Angptl3 mRNA or its expression product in the liver tissue of said subject, relative to the level of Angptl3 or its expression product in normal liver tissue, and identifying the subject as being at risk if the level of Angptl3 mRNA or its expression product in the liver tissue of the subject is elevated relative to the normal liver tissue. The liver tissue sample may be taken from a subject suspected of being at risk of liver damage, preferably from a human patient, and may be subjected to differential gene expression analysis to detect upregulation of a human Angptl3 gene of SEQ ID NO: 1, comparing the expression of Angptl3 in the at risk liver sample to expression in a second liver sample taken from normal liver tissue. The differential gene expression analysis may be performed by known techniques, including northern blotting, in situ hybridization, reverse transcription polymerase chain reaction (RT-PCR) or by using microarray technique.

In all therapeutic applications (including prevention), the Angptl3 polypeptide, or an agonist or an antagonist thereof, may be administered in combination with a further therapeutic agent, such as a further angiogenic factor, e.g. vascular endothelial growth factors (VEGF), or fibroblast growth factor (FGF).

BRIEF DESCRIPTION OF THE DRAWINGS

FIG. 1 is the nucleotide sequence of Angptl3 (SEQ. ID NO: 1) (DNA 16451).

FIGS. 2A and 2B are the amino acid sequence of Angptl3 (SEQ. ID NO: 2).

FIGS. 5A-C show homology modeling of the fibrinogen domain of Angptl3. (A) Ribbon diagram of the superimposition of the x-ray structure of the C terminus of the γ-chain of human fibrinogen (3FIB) in white, and the modeled structure of the fibrinogen-like domain of Angptl3 in green. Alpha helices are shown as cylinders and beta strands as arrows. Regions that differ in both structures are labeled. (B) Ribbon diagram of the modeled structure of the fibrinogen-like domain of Angptl3 in green. Regions P1, P1, and P3 involved in α5β3 are highlighted in yellow. (C) Sequence alignment of the C terminus of the γ-chain of human fibrinogen (3FIB) (SEQ ID NO: 27) and the fibrinogen-like domain of Angptl3 (SEQ ID NO: 28) and human angiopoietin 1 (SEQ ID NO: 29), 2 (SEQ ID NO: 30) and 4 (SEQ ID NO: 31). Hydrophilic and charged residues are displayed in blue, and aromatic/hydrophobic residues in orange. The consensus sequence is shown below the alignment; with conserved hydrophilic/charged and aromatic/hydrophobic mutations marked as blue and orange squares, respectively. Residues corresponding to the peptides used in our study are boxed yellow. Numbering corresponds to the 3FIB x-ray structure.

FIGS. 6A-C present evidence that Angptl3 is a secreted glycoprotein. (A) Coomassie-stained SDS-polyacrylamide gel of immunoaffinity purified human Angptl3. (B) Silver stained SDS-polyacrylamide-gel of immunoaffinity purified murine Angptl3 from transiently transfected CHO cells. (C) Comparison of molecular weights of recombinant Angptl3 protein with (+) or without (−) PNGase-F treatment. The predicted molecular weight for gD tagged hAngptl3 is 60 kDa. Western blot were conducted using an anti-gD antibody.

FIGS. 9A-E show the effects of CCLF1 on the induction of in vivo angiogenesis in the rat cornea. (A) Representative flat-mount phtomicrographs of rat corneas 6 days after implantation of hydron pellets treated with buffer (Control), (B) murine Angptl3 (500 ng), (C) VEGF (100 ng), (D) murine Angptl3 (500 ng) and VEGF (100 ng). (E) Summary data of the in vivo angiogenic response to control, VEGF (100 ng), mAngptl3 (500 ng), mAngptl3 (500 ng) and combinations as indicated. Data are expressed as mean±SE, n=5 animals/group. p<0.005 compared to control (Mann-Whitney test for nonparametric values).

FIG. 10A shows equal levels of expression at day 7 after adenoviral infection at day 0 and CC14 treatment at day 4 of all constructs tested. FIG. 10B shows AST levels in serum of mice at day 7 treated with the indicated viral vectors at day 0 and CC14 at day 4. (P<0.0001)

FIGS. 11A-B show an increase in serum AST levels after prolonged expression of murine Angptl3 in livers of C57/B16 wild-type mice. FIG. 11A shows AST levels in serum of mice at various time-points after treatment with the indicated viral constructs at day 0 and CC14 treatment at day 4. FIG. 11B shows an increase in ALT and AST levels in serum of RAG2 knock-out mice 2 weeks after adenoviral infection. Results are shown in means±SEM. The number of animals per group was 6 (P<0.0001).

FIGS. 12A-D show an increase in vascular leakage in skin of K5-Angptl3 transgenic mice or in wild-type FVB mice in response to intra-dermal administration of Angptl3-expressing adenoviral vectors. FIG. 12A shows results from real-time RT-PCR analysis of RNA isolated from various organs of transgenic and liter matched wild-type control mice. Transgene expression in the skin reached about 10% of the endogenous Angptl3 expression levels that was detected in the liver. FIG. 12B shows results from real-time RT-PCR analysis of RNA isolated from skin biopsies of transgenic and liter matched wild-type control mice at different time points postnatal. FIG. 12C shows results from Evans Blue assay that was performed on 11 week-old transgenic and liter matched wild-type control mice to determine the level of vascular permeability. Transgenic mice displayed a significant increase in vascular permeability in basal conditions (left panels) but not when challenged with mustard oil (right panel). The amount of extravasated Evans Blue dye was measured by light spectrophotometer at 610 nm absorption and expressed as the content dye per 1 mg of wet weight of tissue (lower panel). Results are shown as means±SEM, and the number of animals per group was 6, P<0.05. FIG. 12D shows results from Evan Blue assay performed 6 days post administration of FVB mice injected intra-dermally with $1\times10^9$ Pfu of the indicated adenoviral construct. Skin of mice treated with Angptl3 (p<0.05) or VEGF (p<0.005) displayed a significant increase in vascular permeability under basal conditions (left panels) when compared to control treated mice (LacZ). The amounts of extravasated Evans Blue dye was measured with a light spectrophotometer at 610 nm and expressed as the content dye per 1 mg of wet weight of tissue. Results are shown as means±SEM, and the number of animals per group was 6, P<0.05.

DETAILED DESCRIPTION OF THE PREFERRED EMBODIMENT

A. Definitions

Figure 3A:
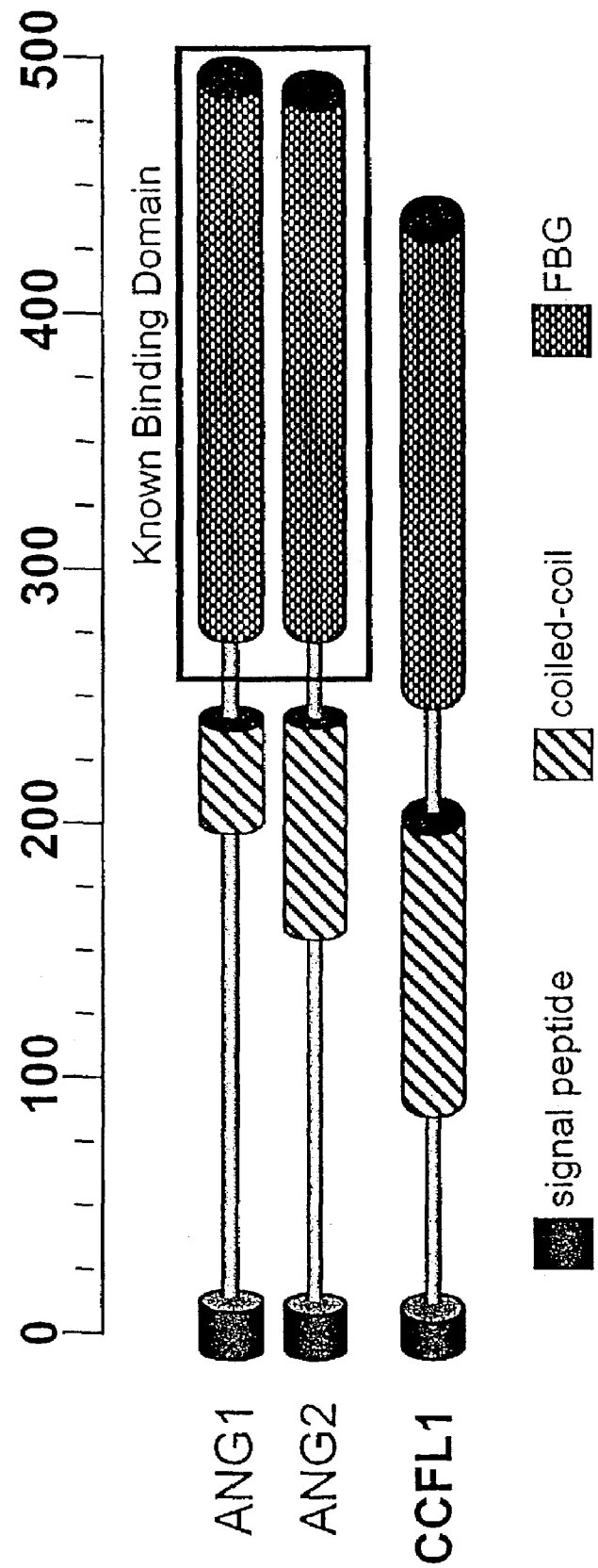
FIG. 3A is a comparison of the domain structure of Angptl3 (SEQ ID NO: 2) and angiopoietin-1 (ANG1) and angiopoietin-2 (ANG2).

The term "liver disease" is used herein in the broadest sense and refers to any disease of the liver associated with any type of liver injury, regardless of the underlying cause. Thus, liver disease may result, for example, from infectious or autoimmune processes, from mechanical or chemical injury to the liver, or from cancer, all of which are included within the definition of "liver disease." Chemical injury to the liver can be caused by a variety of toxins, such as alcohol, carbon tetrachloride, trichloroethylene, iron overdose, drug overdose, drug side-effects etc.

The term "tissue damage associated with inflammation," and grammatical variants thereof, are used to refer to any tissue damage that, at least partially, results from inflammation or is accompanied by an inflammatory response. The tissue may, for example, be liver tissue or hear tissue, and the tissue damage may, for example, be associated with an inflammatory liver disease, or a heart disease.

The term "inflammatory liver disease" is used herein to refer to any liver disease, the pathogenesis of which involves the activation and recruitment of inflammatory cells to the liver, regardless of whether the underlying cause is an infectious or autoimmune process, chemical injury to the liver, or other. Thus, inflammatory liver diseases include, without limitation, alcoholic hepatitis and cirrhosis, viral hepatitis, ischemia reperfusion injury of the liver, sepsis and primary biliary cirrhosis (PBC). For review, see Lawson et al., Toxicol Sci 54:509-16 (2000).

The term "chronic liver disease" is used herein to refer to liver diseases characterized by the overexpression of Angptl3, and includes, without limitation, inflammatory diseases of the liver and liver tumors. Inflammatory diseases of the liver include, for example, cirrhosis, such as, alcoholic liver cirrhosis and primary biliary cirrhosis (PBC), liver fibrosis, chronic hepatitis, i.e. chronic autoimmune hepatitis, chronic alcoholic hepatitis, non-alcoholic steatohepatitis (NASH, also known as steatosis), viral hepatitis A, B, C, D, E and G, toxic metabolic liver damage, fatty liver, ischemia reperfusion injury of the liver, and sepsis. Liver tumors include, for example, hepatocellular carcinoma, cholangiocarcinoma, and metastatic cancer of the liver.

The term "acute liver disease" is used herein to refer to a liver disease of short duration, the history of which typically does not exceed six months. Included within this definition are, for example, acute hepatitis, i.e. acute autoimmune hepatitis and acute alcoholic hepatitis, and acute liver failure. Specifically included within the definition is any liver disease of short duration that is not characterized by the overexpression of Angptl3.

The term "cardiac disease" is used herein to refer to any heart disease the pathogenesis of which includes an inflammatory response, or in the development of which inflammation is a risk factor. Specifically included within the definition is any cardiac disease characterized by elevated expression of Angptl3. Cardiac diseases encompassed by this definition include, without limitation, coronary artery disease, cardiomyopathy, such as hypertrophic cardiomyopathy, non-specific hypertrophy and dilated cardiomyopathy, myocarditis, congestive heart failure (CHF), heart attack, and the like.

"Alcoholic hepatitis," as used herein, includes acute and chronic hepatitis resulting from excessive alcohol consumption, and can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma.

The term "viral hepatitis," as used herein, refers to hepatitis resulting from hepatitis A, B, C, D, E, or G infection.

The hepatitis A virus (HAV) is a virus from the enterovirus group of the Picornaviridae family, usually causing a mild illness characterized by sudden onset of fever, malaise, nausea, anorexia, and abdominal discomfort, followed in several days by jaundice.

The hepatitis B virus (HBV) is a mostly double-stranded DNA virus in the Hepadnaviridae family. HBV causes hepatitis in human and related virus in this family cause hepatitis in ducks, ground squirrels and woodchucks. The HBV genome has four genes: pol, env, pre-core and X that respectively encode the viral DNA-polymerase, envelope protein, pre-core protein (which is processed to viral capsid) and protein X. The function of protein X is not clear but it may be involved in the activation of host cell genes and the development of cancer. HBV causes acute and chronic hepatitis. The chances of becoming chronically infected depends upon age. About 90% of infected neonates and 50% of infected young children will become chronically infected. In contrast, only about 5% to 10% of immunocompetent adults infected with HBV develop chronic hepatitis B.

The hepatitis C virus (HCV) is a positive, single-stranded RNA virus in the Flaviviridae family. The genome is approximately 10,000 nucleotides and encodes a single polyprotein of about 3,000 amino acids. The polyprotein is processed by host cell and viral proteases into three major structural proteins and several non-structural protein necessary for viral replication. Several different genotypes of HCV with slightly different genomic sequences have been identified that correlate with differences in prognosis and response to treatment. About 85% of individuals acutely infected with HCV become chronically infected. Hence, HCV is a major cause of chronic (lasting longer than six months) hepatitis. Once chronically infected, the virus is almost never cleared without treatment. In rare cases, HCV infection causes clinically acute disease and even liver failure, however, most instances of acute infection are clinically undetectable.

The hepatitis D virus (HDV, also called delta virus) is a small circular RNA virus. HDV is replication defective and therefore cannot propagate in the absence of another virus. In humans, HDV infection only occurs in the presence of HBV infection.

The hepatitis E virus (HEV) usually causes hepatitis which is clinically indistinguishable from hepatitis A disease. Symptoms include malaise, anorexia, abdominal pain, arthralgia, and fever. Hepatitis E occurs in both epidemic and sporadic-endemic forms, usually associated with contaminated drinking water.

The hepatitis G virus (HBV) is a relatively newly discovered flavivirus, related to but distinct from HCV, that may cause acute and chronic hepatitis.

Ischemia reperfusion injury occurs when the flow of blood to a region of the body is temporarily halted (ischemia) and then re-established (reperfusion). The terms "ischemia reperfusion injury" and "ischemic reperfusion injury," which are used interchangeably, refer to the initial damage associated with oxygen deprivation of a cell and the subsequent damage associated with the inflammatory response when the cell is resupplied with oxygen. Ischemia reperfusion injury can occur during certain surgical procedures, such as repair of certain aortic aneurysms and organ transplantation. The injury may occur in the parts of the body to which the blood supply was interrupted, or it can occur in parts fully supplied with blood during the period of ischemia. Ischemia reperfusion injury of the liver may result, for example, from hepatic and biliary surgical resections, and clinically is manifested by such complications as hepatic dysfunction including acute hepatocellular damage and necrosis.

"Primary biliary cirrhosis (PBC)" is a disease characterized by inflammatory destruction of the small bile ducts within the liver. PBC eventually leads to cirrhosis of the liver. The etiology of PBC is not entirely understood, but because of the presence of autoantibodies, it is generally thought to be an autoimmune disease, however, other etiologies, such as infectious agents, have not been completely excluded. About 90% of patients diagnosed with PBC are women, most commonly between the ages of 40 and 60 years.

"Sepsis" is a result of bacterial infection that can originate in any part of the body, including the liver or biliary tract. Sepsis can be a life threatening situation, especially in people with a weakened immune system.

The term "angiogenesis," as used herein, refers to the process whereby new blood vessels emerge from existing vasculature and requires both proliferation and motility of the endothelial cells to proceed.

The term "cirrhosis" is used herein to refer to a pathologic liver condition characterized anatomically by widespread nodules in the liver combined with fibrosis. Cirrhosis is the final common pathway for must types of chronic liver diseases, including those associated with chronic alcohol abuse, chronic viral hepatitis, metabolic and biliary diseases.

The terms "Angptl3 polypeptide", "Angptl3 protein", and "Angptl3" are used interchangeably, and encompass native sequence Angptl3 and Angptl3 polypeptide variants (which are further defined herein). The Angptl3 polypeptide may be isolated from a variety of sources, such as from human tissue types or from another source, or prepared by recombinant and/or synthetic methods. In is noted, that Angptl3 was earlier also referred to as "FLS139," "NL6," or "CCFL1" Accordingly, any mention of Angptl3 should also be read as referring to FLS139, NL6 and CCFL1 polypeptides.

A "native sequence Angptl3" or "native Angptl3" comprises a polypeptide having the same amino acid sequence as a Angptl3 molecule derived from nature. Such native sequence Angptl3 can be isolated from nature or can be produced by recombinant and/or synthetic means. The term "native sequence Angptl3" or "native Angptl3" specifically encompasses naturally-occurring truncated or secreted forms (e.g., an extracellular domain sequence), naturally-occurring variant forms (e.g., alternatively spliced forms) and naturally-occurring allelic variants of Angptl3. In one embodiment of the invention, the native sequence Angptl3 is a mature or full-length native sequence Angptl3 comprising amino acids 1 to 460 of SEQ ID NO: 2. While the human Angptl3 polypeptide of SEQ ID NO: 2 is shown to begin with the methionine residue designated herein as amino acid position 1, it is conceivable and possible that another methionine residue located either upstream or downstream from amino acid position 1 in SEQ ID NO: 2 may be employed as the starting amino acid residue for the Angptl3 polypeptide. In addition, the terms "native sequence Angptl3" and "native Angptl3" specifically include polypeptide without the initiating methionine.

The "Angptl3 variant" or "Angptl3 variant polypeptide," which terms are used interchangeably, means an active Angptl3 polypeptide as defined below having at least about 80% amino acid sequence identity with the amino acid sequence of (a) residues 1 to 460 of the Angptl3 polypeptide of SEQ ID NO: 2, or a non-human mammalian homologue thereof, or (b) another specifically derived fragment of the amino acid sequence of SEQ ID NO:2 or a non-human mammalian homologue thereof. Such Angptl3 variant polypeptides include, for instance, Angptl3 polypeptides wherein one or more amino acid residues are added, or deleted, at the N- and/or C-terminus, as well as within one or more internal domains, of the sequence of SEQ ID NO: 2. Ordinarily, a Angptl3 variant polypeptide will have at least about 80% amino acid sequence identity, more preferably at least about 81% amino acid sequence identity, more preferably at least about 82% amino acid sequence identity, more preferably at least about 83% amino acid sequence identity, more preferably at least about 84% amino acid sequence identity, more preferably at least about 85% amino acid sequence identity, more preferably at least about 86% amino acid sequence identity, more preferably at least about 87% amino acid sequence identity, more preferably at least about 88% amino acid sequence identity, more preferably at least about 89% amino acid sequence identity, more preferably at least about 90% amino acid sequence identity, more preferably at least about 91% amino acid sequence identity, more preferably at least about 92% amino acid sequence identity, more preferably at least about 93% amino acid sequence identity, more preferably at least about 94% amino acid sequence identity, more preferably at least about 95% amino acid sequence identity, more preferably at least about 96% amino acid sequence identity, more preferably at least about 97% amino acid sequence identity, more preferably at least about 98% amino acid sequence identity and yet more preferably at least about 99% amino acid sequence identity with residues 1 to 460 of the Angptl3 polypeptide of SEQ ID NO: 2, or a non-human mammalian homologue thereof. Angptl3 variant polypeptides do not encompass a native Angptl3 polypeptide sequence. Ordinarily, Angptl3 variant polypeptides are at least about 10 amino acids in length, often at least about 20 amino acids in length, more often at least about 30 amino acids in length, more often at least about 40 amino acids in length, more often at least about 50 amino acids in length, more often at least about 60 amino acids in length, more often at least about 70 amino acids in length, more often at least about 80 amino acids in length, more often at least about 90 amino acids in length, more often at least about 100 amino acids in length, more often at least about 150 amino acids in length, more often at least about 200 amino acids in length, more often at least about 250 amino acids in length, more often at least about 300 amino acids in length, or more. Particularly preferred Angptl3 variants retain at least one of amino acid regions 281 to 193, 415 to 430, and 442-460 of the native human Angptl3 sequence of SEQ ID NO: 2, or corresponding region(s) of a non-human mammalian Angptl3 homologue, or contain only conservative amino acid substitutions within such regions.

The term "fibrinogen domain" or "fibrinogen-like domain" is used to refer to amino acids from about position 238 to about position 460 in the amino acid sequence of Angptl3 (SEQ ID NO: 2).

"Percent (%) amino acid sequence identity" with respect to the Angptl3 polypeptide sequences identified herein is defined as the percentage of amino acid residues in a candidate sequence that are identical with the amino acid residues in a Angptl3 sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % amino acid sequence identity values are obtained as described below by using the sequence comparison computer program ALIGN-2, wherein the complete source code for the ALIGN-2 program is provided in FIGS. 4A-Q. The ALIGN-2 sequence comparison computer program was authored by Genentech, Inc. and the source code shown in FIGS. 4A-Q has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in FIGS. 4A-Q. The ALIGN-2 program should be compiled for use on a UNIX operating system, preferably digital UNIX V4.0D. All sequence comparison parameters are set by the ALIGN-2 program and do not vary.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Unless specifically stated otherwise, all % amino acid sequence identity values used herein are obtained as described above using the ALIGN-2 sequence comparison computer program. However, % amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"Angptl3 variant nucleic acid sequence" means a nucleic acid molecule which encodes an active Angptl3 polypeptide as defined below and which has at least about 80% nucleic acid sequence identity with either (a) a nucleic acid sequence which encodes residues 1 to 460 of the Angptl3 amino acid sequence of SEQ ID NO: 2, or a non-human mammalian homologue thereof, or (b) a nucleic acid sequence which encodes another specifically derived fragment of the amino acid sequence of SEQ ID NO: 2 or a non-human mammalian homologue. Ordinarily, a Angptl3 variant polynucleotide will have at least about 80% nucleic acid sequence identity, more preferably at least about 81% nucleic acid sequence identity, more preferably at least about 82% nucleic acid sequence identity, more preferably at least about 83% nucleic acid sequence identity, more preferably at least about 84% nucleic acid sequence identity, more preferably at least about 85% nucleic acid sequence identity, more preferably at least about 86% nucleic acid sequence identity, more preferably at least about 87% nucleic acid sequence identity, more preferably at least about 88% nucleic acid sequence identity, more preferably at least about 89% nucleic acid sequence identity, more preferably at least about 90% nucleic acid sequence identity, more preferably at least about 91% nucleic acid sequence identity, more preferably at least about 92% nucleic acid sequence identity, more preferably at least about 93% nucleic acid sequence identity, more preferably at least about 94% nucleic acid sequence identity, more preferably at least about 95% nucleic acid sequence identity, more preferably at least about 96% nucleic acid sequence identity, more preferably at least about 97% nucleic acid sequence identity, more preferably at least about 98% nucleic acid sequence identity and yet more preferably at least about 99% nucleic acid sequence identity with either (a) a nucleic acid sequence which encodes residues 1 to 460 of SEQ ID NO:2, or a non-human mammalian homologue of such human polypeptide.

Ordinarily, Angptl3 variant nucleic acid sequences are at least about 30 nucleotides in length, often at least about 60 nucleotides in length, more often at least about 90 nucleotides in length, more often at least about 120 nucleotides in length, more often at least about 150 nucleotides in length, more often at least about 180 nucleotides in length, more often at least about 210 nucleotides in length, more often at least about 240 nucleotides in length, more often at least about 270 nucleotides in length, more often at least about 300 nucleotides in length, more often at least about 450 nucleotides in length, more often at least about 600 nucleotides in length, more often at least about 900 nucleotides in length, or more.

"Percent (%) nucleic acid sequence identity" with respect to the Angptl3 polypeptide-encoding nucleic acid sequences identified herein is defined as the percentage of nucleotides in a candidate sequence that are identical with the nucleotides in a Angptl3 polypeptide-encoding nucleic acid sequence, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For purposes herein, however, % nucleic acid sequence identity values are obtained as described below by using the sequence comparison computer program ALIGN-2. The ALIGN-2 sequence comparison computer program was authored by Genentech, Inc. and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco. The ALIGN-2 program should be compiled for use on a UNIX operating system, preferably digital UNIX V4.0D. All sequence comparison parameters are set by the ALIGN-2 program and do not vary.

For purposes herein, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

Unless specifically stated otherwise, all % nucleic acid sequence identity values used herein are obtained as described above using the ALIGN-2 sequence comparison computer program. However, % nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, Angptl3 variant polynucleotides are nucleic acid molecules that encode an active Angptl3 polypeptide and which are capable of hybridizing, preferably under stringent hybridization and wash conditions, to nucleotide sequences encoding the full-length Angptl3 polypeptide of SEQ ID NO: 2. Angptl3 variant polypeptides may be those that are encoded by a Angptl3 variant polynucleotide.

The term "positives", in the context of the amino acid sequence identity comparisons performed as described above, includes amino acid residues in the sequences compared that are not only identical, but also those that have similar properties. Amino acid residues that score a positive value to an amino acid residue of interest are those that are either identical to the amino acid residue of interest or are a preferred substitution of the amino acid residue of interest.

For purposes herein, the % value of positives of a given amino acid sequence A to, with, or against a given amino acid sequence B (which can alternatively be phrased as a given amino acid sequence A that has or comprises a certain % positives to, with, or against a given amino acid sequence B) is calculated as follows:

100 times the fraction X/Y where X is the number of amino acid residues scoring a positive value as defined above by the sequence alignment program ALIGN-2 in that program's alignment of A and B, and where Y is the total number of amino acid residues in B. It will be appreciated that where the length of amino acid sequence A is not equal to the length of amino acid sequence B, the % positives of A to B will not equal the % positives of B to A.

The term "antibody" is used in the broadest sense and specifically covers, for example, single anti-Angptl3 monoclonal antibodies (including agonist, antagonist, and neutralizing antibodies), anti-Angptl3 antibody compositions with polyepitopic specificity, single chain anti-Angptl3 antibodies, and fragments of anti-Angptl3 antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.*, 8(10):1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment, which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the V$_H$-V$_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa ( ) and lambda ( ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called , , , , and , respectively. The subunit structures and three-dimensional configurations of different classes of immunoglobulins are well known.

The term "diabodies" refers to small antibody fragments with two antigen-binding sites, which fragments comprise a heavy-chain variable domain (V$_H$) connected to a light-chain variable domain (V$_L$) in the same polypeptide chain (V$_H$-V$_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR) regions. The variable domains of native heavy and light chains each comprise four FR regions, largely adopting a -sheet configuration, connected by three CDRs, which form loops connecting, and in some cases forming part of, the -sheet structure. The CDRs in each chain are held together in close proximity by the FR regions and, with the CDRs from the other chain, contribute to the formation of the antigen-binding site of antibodies (see Kabat et al., *NIH Publ. No.*91-3242, Vol. I, pages 647-669 (1991)). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e., residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institute of Health, Bethesda, Md. [1991]) and/or those residues from a "hypervariable loop" (i.e., residues 26-32 (L1), 50-52 (L2) and 91-96 (L3) in the light chain variable domain and 26-32 (H1), 53-55 (H2) and 96-101 (H3) in the heavy chain variable domain; Clothia and Lesk, *J. Mol. Biol.*, 196:901-917 [1987]). "Framework" or "FR" residues are those variable domain residues other than the hypervariable region residues as herein defined.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see, Jones et al., *Nature*, 321:522-525 (1986); Reichmann et al., *Nature*, 332:323-329 [1988]; and Presta, *Curr. Op. Struct. Biol.*, 2:593-596 (1992). The humanized antibody includes a PRIMATIZED™ antibody wherein the antigen-binding region of the antibody is derived from an antibody produced by immunizing macaque monkeys with the antigen of interest.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5× Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a Angptl3 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

The terms "biological activity" and "biologically active" with regard to the Angptl3 molecules herein refer to the ability of a molecule to specifically bind to and regulate cellular responses mediated by a native $\alpha v \beta 3$ integrin receptor, such as adhesion and/or migration of vascular endothelial cells. In this context, the term "regulate" includes both promotion and inhibition, therefore, the (native and variant) Angptl3 molecules of the present invention include agonists and antagonists of a native $\alpha v \beta 3$ integrin receptor. Preferred biological activities of the Angptl3 ligands herein include the promotion or inhibition of vascularization (angiogenesis), and in particular, involvement in the angiogenic process during liver regeneration.

The term "agonist" is used to refer to peptide and non-peptide analogs of the native Angptl3 molecules of the present invention, and to antibodies specifically binding such native Angptl3 molecules, provided that they have the ability to signal through a native Angptl3 receptor ($\alpha v \beta 3$). In other words, the term "agonist" is defined in the context of the biological role of the Angptl3 receptor ($\alpha v \beta 3$). Preferred agonists possess the preferred biological activities of a native Angptl3, as defined above, such as the promotion of vascularization (angiogenesis), for example, during liver regeneration.

The term "antagonist" is used to refer to peptide and non-peptide analogs of a native Angptl3 molecule, and to antibodies, provided that they have the ability to inhibit the biological function of Angptl3 regardless of whether they have the ability to bind Angptl3 or its receptor, $\alpha v \beta 3$. Accordingly, antagonists that have the ability to bind Angptl3 or its receptor include anti-Angptl3 and anti-$\alpha v \beta 3$ antibodies. Preferred antagonists are inhibitors of the adhesion and/or migration of vascular endothelial cells, and in particular inhibitors of angiogenesis, especially angiogenesis associated with malignant tumor growth, inflammatory diseases of the liver or cardiac diseases.

"Tumor" as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia. More particular examples of cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, vulval cancer, thyroid cancer, hepatic carcinoma and various types of head and neck cancer.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "liposome" is a small vesicle composed of various types of lipids, phospholipids and/or surfactant which is useful for delivery of a drug (such as a PRO10282 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

An "effective amount" of a Angptl3 polypeptide disclosed herein is an amount capable of triggering a desired biological response. In particular, an "effective amount" of a Angptl3 polypeptide or an agonist thereof preferably is an amount capable of regulating a cellular response mediated by an $\alpha v \beta 3$ Angptl3 receptor, such as adhesion and/or migration of endothelial cells, e.g. vascular endothelial cells. The term includes an amount capable of invoking angiogenesis, especially angiogenesis associated with liver regeneration.

A "therapeutically effective amount", in reference to the treatment of tumor, e.g. when antagonists of a native Angptl3 polypeptide are used, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, which may, but does not have to, result in the regression or rejection of the tumor; and/or (7) relief, to some extent, of one or more symptoms associated with the disorder. A "therapeutically effective amount" of a Angptl3 polypeptide antagonist for purpose of treatment of tumor may be determined empirically and in a routine manner.

"Vascular endothelial growth factor" or "VEGF" is an endothelial cell-specific mitogen which as been shown to be stimulated by hypoxia and required for tumor angiogenesis (Senger et al., *Cancer* 46:5629-5632 (1986); Kim et al., *Nature* 362:841-844 (1993); Schweiki et al., *Nature* 359: 843-845 (1992); Plate et al., *Nature* 359:845-848 (1992)). The term, as used herein, includes all VEGF isoforms, including, without limitation, the human VEGF121 and VEGF165 isoforms.

B. Non-human Mammalian Homologues of Human Angptl3

The isolation of native human Angptl3 is described in Example 1, and also in PCT Publication WO 99/15654, which is hereby expressly incorporated by reference in its entirety. Angptl3 DNA has also been deposited with the American type Culture Collection (ATCC) on Sep. 18, 1997, under the designation FLS139-DNA16451-1078, and assigned ATCC Deposit No. 209283.

In order to identify other, non-human mammalian homologues, or splice or other naturally occurring variants, libraries can be screened with probes (such as antibodies to the human Angptl3 sequence or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding other native Angptl3 polypeptides is to use PCR methodology (Sambrook et al., supra; Dieffenbach et al., *PCR Primer: A Laboratory Manual* (Cold Spring Harbor Laboratory Press, 1995)).

The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as Gen-Bank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

C. Angptl3 Variants

Native human Angptl3 is known in the art, and disclosed, for example, in PCT Publication No. WO 99/15654 published on Apr. 1, 1999. Variations in the native full-length sequence Angptl3 (SEQ ID NO: 2) or in various domains of the Angptl3 amino acid sequence described herein, can be made, for example, using any of the techniques and guidelines for conservative and non-conservative mutations set forth, for instance, in U.S. Pat. No. 5,364,934. Variations may be a substitution, deletion or insertion of one or more codons encoding the Angptl3 polypeptide that results in a change in the amino acid sequence of Angptl3 as compared with the native sequence of SEQ ID NO: 2. Optionally the variation is by substitution of at least one amino acid with any other amino acid in one or more of the domains of a native or variant Angptl3 sequence. Guidance in determining which amino acid residue may be inserted, substituted or deleted without adversely affecting the desired activity may be found by comparing the sequence of the Angptl3 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

Thus, Angptl3 polypeptide fragments are provided herein. Such fragments may be truncated at the N-terminus or C-terminus, or may lack internal residues, for example, when compared with a full-length native protein. Certain fragments lack amino acid residues that are not essential for a desired biological activity of the Angptl3 polypeptide.

The homology modeling of the fibrinogen domain of native human Angptl3 of SEQ ID NO: 2, and the functional analysis of the domains engaged in endothelial cell binding by Angptl3, as described in Example 5, are useful in designing the Angptl3 variants herein. Based on the modeled structure of the fibrinogen-like domain of Angptl3, it was found that regions P1: amino acids 281-293 (SEQ ID NO: 14); P2: amino acids 442-460 (SEQ ID NO: 15); and P3 amino acids 415-430 (SEQ ID NO: 17) of native human Angptl3 (SEQ ID NO: 2) are involved in αvβ3 binding. In order to retain receptor binding and the ability to activate and signal through the receptor, the P1, P2 and P3 regions should be substantially retained, or only conservative substitutions should be performed in these regions. On the other hand, in order to design Angptl3 antagonists, it might be necessary to make more significant amino acid alterations within one or more of these regions. Design of the Angptl3 variants is further assisted by the ribbon diagram shown in FIG. 5B, and the sequence alignment shown in FIG. 5C, where the hydrophilic and charged residues are displayed in blue, and the aromatic and hydrophobic residues are displayed in orange.

As discussed above, in particular embodiments, conservative substitutions are of interest in making Angptl3 variants of the present invention. Such conservative substitutions are shown in Table 1 under the heading of preferred substitutions. If such substitutions result in a change in biological activity, then more substantial changes, denominated exemplary substitutions in Table 1, or as further described below in reference to amino acid classes, are introduced and the products screened.

TABLE 1

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the Angptl3 variant polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:
(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis (Carter et al., *Nucl. Acids Res.*, 13:4331 (1986); Zoller et al., *Nucl. Acids Res.*, 10:6487 (1987)), cassette mutagenesis [Wells et al., *Gene*, 34:315 (1985)], restriction selection mutagenesis (Wells et al., *Philos. Trans. R. Soc. London SerA,* 317:415 (1986)) or other known techniques can be performed on the cloned DNA to produce the Angptl3 variant DNA.

Angptl3 fragments may be prepared by any of a number of conventional techniques. Desired peptide fragments may be chemically synthesized. An alternative approach involves generating Angptl3 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, Angptl3 polypeptide fragments share at least one biological and/or immunological activity with the native Angptl3 of SEQ ID NO: 2.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, *Science,* 244: 1081-1085 (1989)). Alanine is also typically preferred because it is the most common amino acid. Further, it is frequently found in both buried and exposed positions (Creighton, *The Proteins,* (W. H. Freeman & Co., N.Y.); Chothia, *J. Mol. Biol.,* 150:1 (1976)). If alanine substitution does not yield adequate amounts of variant, an isoteric amino acid can be used.

Further details of making Angptl3 variants, covalent modifications of native and variant Angptl3 polypeptides, antibodies specifically binding to Angptl3 (including variants), and immunoadhesins are provided, for example, in WO 99/15654.

D. Use of Angptl3 Polypeptides

As described in the examples below, expression analysis of Angptl3 in adult tissues demonstrated liver specific expression and strong upregulation in hepatocytes of diseases, cirrhotic liver or after toxic liver injury. Further, in vivo administration of Angptl3 resulted in a an increase in vascular permeability and a short-term protective effect from liver damage but prolonged expression of Angptl3 was associated with liver damage. Even further, Angptl3 induced angiogenesis when tested in the rat cornea assay in vivo. The robust induction of vessel growth by Angptl3 in the latter assay combined in the pronounced expression detected in disease liver specimens strongly indicate that this factor plays an important role in regulation of the angiogenic process during liver regeneration.

Accordingly, Angptl3 and Angptl3 agonists are believed to be useful in the treatment, prevention and/or identification of subjects at risk of acute liver disease and the induction of liver regeneration following acute liver injury and/or angiogenesis in a tissue. The acute liver injury may be associated with inflammatory liver disease, such as chronic, alcoholic or viral hepatitis, chemical or mechanical injury to the liver, heptatectomy which may be due to chronic hepatitis, liver cirrhosis, primary or metastatic liver cancer or gallbladder cancer. The angiogenesis in a tissue may be asociated with cardiac tissue or liver tissue that has been injured as a result of an infectious or autoimmune process, mechanical or chemical injury or cancer or metastatic cancer.

Accordingly, Angptl3 antagonists are believed to be useful in the treatment and/or prevention of tissue damage characterized by overexpression of Angptl3, a chronic liver disease, and/or a heart disease characterized by the elevated expression of Angptl3. Tissue damage characterized by overexpression of Angptl3 includes liver tissue damage associated with inflammation, without limitation inflammation associated with a chronic liver disease, the pathogenesis of which involves the activation and recruitment of inflammatory cells to the liver, regardless of whether the underlying cause is an infectious or autoimmune disease, or chemical injury to the liver, or other. Thus, liver tissue damage characterized by overexpression of Angptl3 includes liver cirrhosis, such as alcoholic liver cirrhosis and primary biliary cirrhosis (PBC), liver fibrosis, chronic hepatitis, such as chronic autoimmune hepatitis, chronic alcoholic hepatitis, and non-alcoholic steatohepatitis (NASH), viral hpatitis A, B, C, D, E and G, toxic metabolic liver damage, fatty liver, ischemia reperfusion injury of the liver and sepsis, and liver damage associated with liver tumor, without limitation hepatocellular carcinoma, extrahepatic bile duct carcinoma, cholangiocarcinoma and metastatic cancer of the liver. Heart tissue damage associated with elevated expression of Angptl3 or cardiac disease, the pathogenesis of which includes an inflammatory response, or in the development of which inflammation is a risk factor and heart tissue damage associated with elevated expression of Angptl3, without limitation coronary artery disease, cardiomyopathy, such as non-specific hypertrophy and dilated cardiomyopathy, myocarditis, congestive heart failure (CHF), and myocardial infarction. For review, see Lawson et al., *Toxicol Sci* 54:509-16 (2000), supra.

Further, Angptl3 antagonists are believed to be useful in the inhibition of an undesired increase in vascular permeability in a tissue. The tissue may be liver or cardiac tissue. The increase in vascular permeability may be an increased permeability of small vessels following tissue damage and may follow necrosis of vascular endothelium due to exposure to toxins or may be associated with inflammation, such as chronic inflammation/treatment and/or prevention of tissue damage characterized by overexpression of Angptl3, a chronic liver disease, and/or a heart disease characterized by the elevated expression of Angptl3.

Even further, Angptl3 antagonists are believed to be useful in the prevention and/or treatment of chronic alcoholic hepatitis, resulting from excessive alcohol consumption. Alcoholic hepatitis can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma.

Also encompassed by this invention are T-cell mediated diseases which affect the liver. Autoimmune damage from T cells is mediated directly by cytotoxic T cells and indirectly T helper cells. Autoimmune diseases the treatment of which is contemplated herein include, without limitation, autoimmune hepatitis and primary biliary cirrhosis. Autoimmune hepatitis (also known as autoimmune chronic active hepatitis) is a chronic disorder characterized by continuing hepatocellular necrosis and inflammation, which, if untreated, usually progresses to cirrhosis and ultimately liver failure. Primary biliary cirrhosis is an autoimmune disease of the intrahepatic or biliary system, and is associated with impaired bile secretion. It is believed that autoimmune antibodies and T cells mediate tissue damage to the liver associated with this disease.

The Angptl3 antagonists are also useful in the treatment of ischemia reperfusion injury of the liver. As discussed before, ischemia reperfusion injury occurs generally when the flow of blood to a region of the body is temporarily halted (ischemia) and then re-established (reperfusion). The injury may occur in the parts of the body to which the blood supply was interrupted, or it can occur in parts fully supplied with blood during the period of ischemia. Ischemia reperfusion injury of the liver may result from various underlying causes such as, for example, from hepatic and biliary surgical resections, and clinically is manifested by such complications as hepatic dysfunction including acute hepatocellular damage and necrosis.

Angptl3 antagonists include, without limitation, antibodies, small organic and inorganic molecules, peptides, phosphopeptides, antisense and ribozyme molecules, triple helix molecules, etc., that inhibit the expression and/or activity of the target gene product.

For example, antisense RNA and RNA molecules act to directly block the translation of mRNA by hybridizing to targeted mRNA and preventing protein translation. When antisense DNA is used, oligodeoxyribonucleotides derived from the translation initiation site, e.g., between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4:469-471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g., PCT publication No. WO 97/33551, supra.

When the Angptl3 polypeptides herein (including their agonists and antagonists) are employed as therapeutic agents, they can be formulated according to known methods to prepare pharmaceutically useful compositions, whereby the Angptl3 polypeptide is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

When in vivo administration of a Angptl3 polypeptide or agonist or antagonist thereof is employed, normal dosage amounts may vary from about 10 ng/kg to up to 100 mg/kg of mammal body weight or more per day, preferably about 1 g/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

For example, before determining the effective dosage for the treatment of any specific liver disease, the severity of the disease is determined by conventional clinical and laboratory evaluation of the patient. Benefit of the treatment is assessed by follow-up of liver function with clinical and laboratory assessment, performed in regular intervals, such as every week, two weeks or month.

Where sustained-release administration of a Angptl3 polypeptide is desired in a formulation with release characteristics suitable for the treatment of any disease or disorder requiring administration of the Angptl3 polypeptide, microencapsulation of the Angptl3 polypeptide is contemplated. Microencapsulation of recombinant proteins for sustained release has been successfully performed with human growth hormone (rhGH), interferon-γ (rhIFN-γ), interleukin-2, and MN rgp120. Johnson et al., *Nat. Med.,* 2:795-799 (1996); Yasuda, *Biomed. Ther.,* 27:1221-1223 (1993); Hora et al., *Bio/Technology,* 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

It may be desirable to combine the Angptl3 therapeutic agents with other therapeutic regimens. For example, treatment with the Angptl3 polypeptides or their agonists can be combined with the administration of other angiogenic factors, such as vascular endothelial cell growth factor (VEGF) or fibroblast growth factor (FGF).

E. Articles of Manufacture

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually an anti-tumor agent capable of interfering with the activity of a gene product identified herein, e.g., an antibody. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

F. Diagnostic Use

As Angptl3 is upregulated in inflammatory liver diseases, its overexpression relative to normal tissues can serve as a diagnostic marker of such diseases.

Gene amplification and/or expression may be measured in a sample directly, for example, by conventional Southern blotting, Northern blotting to quantitate the transcription of mRNA (Thomas, *Proc. Natl. Acad. Sci. USA,* 77:5201-5205 (1980)), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

For example, antibodies, including antibody fragments, can be used to qualitatively or quantitatively detect the expression of Angptl3 proteins. As noted above, the antibody preferably is equipped with a detectable, e.g., fluorescent label, and binding can be monitored by light microscopy, flow cytometry, fluorimetry, or other techniques known in the art. These techniques are particularly suitable, if the amplified gene encodes a cell surface protein, e.g., a growth factor. Such binding assays are performed essentially as described in section 5 above.

In situ detection of antibody binding to the Angptl3 protein can be performed, for example, by immunofluorescence or immunoelectron microscopy. For this purpose, a tissue specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

One of the most sensitive and most flexible quantitative methods for quantitating differential gene expression is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from a disease tissue and corresponding normal tissues, respectively. Thus, mRNA can be extracted, for example, from frozen or archived paraffin-embedded and fixed (e.g. formalin-fixed) samples of diseased tissue for comparison with normal tissue of the same type. Methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andrés et al., *BioTechniques* 18:42044 (1995). In particular, RNA isolation can be performed using purification kit, buffer set and protease from commercial manufacturers, such as QIAGEN, according to the manufacturer's instructions. For example, total RNA from cells in culture can be isolated using QIAGEN RNEASY mini-columns. Total RNA from tissue samples can be isolated using RNA Stat-60 (Tel-Test).

As RNA cannot serve as a template for PCR, the first step in differential gene expression analysis by RT-PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (PERKIN ELMER, CA, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' endonuclease activity. Thus, TAQMAN PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicontypical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN RT-PCR can be performed using commercially available equipments, such as, for example, ABI PRIZM 7700™ SEQUENCE DETECTION SYSTEM™ (PERKIN-ELMER-Applied Biosystems, Foster City, Calif., USA), or Lightcycler (ROCHE Molecular Biochemicals, Mannheim, Germany). In a preferred embodiment, the 5' nuclease procedure is run on a real-time quantitative PCR device such as the ABI PRIZM 7700™ SEQUENCE DETECTION SYSTEM™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle ($C_t$). The $\Delta Ct$ values are used as quantitative measurement of the relative number of starting copies of a particular target sequence in a nucleic acid sample when comparing the expression of RNA in a cell from a diseased tissue with that from a normal cell.

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

Differential gene expression can also be identified, or confirmed using the microarray technique. In this method, nucleotide sequences of interest are plated, or arrayed, on a microchip substrate. The arrayed sequences are then hybridized with specific DNA probes from cells or tissues of interest.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(20):106-49 (1996)). The methodology of hybridization of nucleic acids and microarray technology is well known in the art.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Identification of Angptl3

Angptl3 was identified in a cDNA library prepared from human fetal liver mRNA obtained from Clontech Laboratories, Inc. Palo Alto, Calif. USA, catalog no. 64018-1, following the protocol described in "Instruction Manual: Superscript® Lambda System for cDNA Synthesis and λ cloning," cat. No. 19643-014, Life Technologies, Gaithersburg, Md., USA which is herein incorporated by reference. Unless otherwise noted, all reagents were also obtained from Life Technologies. The overall procedure can be summarized into the following steps: (1) First strand synthesis; (2) Second strand synthesis; (3) Adaptor addition; (4) Enzymatic digestion; (5) Gel isolation of cDNA; (6) Ligation into vector; and (7) Transformation.

First Strand Synthesis:

Not1 primer-adapter (Life Tech., 2 µl, 0.5 µg/µl) was added to a sterile 1.5 ml microcentrifuge tube to which was added poly A+ mRNA (7 µl, 5 µg). The reaction tube was heated to 70° C. for 5 minutes or time sufficient to denature the secondary structure of the mRNA. The reaction was then chilled on ice and 5×First strand buffer (Life Tech., 4 µl), 0.1 M DTT (2 µl) and 10 mM dNTP Mix (Life Tech., 1 µl) were added and then heated to 37° C. for 2 minutes to equilibrate the temperature. SUPERSCRIPT II® reverse transcriptase (Life Tech., 5 µl) was then added, the reaction tube mixed well and incubated at 37° C. for 1 hour, and terminated by placement on ice. The final concentration of the reactants was the following: 50 mM Tris-HCl (pH 8.3); 75 mM KCl; 3 mM $MgCl_2$; 10 mM DTT; 500 µM each dATP, dCTP, dGTP and dTTP; 50 µg/ml Not 1 primer-adapter; 5 µg (250 µg/ml) mRNA; 50,000 U/ml SUPERSCRIPT II® reverse transcriptase.

Second Strand Synthesis:

While on ice, the following reagents were added to the reaction tube from the first strand synthesis, the reaction well mixed and allowed to react at 16° C. for 2 hours, taking care not to allow the temperature to go above 16° C.: distilled water (93 µl); 5×Second strand buffer (30 µl); dNTP mix (3 µl); 10 U/µl *E. Coli* DNA ligase (1 µl); 10 U/µl *E. Coli* DNA polymerase I (4 µl); 2 U/µl *E. Coli* RNase H (1 µl). 10 U T4 DNA Polymerase (2 µl) was added and the reaction continued to incubate at 16° C. for another 5 minutes. The final concentration of the reaction was the following: 25 mM Tris-HCl (pH 7.5); 100 mM KCl; 5 mM $MgCl_2$; 10 mM $(NH_4)_2SO_4$; 0.15 mM β-NAD+; 250 µM each dATP, dCTP, dGTP, dTTP; 1.2 mM DTT; 65 U/ml DNA ligase; 250 U/ml DNA polymerase I; 13 U/ml Rnase H. The reaction has halted by placement on ice and by addition of 0.5 M EDTA (10 µl), then extracted through phenol:chloroform:isoamyl alcohol (25:24:1, 150 µl). The aqueous phase was removed, collected and diluted into 5M NaCl (15 µl) and absolute ethanol (−20° C., 400 µl) and centrifuged for 2 minutes at 14,000×g. The supernatant was carefully removed from the resulting DNA pellet, the pellet resuspended in 70% ethanol (0.5 ml) and centrifuged again for 2 minutes at 14,000×g. The supernatant was again removed and the pellet dried in a speedvac.

Adapter Addition

The following reagents were added to the cDNA pellet from the second strand synthesis above, and the reaction was gently mixed and incubated at 16° C. for 16 hours: distilled water (25 µl); 5×T4 DNA ligase buffer (10 µl); Sal 1 adapters (10 µl); T4 DNA ligase (5 µl). The final composition of the reaction was the following: 50 mM Tris-HCl (pH 7.6); 10 mM $MgCl_2$; 1 mM ATP; 5% (w/v) PEG 8000; 1 mM DTT; 200 µg/ml Sal 1 adapters; 100 U/ml T4 DNA ligase. The reaction was extracted through phenol:chloroform:isoamyl alcohol (25:24:1, 50 µl), the aqueous phase removed, collected and diluted into 5M NaCl (8 µl) and absolute ethanol (−20° C., 250 µl). This was then centrifuged for 20 minutes at 14,000×g, the supernatant removed and the pellet was resuspended in 0.5 ml 70% ethanol, and centrifuged again for 2 minutes at 14,000×g. Subsequently, the supernatant was removed and the resulting pellet dried in a speedvac and carried on into the next procedure.

Enzymatic Digestion;

To the cDNA prepared with the Sal 1 adapter from the previous paragraph was added the following reagents and the mixture was incubated at 37° C. for 2 hours: DEPC-treated water (41 µl); Not 1 restriction buffer (REACT, Life Tech., 5 µl), Not 1 (4 µl). The final composition of this reaction was the following: 50 mM Tris-HCl (pH 8.0); 10 mM $MgCl_2$; 100 mM MaCl; 1,200 U/ml Not 1.

Gel Isolation of cDNA:

The cDNA is size fractionated by acrylamide gel electrophoresis on a 5% acrylamide gel, and any fragments which were larger than 1 Kb, as determined by comparison with a molecular weight marker, were excised from the gel. The cDNA was then electroeluted from the gel into 0.1×TBE buffer (200 µl) and extracted with phenol:chloroform:isoamyl alcohol (25:24:1, 200 µl). The aqueous phase was removed, collected and centrifuged for 20 minutes at 14,000×g. The supernatant was removed from the DNA pellet which was resuspended in 70% ethanol (0.5 ml) and centrifuged again for 2 minutes at 14,000×g. The supernatant was again discarded, the pellet dried in a speedvac and resuspended in distilled water (15 µl).

Ligation of cDNA into pRK5 Vector:

The following reagents were added together and incubated at 16° C. for 16 hours: 5×T4 ligase buffer (3 µl); pRK5, XhoI, NotI digested vector, 0.5 µg, 1 µl); cDNA prepared from previous paragraph (5 µl) and distilled water (6 µl). Subsequently, additional distilled water (70 µl) and 10 mg/ml tRNA (0.1 µl) were added and the entire reaction was extracted through phenol:chloroform:isoamyl alcohol (25:

24:1). The aqueous phase was removed, collected and diluted into SM NaCl (10 µl) and absolute ethanol (−20° C., 250 µl). This was then centrifuged for 20 minutes at 14,000× g, decanted, and the pellet resuspended into 70% ethanol (0.5 ml) and centrifuged again for 2 minutes at 14,000×g. The DNA pellet was then dried in a Speedvac and eluted into distilled water (3 µl) for use in the subsequent procedure.

Transformation of Library Ligation into Bacteria:

The ligated cDNA/pRK5 vector DNA prepared previously was chilled on ice to which was added electrocompetent DH10B bacteria (Life Tech., 20 µl). The bacteria vector mixture was then electroporated as per the manufacturers recommendation. Subsequently SOC media (1 ml) was added and the mixture was incubated at 37° C. for 30 minutes. The transformants were then plated onto 20 standard 150 mm LB plates containing ampicillin and incubated for 16 hours (37° C.) to allow the colonies to grow. Positive colonies were then scraped off and the DNA isolated from the bacterial pellet using standard CsCl-gradient protocols. For example, Ausubel et al., 2.3.1.

Identification of Angptl3

Angptl3 can be identified in the human fetal liver library by any standard method known in the art, including the methods reported by Klein R. D. et al. (1996), *Proc. Natl. Acad. Sci.* 93, 7108-7113 and Jacobs (U.S. Pat. No. 5,563,637 issued Jul. 16, 1996). According to Klein et al. and Jacobs, cDNAs encoding novel secreted and membrane-bound mammalian proteins are identified by detecting their secretory leader sequences using the yeast invertase gene as a reporter system. The enzyme invertase catalyzes the breakdown of sucrose to glucose and fructose as well as the breakdown of raffinose to sucrose and melibiose. The secreted form of invertase is required for the utilization of sucrose by yeast (*Saccharomyces cerevisiae*) so that yeast cells that are unable to produce secreted invertase grow poorly on media containing sucrose as the sole carbon and energy source. Both Klein R. D., supra, and Jacobs, supra, take advantage of the known ability of mammalian signal sequences to functionally replace the native signal sequence of yeast invertase. A mammalian cDNA library is ligated to a DNA encoding a nonsecreted yeast invertase, the ligated DNA is isolated and transformed into yeast cells that do not contain an invertase gene. Recombinants containing the nonsecreted yeast invertase gene ligated to a mammalian signal sequence are identified based upon their ability to grow on a medium containing only sucrose or only raffinose as the carbon source. The mammalian signal sequences identified are then used to screen a second, full-length cDNA library to isolate the full-length clones encoding the corresponding secreted proteins. Cloning may, for example, be performed by expression cloning or by any other technique known in the art.

The primers used for the identification of Angptl3 are as follows:

in FIGS. 2A and 2B (SEQ. ID. NO: 2). Angptl3 contains a fibrinogen-like domain (FIG. 3A, and FIGS. 5A-C) that exhibits a high degree of sequence homology with the two known human ligands of the TIE-2 receptor (h-TIE2L1 and h-TIE2L2) and human angiopoietins 1, 2 and 4 (ANG1, ANG2, ANG4, FIG. 5C).

A clone of Angptl3 was deposited with the American Type Culture Collection (ATCC), 12301 Parklawn Drive, Rockville, Md. 20852, on Sep. 18, 1997, under the terms of the Budapest Treaty, and has been assigned the deposit number ATCC 209281.

Example 2

Expression of Angptl3

Human Angptl3 was cloned into the eukaryotic expression vector pRK5tkNEO and the baculovirus vector pHIF, a derivative of pVL1393 purchased from PHARMINGEN, CA. Plasmid DNA was cotransfected with BACULOGOLD™ DNA (PHARMINGEN, CA) into *Spodoptera frugiperda* ("Sf9") cells (ATCC CRL 1711) using Lipofectin (GIBCO-BRL, MD). After 4 days, the cells were harvested, 500 µl of the supernatant was used to infect $2 \times 10^6$ Sf9 cells and baculovirus was amplified. After 72 hours of amplification the cells were harvested and 10 ml of the supernatant used to infect $7.5 \times 10^5$ H5 cells/ml for 40 hours. After harvesting and filtration through a 0.45 µm cellulose acetate filter, the supernatant was purified. Mouse Angptl3 was overexpressed in Chinese Hamster Ovary (CHO) cells in large scale transient transfection experiments. Human Angptl3 was purified from the supernatants of baculovirus-infected insect cells grown in suspension utilizing immunoaffinity chromatography. The column was generated by coupling anti-gD Fab to glycophase-CPG (controlled pore glass). The clarified (1000×g 5 min then 0.2 µm filtered) medium was loaded overnight at 4° C. The column was washed with PBS until the absorbance at 280 nm of the effluent returned to baseline and eluted with 50 mM Na Citrate at pH 3.0. The eluted protein was dialyzed (Spectrapore; MWCO 10,000) against 1 mM HCl and frozen at −70° C. Transiently expressed CHO cultures containing mouse Angptl3 were clarified and concentrated using a 10,000 MWCO membrane (Amicon). This volume was passed over an anti-gD Fab coupled to glycophase-CPG column as previously described for human Angptl3. The eluted pool was diluted with 10 mM Na Acetate (pH 5.0) to a conductivity of <5 mS and loaded on to S Sepharose Fast Flow (Amersham Pharmacia Biotech, NJ). The column was washed with 10 mM Na Acetate pH 5.0 until the absorbance of the effluent at 280 nm returned to baseline and eluted with a 20 column volume gradient 0-0.5 M NaCl in 10 mM Na Acetate pH 5.0. The fractions that eluted at 0.45 M-0.5 M NaCl, containing mouse Angptl3, were further purified utilizing reverse phase C-4 chromatography (Vydac, Calif.).

```
OLI114  CCACGTTGGCTTGAAATTGA                                           (SEQ ID NO: 3)

OLI115  CCTCCAGAATTGATCAAGACAATTCATGATTTGATTCTCTATCTCCAGAG             (SEQ ID NO: 4)

OLI116  TCGTCTAACATAGCAAATC                                            (SEQ ID NO:5)
```

The nucleotide sequence of Angptl3 is shown in FIG. 1 (SEQ. ID. NO: 1), while its amino acid sequence is shown The fractions were acidified with 0.1% Trifluoroacetic acid gradient. The mouse mAngptl3 eluted at 67% acetonitrile, was lyophilized and stored at −70° C. The identified of the purified proteins were verified by N-terminal sequence analysis. The LPS concentration was verified using commercial kits and determine to be <5 Eu/ml for all human or murine Angptl3 preparations.

Example 3

Preparation of Antibodies that Bind Angptl3

This example illustrates preparation of monoclonal antibodies which can specifically bind Angptl3.

Techniques for producing the monoclonal antibodies are known in the art and are described, for example, in Goding, supra. Immunogens that may be employed include purified ligand homologues of the present invention, fusion proteins containing such ligand homologues, and cells expressing recombinant ligand homologues on the cell surface. Selection of the immunogen can be made by the skilled artisan without undue experimentation.

Mice, such as Balb/c, are immunized with the immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind food pads. The immunized mice are then boosted 10 to 12 days later with additional immunogen emulsified in the selected adjuvant. Thereafter, for several weeks, the mice might also be boosted with additional immunization injections. Serum samples may be periodically obtained from the mice by retro-orbital bleeding for testing ELISA assays to detect the antibodies.

After a suitable antibody titer has been detected, the animals "positive" for antibodies can be injected with a final intravenous injection of the given ligand. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against the antigen. Determination of "positive" hybridoma cells secreting the desired monoclonal antibodies against the TIE ligand homologues herein is well within the skill in the art.

The positive hybridoma cells can be injected intraperitoneal into syngeneic Balb/c mice to produce ascites containing the anti-TIE-ligand monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 4

Endothelial Cell Binding

Angiopoietins are secreted factors that regulate angiogenesis by binding to the endothelial cell specific tyrosine kinase receptor Tie2 via their N-terminal fibrinogen (FBN)-like domain. The C-terminal coiled-coil domain present in this family of secreted ligands was found to be necessary for ligand oligomerization (Procopio et al., *J. Biol. Chem.* 274:30196-201 (1999)).

Similar to the angiopoietins, Angptl3 is a secreted glycoprotein consisting of an N-terminal signal peptide, followed by a coiled-coil domain and a C-terminal FBN-like domain (FIG. 3A).

Figure 3B:
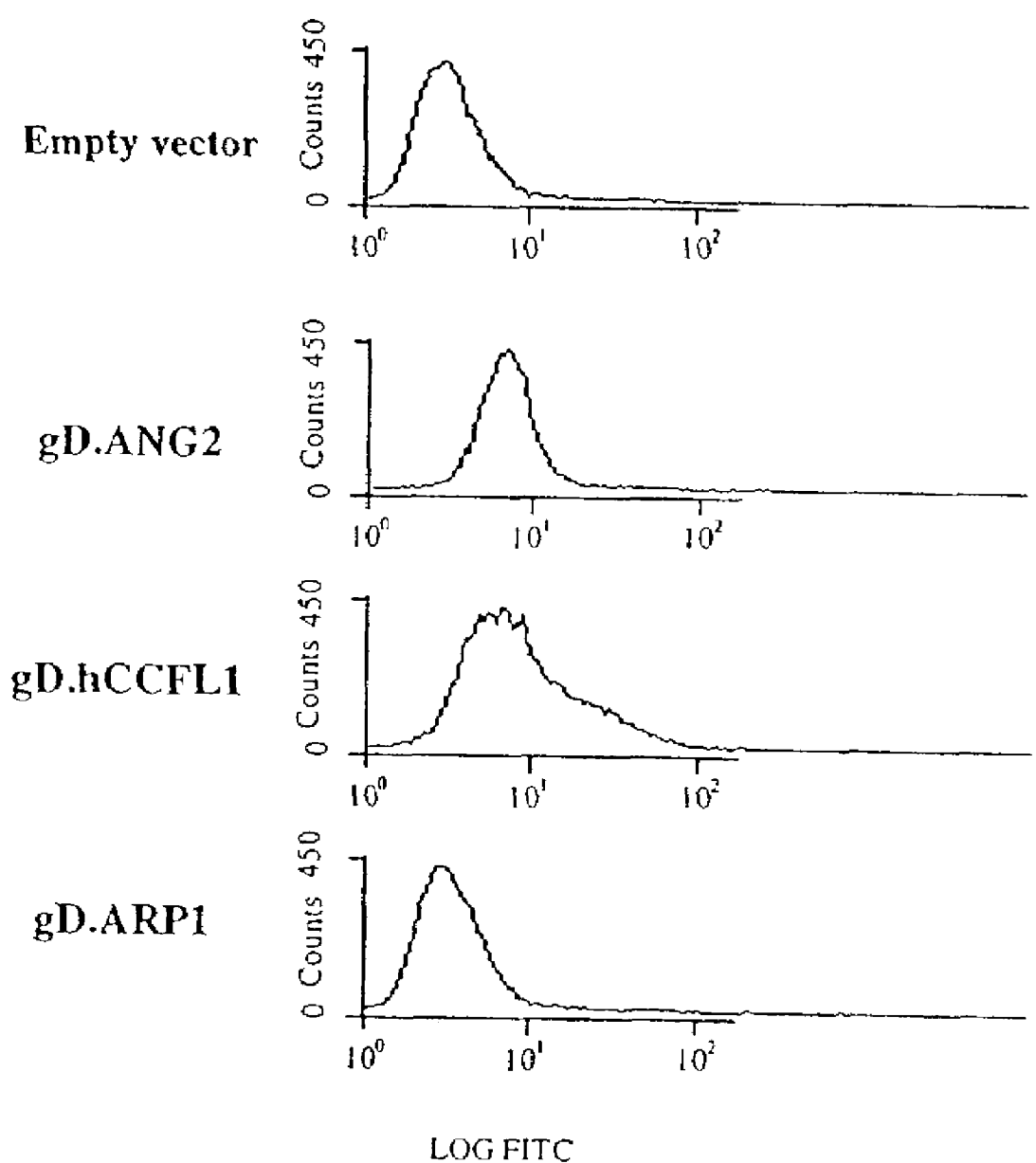
FIG. 3B shows the result of FACS analysis of HMVEC cell incubated with conditioned medium containing gD-epitope tagged version of human ANG2, ARP1, Angptl3 or control medium.

Because of the structural similarities between Angptl3 and angiopoietins, Angptl3 was tested for the ability to bind, in culture, to primary endothelial cells expressing the Tie2 receptor. Human microvascular endothelial cells (HMVECs), purchased from Cell System (Kirkland, Wash.), maintained in CS-C complete medium containing 10% fetal bovine serum and mitogens according to the recommendations by the supplier, were incubated with conditioned media from transiently transfected 293 cells expressing epitope (gD)-tagged versions of Tie2 ligands angiopoietin 1 and 2 (Ang1 and Ang2), Angptl3, and angiopoietin related protein 1 (ARP1), respectively. ARP1 is a structurally related molecule, consisting of a coiled-coil and a fibrinogen-like domain but unable to bind Tie2, and was used as a negative control. As shown in FIG. 3B, Ang2 and Angptl3 strongly bound to HMVEC under conditions where no binding was observed for ARP1. These findings demonstrated that the binding of Angptl3 to endothelial cells was specific and implied the presence of receptors on endothelial cells that mediate binding of Angptl3.

Figure 4:
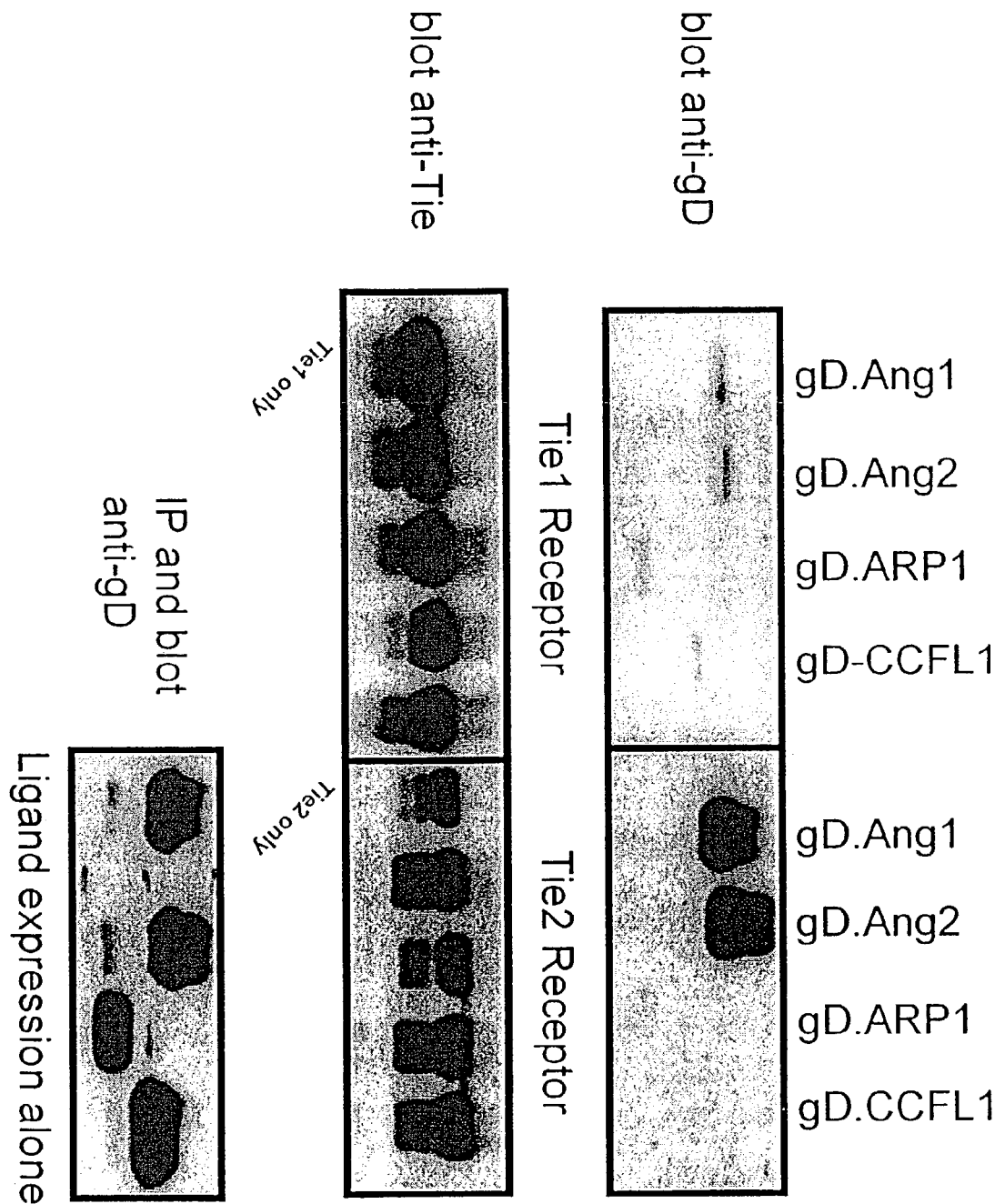
FIG. 4 shows the result of co-immunoprecipitation experiments using 293 cells cotransfected with plasmids encoding gD-tagged version of ANG1, ANG2, ARP1, Angptl3 and Tie1 receptor or Tie2 receptor, respectively. Supernatants were immunoprecipitated with antibodies against Tie1 or Tie2 and proteins resolved by SDS-PAGE and blotted to PVDF membrane were incubated with antibodies against the gD tag or the Tie receptors, respectively.

To test whether Tie2, the receptor for angiopoietins 1, 2 and 3 (Ang1, Ang2, and Ang3), or Tie1, an orphan receptor with high sequence homology to Tie2, bind to Angptl3, immunoprecipitation experiments were conducted using 293 cells transiently with expression vectors for epitope (gD)-tagged versions of Ang1 and Ang2, Angptl3 and ARP1 in conjunction with full length receptor constructs for Tie1 and Tie2, respectively. Whole cell extracts were prepared by lysis in RIPA buffer (1×PBS; 1% NP40; 0.5% sodium deoxycholate; 0.1% SDS; PMSF, 100 µg/ml; Aprotinin, 30 µl/ml; sodium orthovanadate, 1 µM) containing freshly added protease inhibitors. Extract was incubated with antibodies specific for Tie1 or Tie2 (Santa Cruz Biotechnology, San Diego, Calif.) and the resulting immunoprecipitate was analyzed by SDS-PAGE and immunoblotting. Specifically, proteins resolved by SDS-PAGE and blotted to PVDF membrane were incubated with antibodies against the gD tag or the Tie receptors, respectively. As shown in FIG. 4, Tie1 and Tie2 did not bind Angptl3 in experimental conditions that allowed Tie2 binding to Ang1 and Ang2. These findings demonstrated that Angptl3 is neither a ligand for Tie2 nor Tie1 and suggested the presence of other receptors on endothelial cells mediating the strong binding observed in the cell binding experiments.

Interestingly, exposure of cells to hypoxia or VEGF, mimicking "tumor-like" conditions, significantly increased the binding of Angptl3 (data not shown). These conditions were previously found to induce integrin expression on endothelial cells (Suzuma et al., *Invest. Ophthalmol. Vis. Sci.* 39:1028-35 (1999)), whereas Tie1 and Tie2 receptor levels were not found to be altered (Mandriota and Pepper, *Circ. Res.* 83:852-9 (1998) and Oh et al., *J. Biol. Chem.* 274: 15732-9 (1999)).

Example 5

Molecular Modeling of FBN-Angptl3

The FBN-like domain of Angptl3 shares a 39.6% sequence identity with the C terminus of the γ chain of human fibrinogen. To investigate the biological function and molecular mechanisms by which Angptl3 binds to endothelial cells, a model of the FBN-like domain of Angptl3 was built by using structural information provided by X-ray crystallographic studies on FBN domains and homology modeling techniques. The FBN domain has a unique fold consisting of three well defined domains: an N terminus domain formed by a two stranded antiparallel β-sheet flanked by a short helix; a central domain formed by a five-stranded antiparallel β-sheet with two short helices and a hairpin loop aligned against one of its faces; and a third domain which is composed predominantly of loops (FIG. 5B).

To build the FBN-Angptl3 model, a sequence-structure alignment between the FBN-Angptl3 sequence and several FBN domain structures was performed by using clustalW (Thompson et al., *Nucleic Acids Res.*, 22:4673-80 (1994)) and threading (ProCeryon Biosciences Inc.) From this alignment 3FB (PDB code) was chosen as template structure for model construction. The program PROCHECK (Laskowski et al., *J. Biomol. NMR* 8:477-86 (1996)) was used to assess the geometric quality of the model which was above average stereochemical quality when compared with the reference database of structures deposited in the PDB. The final FBN-Angptl3 model had an r.m.s.d of 1.95 Å for all $C_\alpha$ atoms when compared with the template. The overall fold of the FBN domain is conserved in FBN-Angptl3, with some differences in the loop regions at amino acid positions 220-224, 289-306, and 357-363 (FIGS. 5A and B).

Studies on the human fibrinogen gamma chain led to the identification of two regions involved in binding to the integrin αMβ2, an integrin predominantly expressed on leukocytes (Ugarova et al., *J. Biol. Chem.* 273:22519-27 (1998)). Both regions, separated in terms of linear amino acid sequence, form two adjacent antiparallel β-strands in the three-dimensional structure of the FBN domain (P1, residues 190-202; P2, residues 377-395). A different region within the fibrinogen gamma chain (P3, 346-358) and tenasin-C has also been found to be involved in binding to integrin αvβ3 (Yokoyama et al., *J. Biol. Chem.* 275:16891-8 (2000)). The present FBN-Angptl3 model and the FBN domain of the human fibrinogen gamma chain shares a high degree of structural similarity in those regions (P1: 38-50; P2: 199-214; P3: 346-361) (FIG. 5A), where the numbering follows the numbering of 3FIB (PDB code). Following the amino acid numbering of Angptl3 (SEQ ID NO: 2), P1 corresponds to amino acids 281-293 (SEQ ID NO: 14); P2 corresponds to amino acids 442-460 (SEQ ID NO: 15); and P3 corresponds to amino acids 415-430 (SEQ ID NO: 17) in the mature protein amino acid sequence.

In order to test the hypothesis whether the regions within the FBN-like domain of Angptl3 were responsible for binding, several peptides were designed and synthesized (Table 2). The P3 sequences encode regions with most structural diversity between the different domains and therefore might determine receptor specificity. Several scrambled and inverted peptides derived from the same regions were used as control peptides (Table 2). Recombinant human Angptl3 protein tagged with an amino-terminal gD epitope was generated by using a baculovirus expression system as described in Example 2 (FIG. 6A).

The glycosylation status of the recombinant Angptl3 was determined with PNGase-F treatment according to the manufacturer's instructions (New England Biolabs, MA). Purified protein (50 ng) was electrophoresed through SDS polyacrylamide gel (10% Tris-Glycine, Invitrogen, CA) and electrotransferred to nitrocellulose membranes (Invitrogen, CA) using standard procedures. The membrane was blocked by incubation in 5% w/v instant nonfat milk powder in PBS and incubated overnights at 4° C. with 1 µg/ml monoclonal anti-gD (clone 5B6.K6) antibody in blocking buffer. The membranes were washed with PBS/0.05% Tween 20 and subsequently incubated with horseradish peroxidase-coupled donkey anti-mouse antibodies (Jackson ImmunoResearch Laboratories, PA) for one hour at room temperature. Angptl3 protein was visualized by chemiluminescent detection according to the manufacturer's protocol (Amersham Pharmacia Biotech, NJ). Immunoprecipitation, transient transfections and FACS analysis were conducted as previously described (Klein et al., *Nature* 387:717-21 (1997)).

Figure 7A:
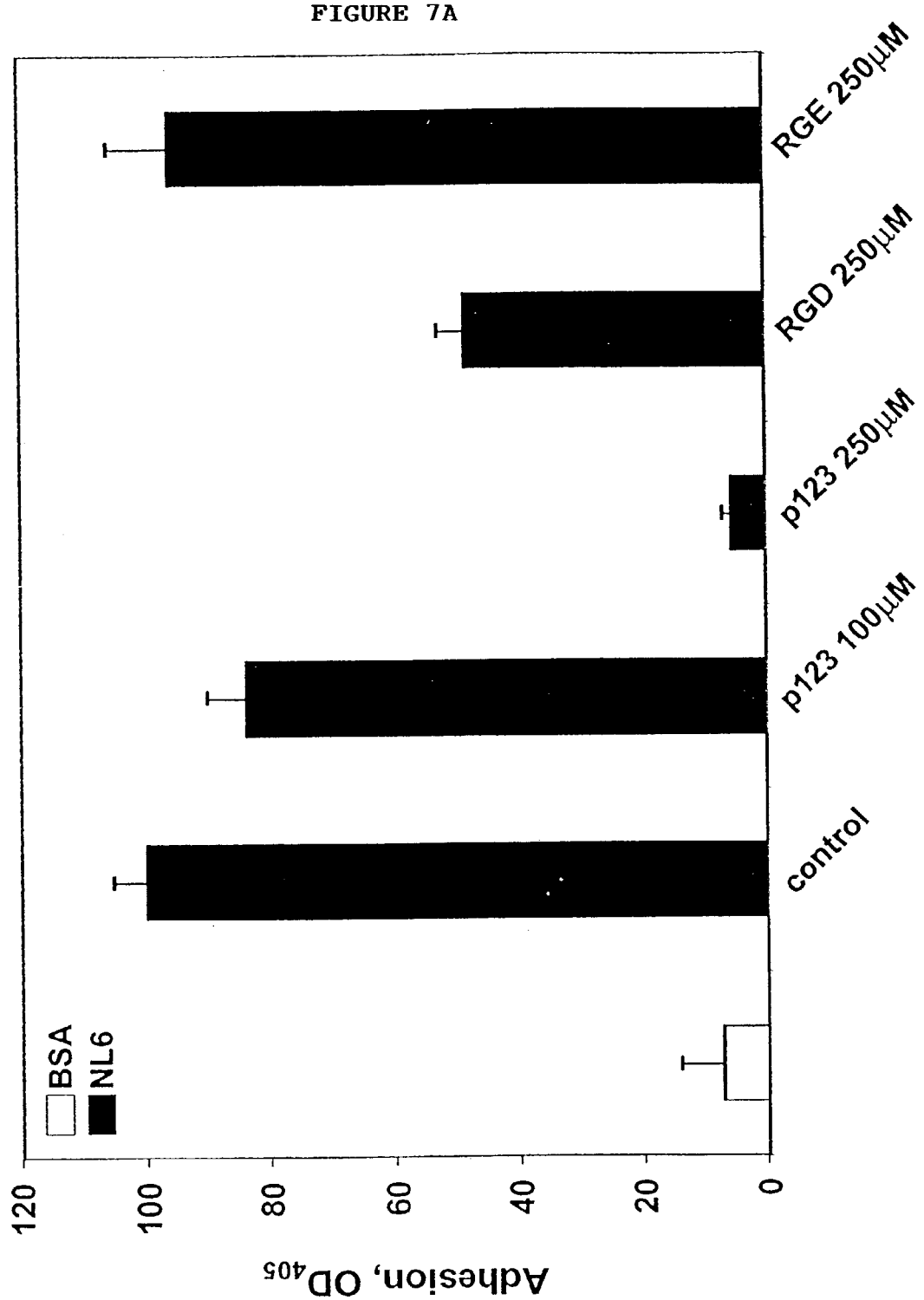
FIGS. 7A-E present functional analysis of the domains engaged in endothelial cell binding by Angptl3 and identification of αvβ3-integrin as mediator of biological responses. (A) HMVEC adhesion was tested after preincubation with combinations of the peptides p1, p2 and p3 (100 μM or 250 μM total), control (NL6-PP2-scr, 250 μM) or RGD or RGE peptides (250 μM) prior to stimulation with 200 nM MA for 4 hours. Adhesion in the presence of 200 nM PMA and in the absence of peptides was assigned a value of 100%. (B) Adhesion of 293 cells overexpressing either integrin αIIbβ3, αvβ3, αvβ1, or αvβ5 was tested in microtiter plates coated with 20 μg/ml hAngptl3 or BSA. Cells were allowed to adhere at 37° C. and quantitated after 4 hours. (C) 96-well plates were coated with increasing amounts of hAngptl3 at 4° C. overnights, unspecific binding was blocked by 3% BSA at 37° C. for one hour and wells were washed with PBS before HMVEC cells were plated. The data shown are means and SD of three separate experiments. (D) HMVEC were preincubated with or without 25 mg/ml blocking antibodies anti-α5β1 (JBS5), anti-αvβ3 (LM609), or anti-αvβ5 (PIF6) prior to stimulation with 200 nM PMA. As negative control, adhesion was carried out in the presence of 10 mM EDTA. (E) Migration of nonstimulated or hAngptl3 stimulated (50 μg/ml) HMCECs in the presence or absence of 25 μg/ml blocking antibodies anti-αvβ3 (LM609), or anti-αvβ5 (P1F6) for 16 hours.

The decrease in mobility of the Angptl3 band upon incubation with PNGase indicated that the recombinant protein was glycosylated (FIG. 6C). Similar observations were made previously for the angiopoietins. As demonstrated in FIG. 7A, addition of all three peptides to the adhesion assay completely blocked binding of endothelial cells to Angptl3. Integrin αvβ3 is capable of recognizing some of its ligands in the context of the RGD adhesive sequence. In support of our observation that the fibrinogen-like domain of Angptl3 does not encode such RGD sequence, addition of RGD peptides only partially abolished HMVEC adhesion, whereas RGE-peptides had no effect. This result suggested that only a part of the Angptl3 interaction with αvβ3 is mediated in an RGD-dependent manner. In conclusion, these data suggest that all three regions within the FBN-like domain of Angptl3 are part of the receptor binding site.

TABLE 2

| Name | Sequence | SEQ ID NO |
|---|---|---|
| NL6_P1* | PWTLIQHRIDGSQ | 14 |
| NL6_PP1 | PWTLIQHRIDGSQ | 14 |
| NL6_P2* | YSIKSTKMLIHPTDSESFE | 15 |
| NL6_PP2 | YSIKSTKMLIHPTDSES | 16 |
| NL6_P3* | GKYNKPRAKSKPERRR | 17 |
| NL6_PP3 | GKYNKPRAKSKPER | 18 |
| NL6_P32 | GKYNKPRAKSKPE | 19 |

| Control peptide name | Sequence | SEQ ID NO |
|---|---|---|
| NL6_PP1_inv | QSGDIRHQILTWP | 20 |
| NL6_PP1_src | PQWSTGLDIIQRH | 21 |
| NE_PP2_inv | SESDTPHILMKTSKISY | 22 |
| NL_PP2_src | YSSEISKDSTTPKHMIL | 23 |
| NL6_PP3_inv | REPKSKARPKNYKG | 24 |
| NL6_PP3_src | GRKEYPNKKSPKRA | 25 |
| FBG_P1 | GWTVFQKRLDGSV | 26 |
| FBG_P2 | YSMKKTTMKIIPFNRL | 10 |
| FBG_P3 | GVYYQGGTYSKAS | 12 |

Example 6

Cell Adhesion Assays

A. Identification of Integrin Mediating Angptl3 Cell Adhesion

In order to identify potential integrins binding to Angptl3, recombinant Angptl3 proteins were coated onto 96-well flat-bottomed microtiter plates (MaxiSorp, Nunc, Denmark) overnight at 4° C. and blocked with 100 µg/ml BSA in PBS for 1 hour at 37° C. Various 293 cell lines stably transfected with different integrin heterodimers, including IIbIIa ($α_{IIb}β3$), αvβ3, αvβ1 and αvβ5, were tested for their ability to bind Angptl3 coated plates. Cells were harvested and diluted to $10^5$ cells/ml in serum-free CS-C medium containing 1% BSA, 1 mM $CaCl_2$ and 1 mM $MgCl_2$. Cells were preincubated with or without blocking antibodies or peptides for 15 minutes at 37° C. and then stimulated with 200 nM PMA. Cell suspensions ($10^4$ cells/well) were added to the coated wells and the plates were incubated at 37° C. for selected times. Non-adherent cells were removed by PBS washes and cell attachment was measured using the PNAG method of Lanndegren (Landegren, U., *J. Immunol. Methods,* 67:379-388 (1984)). Results are expressed at mean $OD_{405}$ values of triplicate wells.

Figure 7B:
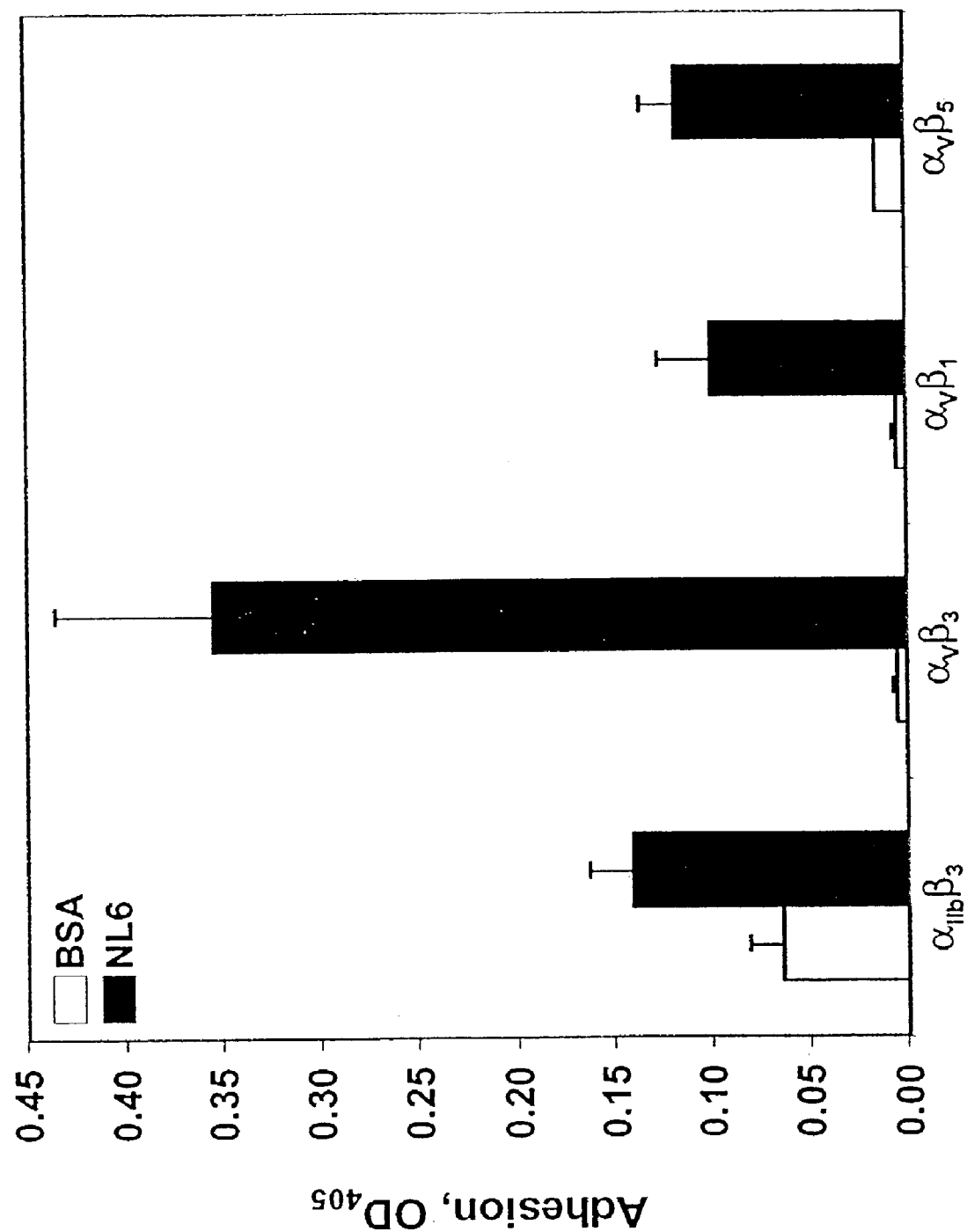

Among the stable cell lines tested, cells expressing αvβ3 displayed a marked increased in adherence to Angptl3 compared to other cell lines (FIG. 7B). Hence, these findings demonstrate that recombinant human Angptl3 binds specifically to the αvβ3 integrin. This is in agreement with the earlier observations that endothelial cells exposed to hypoxia and VEGF bound more effectively to Angptl3.

B. Mediation of Angptl3 Cell Adhesion by αvβ3

Figure 7C:
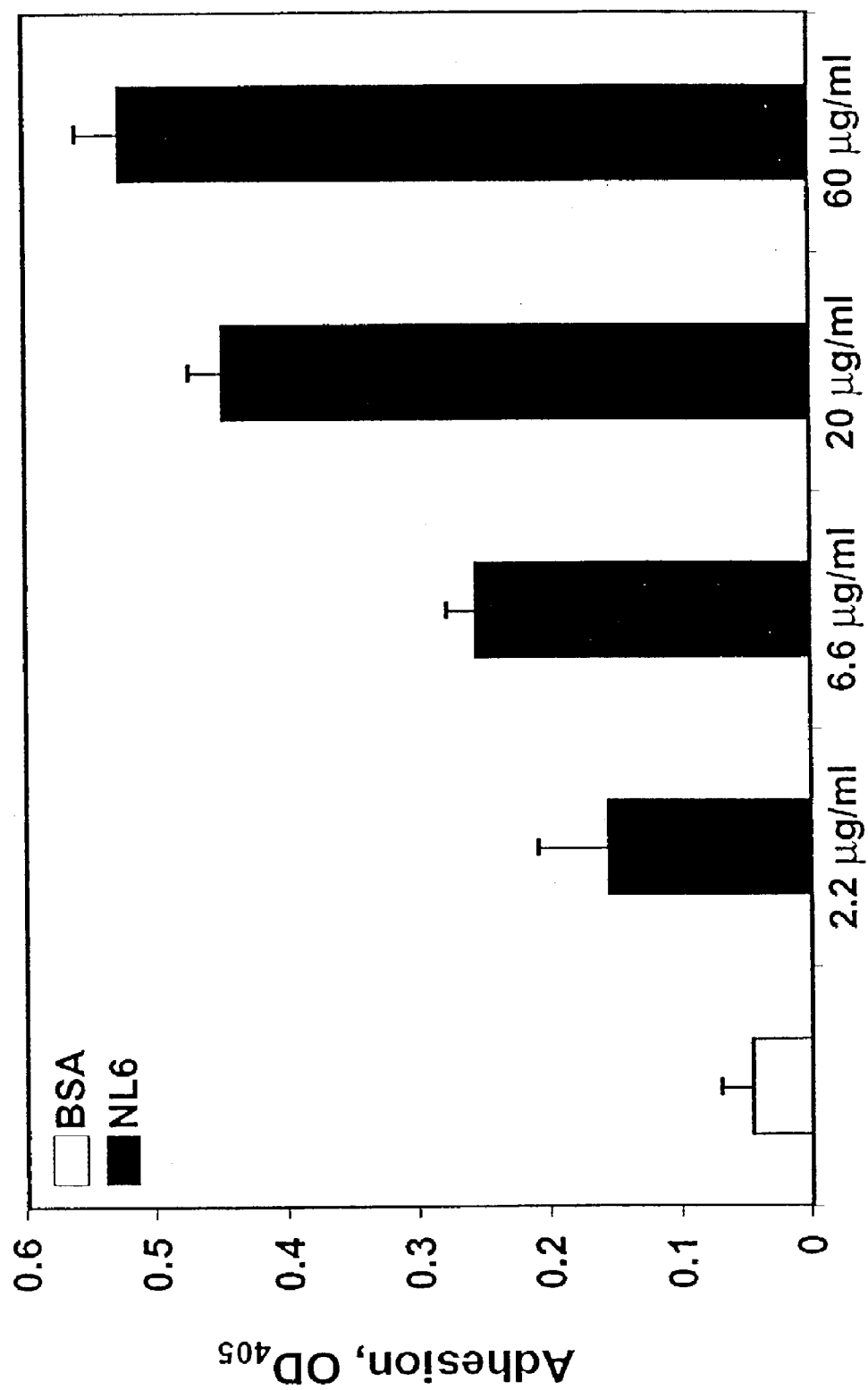

Integrins are known to induce biological responses, such as cell adhesion and migration, upon activation by their ligands. Experiments were designed to test whether Angptl3 exerts such effects on primary human endothelial cells, and whether αvβ3 was sufficient to mediate these responses. When tested in the endothelial cell adhesion assay, Angptl3 induced a robust, dose-dependent adhesion within 4 hours after incubation (FIG. 7C). The levels observed were comparable to the levels obtained when cells were plated on vitronectin, the prototypic ligand for αvβ3 (data not shown).

Figure 7D:
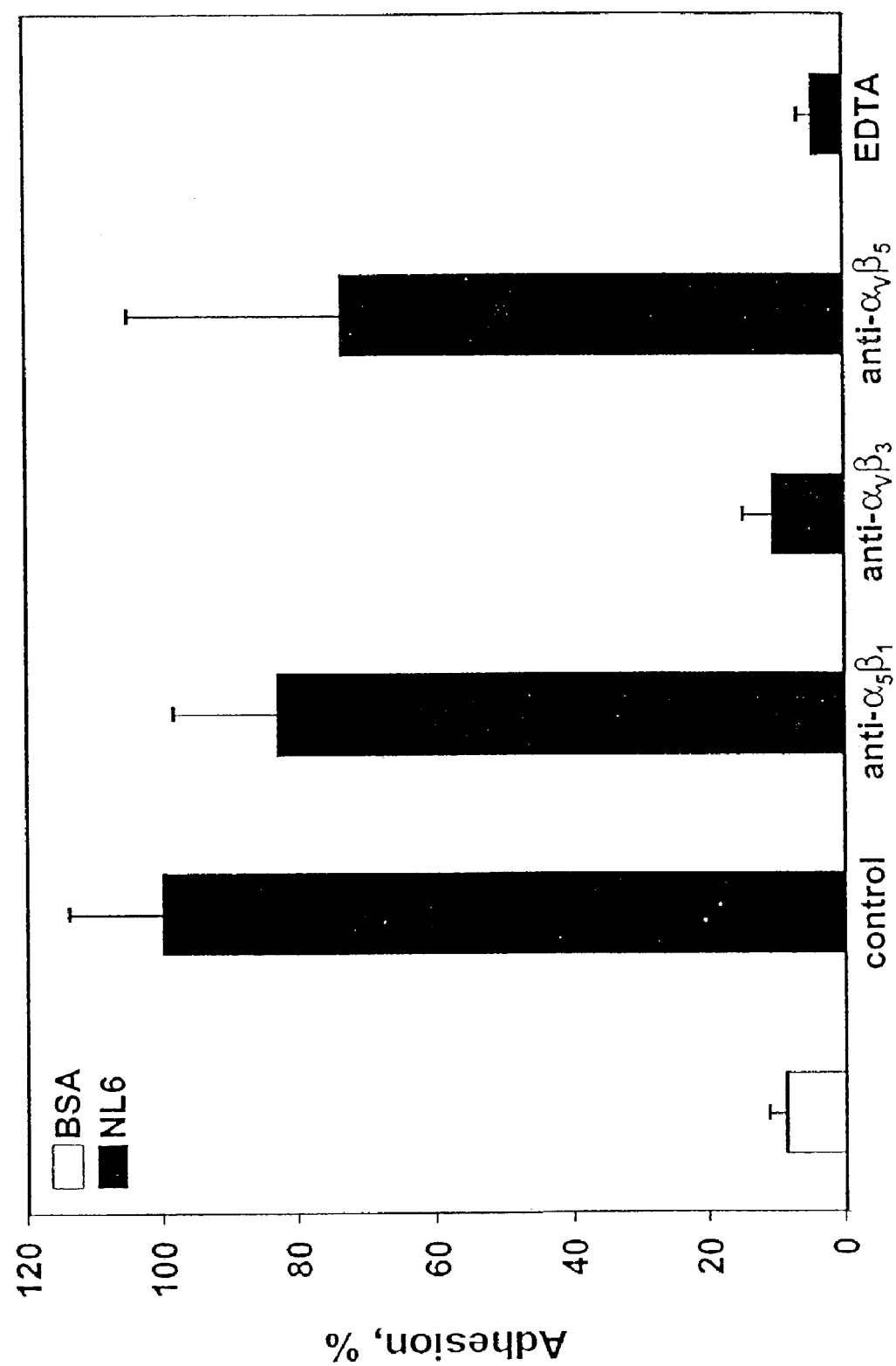

To determine whether the αvβ3 integrin was sufficient to mediate Angptl3 cell adhesion, blocking antibodies or inhibitory peptides were tested for their ability to inhibit the adhesion in the cell adhesion assay. Function blocking antibodies were added to the endothelial cells prior to incubation with the Angptl3-coated wells. The presence of function blocking antibodies to α5β1 or αvβ5 did not impair adhesion of HMVECs to culture dishes coated with Angptl3 (20 µg/ml), however, the αvβ3 specific antibody completely blocked adhesion (FIG. 7D). As a general control, EDTA (10 mM) which abrogates integrin binding to their ligands, was added to the binding experiment. As shown in FIG. 7D, the interference with the integrin dependence on divalent cations completely abolished endothelial cell adhesion.

Example 7

Cell Migration Assay

Since another hallmark of integrin activity on endothelial cells is their migratory responses to ligand stimulation, a migration assay was developed to allow study of the effects of Angptl3 on the induction of migration of endothelial cells.

Angptl3 was tested in the migration assay, described by T. V. Byzova et al., *Exp. Cell Res.,* 254:299-308 (2000). The migration assay utilizes HTS Multiwell tissue culture inserts with 8 µm pore size (Becton Dickinson, N.J.). Angptl3 protein was diluted in PBS to 50 ng/µl and used to undercoat the surface of the membrane filter. After precoating with 3%BSA/PBS, the filters were placed in 500 µl serum-free CS-C medium, 1%BSA, 1 mM $CaCl_2$. HMVECs were washed 3 times with PBS, harvested and suspended at $10^5$ cells/ml in serum-free medium supplemented as described above. The cells were preincubated with or without blocking antibodies (25 µg/ml) for 15 minutes at 37° C. prior to stimulation with PMA (200 nM). The cell suspension (250 µl) was added to the upper chamber and the cells were allowed to migrate overnight at 37° C. in a 5% $CO_2$ humidified incubator. After incubation, cells remaining in the top wells were removed using a swab, and the cells that had migrated to the lower surface of the membrane were fixed with methanol and stained with YO-PRO-1 iodide (Molecular Probes). Migration results were quantitated as the average number of cells/microscopic field using the Openlab software (Improvision, MA).

Figure 7E:
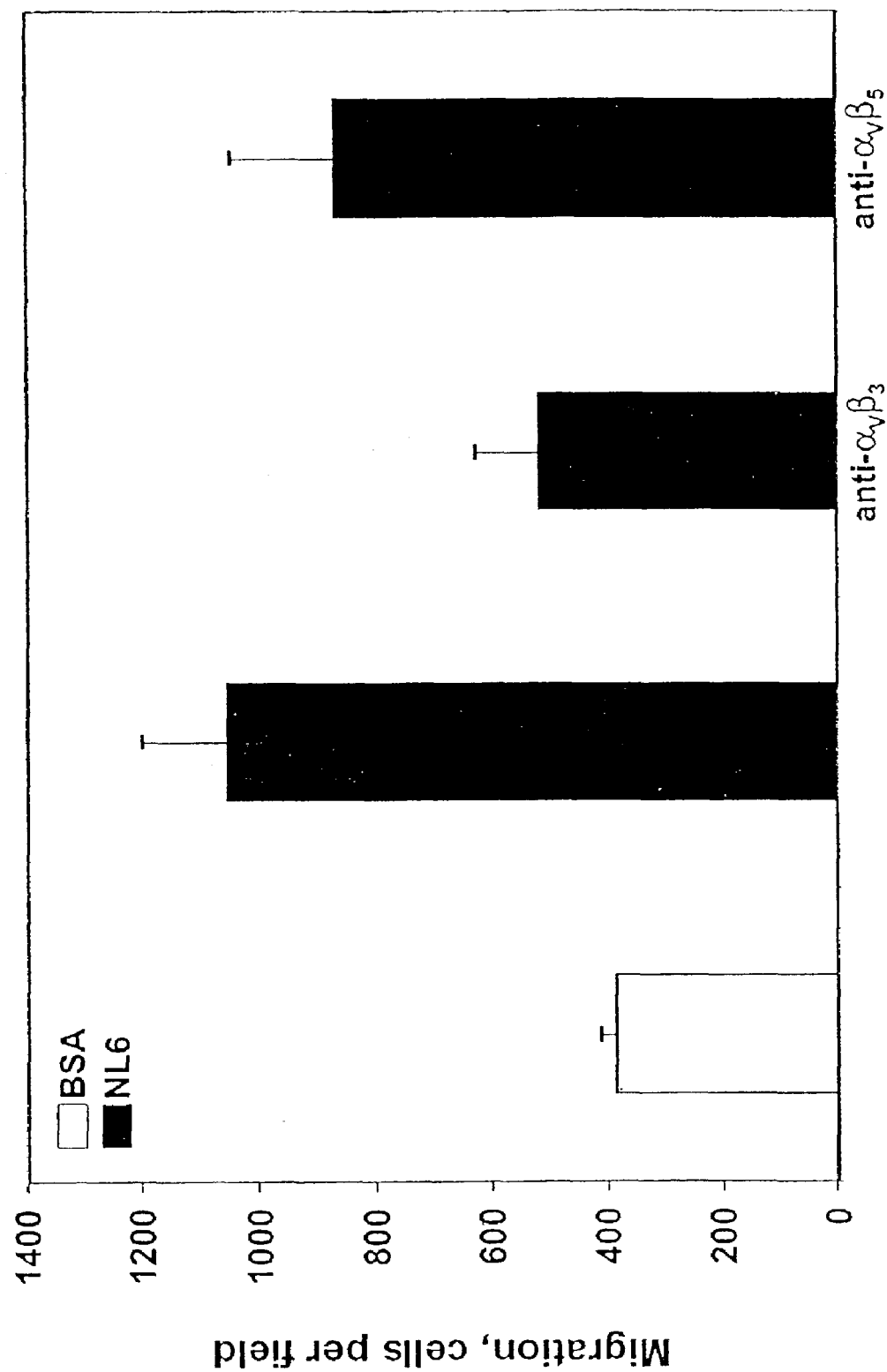

After 16 to 20 hours exposure of Angptl3 to endothelial cells, a 2.5 fold increase in cell migration compared to BSA control treatment (FIG. 7E) was observed. Most importantly, such migration was blocked by administration of an antagonistic antibody to αvβ3, but not by control antibodies blocking other integrins. In conclusion, Angptl3 potently induces migration of primary human endothelial cells and both activities were blocked by antagonistic antibodies toward αvβ3.

Example 8

Tissue Expression of Angptl3

A. In situ Hybridization.

In situ hybridization was performed as previously described (Lu, *Cell Vision* 1: 169-176 (1994)). PCR primers upper: 5' T7 promoter: GGATTCTAATACGACTCACT ATAGGGC (SEQ ID NO: 6)+GGCATTCCTGCTGAATG-TACC (hAngptl3 specific sequence, SEQ ID NO: 7) 3' and lower: 5' T3 promoter: CTATGAAATT AACCCTCAC-TAAAGGGA (SEQ ID NO: 8)+ACCACACTCATCATGC-CACCA (hAngptl3 specific sequence, SEQ ID NO: 9) 3' were designed to amplify a 506-bp fragment of human Angptl3 and upper: 5' T7 promoter: GGATTCTAATACGACTCAC-TATAGGGC (SEQ ID NO: 6)+5' GATGACCTTCCTGC-CGACTG (mAngptl3 specific sequence, SEQ ID NO: 11) 3' and lower: T3 promoter: CTATGAAATTAACCCTCAC-TAAAGGGA (SEQ ID NO: 8)+5' GTCATTCCACCAC-CAGCCA (mAngptl3 specific sequence, SEQ ID NO: 13). Primers included extensions encoding 27 nucleotide T7 or T3 RNA polymerase initiation sited to allow in vitro transcription of sense or antisense riboprobes, respectively, from the amplified products. Human tissue 5 µm thick sections were deparaffinized, deproteinated in 20 µg/ml proteinase K for 15 minutes at 37° C., rinsed in 2xSSC, dehydrated through graded concentrations of ethanol and incubated in prehybridization buffer 1-4 h. The mouse tissues were digested in 4 µg/ml proteinase K for 30 minutes at 37° C. and treated as described above. $^{33}$P-UTP-labeled sense and antisense probes were hybridized to the sections at 55° C. overnight. Unbound probe was removed by incubation in 20 mg/ml RNaseA for 30 minutes at 37° C., followed by a high stringency wash at 55° C. in 0.1xSSC for 2 hours, and dehydration through graded concentrations of ethanol. The slides were dipped in NBT2 nuclear track emulsion (Eastman Kodak, N.Y.), exposed in sealed plastic slide boxes containing desiccant for 4 weeks at 4° C., developed, and counterstained with hematoxylin and eosin.

Figure 8A:
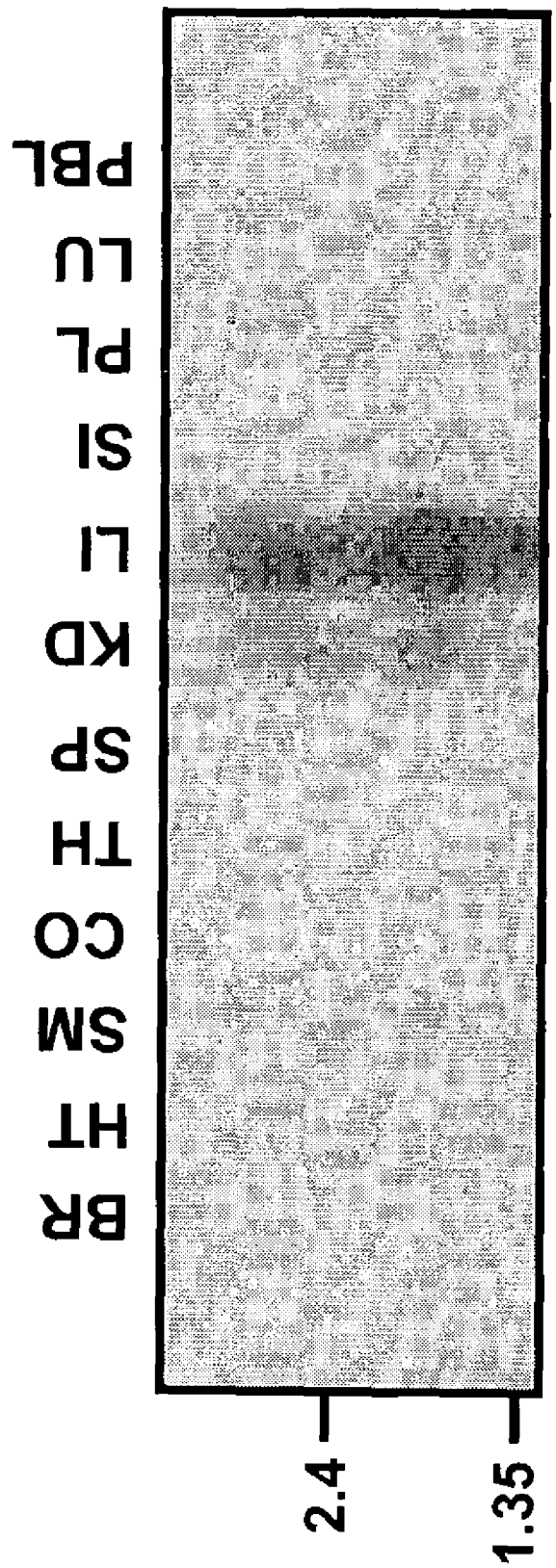
FIGS. 8A-C show that Angptl3 is expressed in hepazocytes during development and is strongly upregulated in diseased liver. (A) Northern blot analysis of hAngptl3 was done using human multi-tissue blots (CLONTECH) and revealed expression of hAngptl3 in the liver and kidney. Each lane contains 2 μg of RNA from adult grain (BR), heart (HT), skeletal muscle (SM), colon (CO), thymus (TH), spleen (SP), kidney (KD), liver (LI), small intestine (SI), placenta (PL), lung (LU), and peripheral-blood leukocyte (PBL). (B) Expression of hAngptl3 is strongly upregulated in hepatocytes in tissues from liver cirrhosis and after toxic injury wit acetominophen. No alterations were observed within a liver tumor samples. (C) In situ hybridization of fetal mouse liver shown expression of mAngptl3 at E15 and E18 in hepatocytes but not in erytbroid progenitors, endothelial cells and megakaryocytes.
Figure 8B:
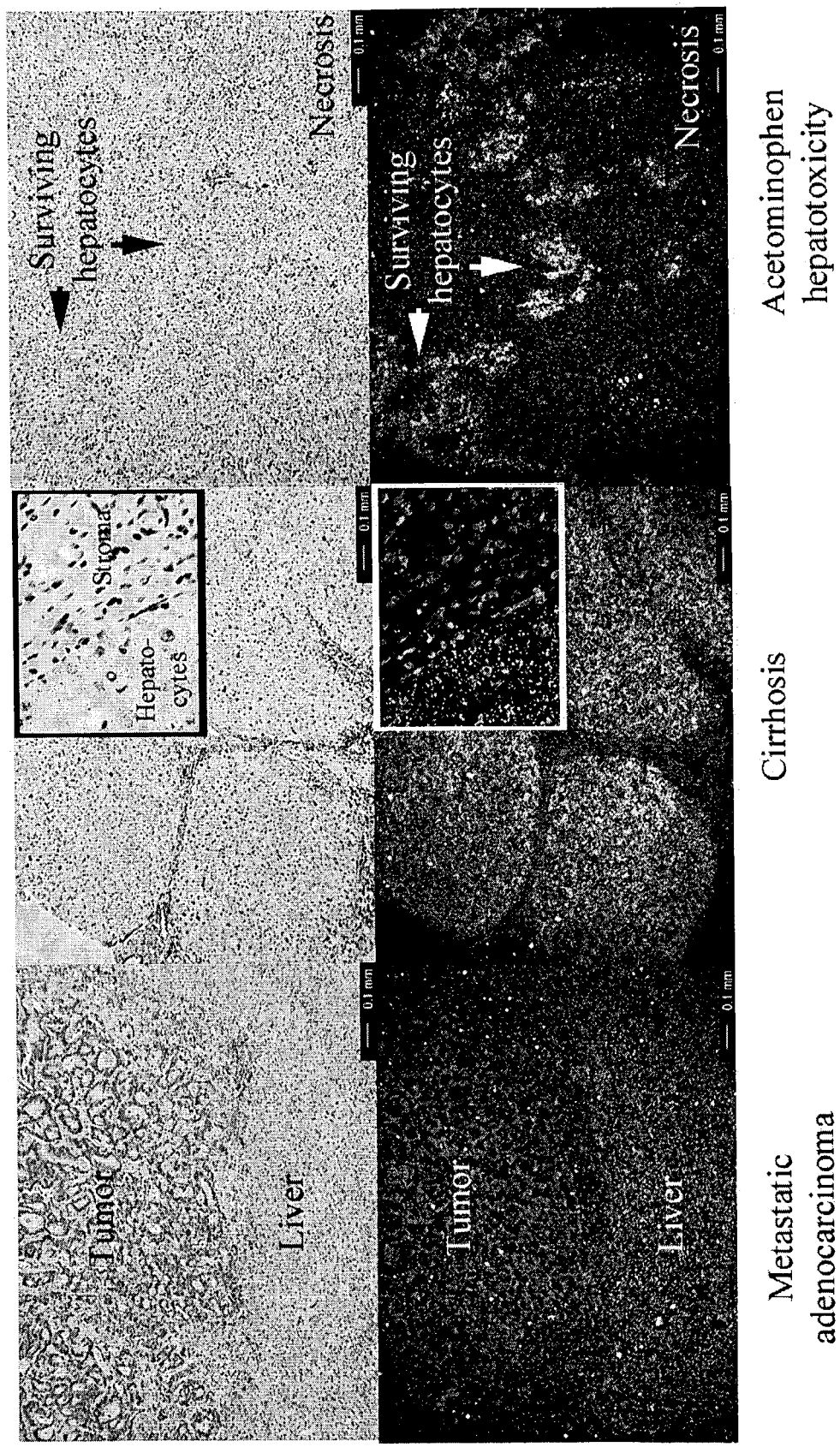
Figure 8C:
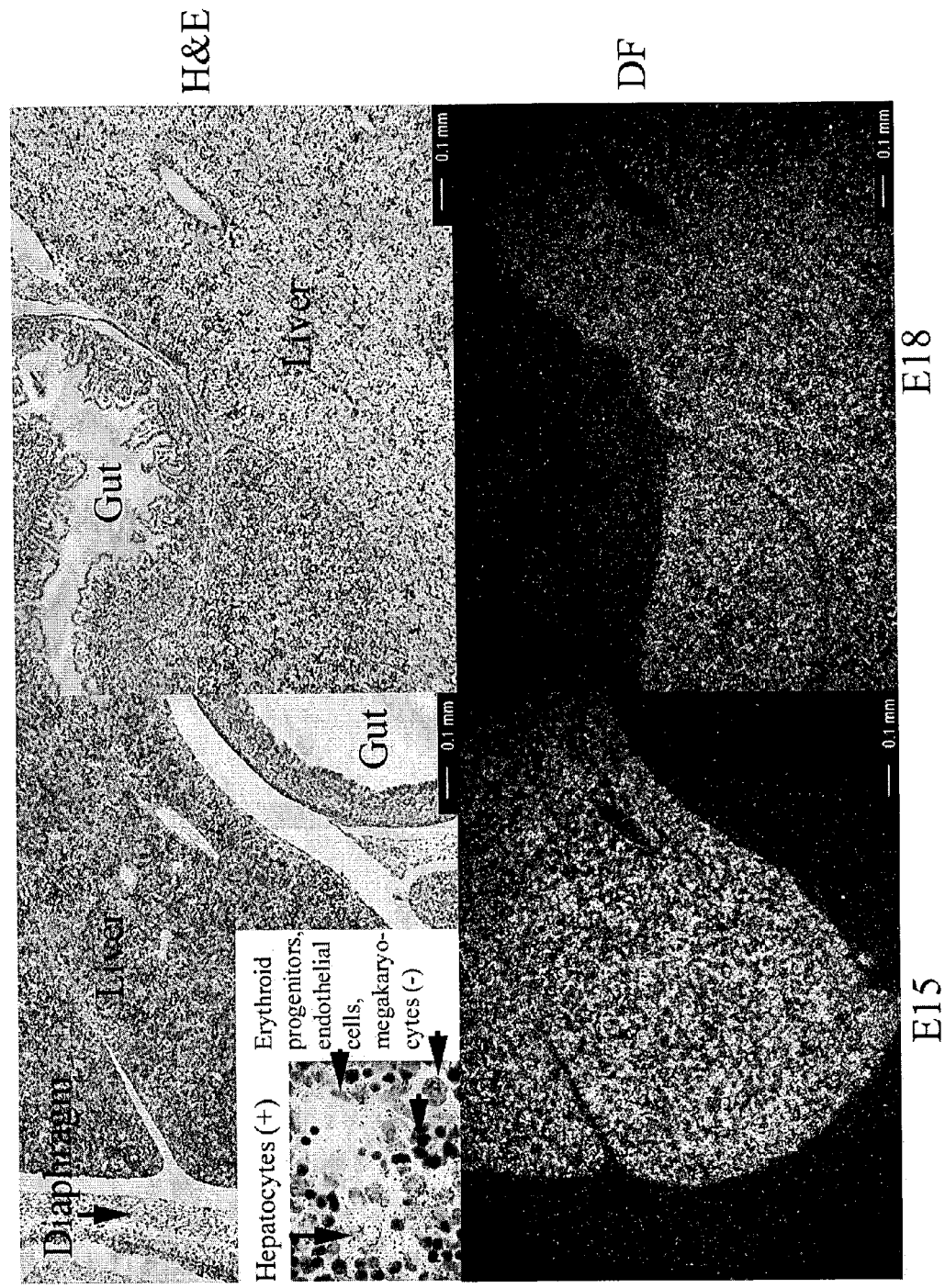

As shown in FIG. 8C, hepatocyte specific expression as observed in sections of embryonic livers from E15 and E18 mouse embryos. There was no Angptl3 expression on erythroid progenitors, endothelial cells or megakaryocytes within the embryonic sections analyzed.

B. Northern Blots

In order to study the Angptl3 expression in adult human tissues, multi-tissue Northern blots were probed with a radiolabeled probe covering the 5' end of the coding sequence, as described above. In contrast to previous observation with the murine orthologue Angptl3 (Conklin et al., Genomics 62:477-82 (1999)), which was found to be expressed exclusively in the liver, expression of human Angptl3 was found in adult liver and kidney, however, the signals observed in kidney were significantly lower (FIG. 8A). No expression was found in any of the other adult tissues analyzed, including lung and brain with the exception of some weak signals in skeletal muscle tissues. Cellular localization of Angptl3 mRNA expression was investigated by in situ hybridization experiments on various normal and diseased tissues derived from human and mouse specimens. The tissues included all major organs, bone marrow, as well as pathologic liver tissues such as cirrhosis, metastatic liver adenocarcinomas and section from cases of acetaminophen induced hepatotoxicity. As shown in FIG. 8B, some background expression was found in normal adult liver confirming the northern blot data. While there were no alterations in the expression within liver tumor samples analyzed, strong induction was observed in sections derived from diseased liver associated with inflammation, such as liver cirrhosis and after toxic injury. As shown in the high magnification insets, hepatocyte specific expression was found in both normal and diseased liver tissues (FIG. 8C). Expression was not detected in stromal cells, in lymphocytes and in endothelial cells within or surrounding the diseased tissues.

In summary, these data demonstrate a hepatocyte specific expression pattern for Angptl3 during embryonic development as well as a strong, hepatocyte specific upregulation in various cases of diseased liver associated with inflammation.

C. Gene Expression Profiling

Gene Expression analysis was performed for Angptl3 using GeneLogic database of human tissues representing normal and disease states, including cancer and non-cancer.

Using the GeneLogic gene expression database, increased expression in conditions of liver diseases identified by in situ hybridization of human liver sections (FIG. 8B) was confirmed. Basal levels of Angptl3 was low in most tissues and organs, with the exception of liver. A significant increase in expression levels of Angptl3 between normal and pathologic conditions was present in liver, heart and thyroid. A more detailed subtype analysis for Angptl3 expression with samples derived from patients suffering from various forms of liver diseases confirmed strongest expression of Angptl3 during liver cirrhosis. Interestingly, GeneLogic database analysis revealed strong induction of Angptl3 expression not only in pathologic livers, but also in heart diseases such as coronary heart diseases and hypertrophic cardiomyopathy. The disease forms associated with increased expression levels of Angptl3 share in common the formation of fibrotic tissues consisting of a variety of extracellular matrix proteins including collagen, fibronectin, vitronectin and laminin, all of these ECM molecules are known to bind to specific integrin forms.

Example 9

Assay for In Vivo Angiogenic Activity of Angptl3

Figure 9E:
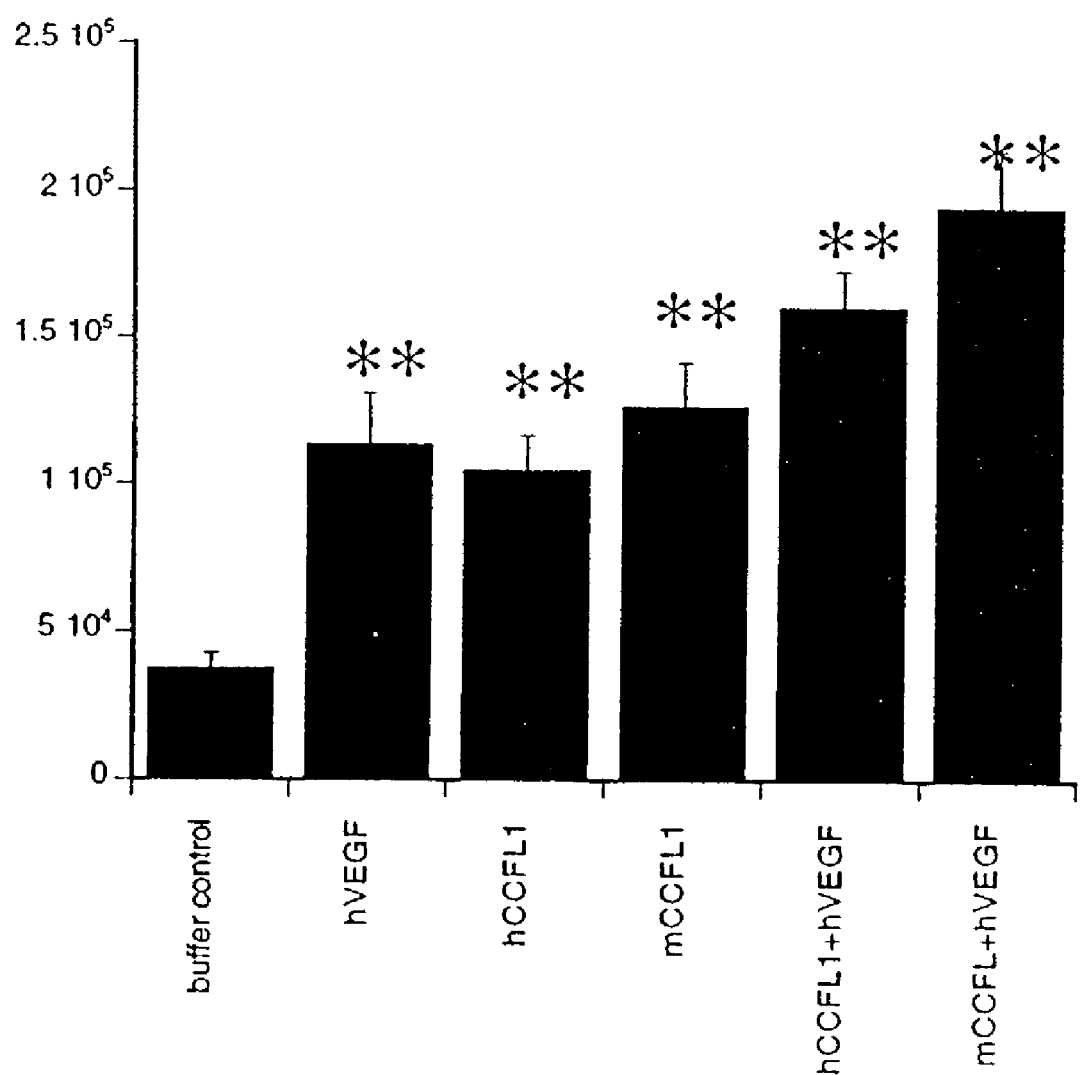

In order to test whether Angptl3 was capable to induce an in vivo angiogenic response in the rat cornea, hyaluron pellets containing murine and human Angptl3 (500 ng) as well as human VEGF (100 ng) were implanted separately or in combination as described previously (Xin et al., J. Biol. Chem., 274:99116-9121 (1999)). Hydron pellets containing excipient (control, murine or human Angptl3 (500 ng), VEGF (100 ng), or the combination of murine or human Angptl3 (500 ng) and VEGF (100 ng) were implanted into the corneas of 250 to 300 g male Sprague-Dawley rates. All hydron pellets contained 100 ng of sucralfate. At day 6, animals were euthanized and injected with fluorescein isothiocyanate-dextran to allow for visualization of the vasculature. Corneal whole mounts were made of the enucleated eyes and analyzed for neovascular areas using a computer-assisted image analysis (Image Pro-Plus 2.0, Silver Spring, Md.). In contrast to previous reports focusing on the effects of angiopoietin 1 and 2 when tested in the corneal angiogenesis assay (Asahara et al., Circ. Res. 83:233-40 (1998)), recombinant Angptl3 alone potently induced a strong angiogenic response 5 days after pellet implantation. As shown in FIGS. 9A and B, murine Angptl3 was slightly more potent in inducing angiogenesis when compared to the recombinant human protein, however, both responses were comparable to the levels obtained for VEGF. In the combination treatment with VEGF, additive but not synergistic effects were observed (FIG. 9B). These findings might reflect the interdependent signal transduction pathways engaged by both ligands (Byzova et al., Mol. Cell. 6:852-60 (2000)).

Example 10

In Vivo Biological Activity of Angptl3

A. Transient Protective Effect and Long-Term Effect of Intravenous and Intradermal Administration of Angptl3

Methods

Adenovirus generation: Adenoviral CMV-gD-mAngptl3, CMV-lacZ and mVEGF164 were generated using the AdEasy adenoviral vector system (STRATAGENE) essentially following the manufacturer's instructions. Recombinant adenoviral vectors encoding murine Angptl3 or VEGF was constructed by cloning the coding region of Angptl3 or VEGF into the polylinker site of the Ad-easy vector construction kit from STRATAGENE. The coding region of mAngptl3 or VEGF was cloned between the NotI and HindIII sites of the pShuttleCMV vector. These vectors, along with the supplied pShuttleCMV-lacZ, were recombined, in BJ5183 electrocompetent bacteria (STRATAGENE), with the AdEasy vector containing the Ad5 genome deleted for E1 and E3 regions. Primary viral stocks were prepared by transiently transfecting the recombined AdEasy plasmids into host HEK293 cells. Adenovirus stocks were further amplified in HEK293 cells and purified using the Virakit Adeno purification kit (Virapur). Adenovirus titres were obtained by agarose-overlaid plaque assays.

1. Protective Effect of Short-Term Intravenous Administration of Angptl3

Figure 10A:
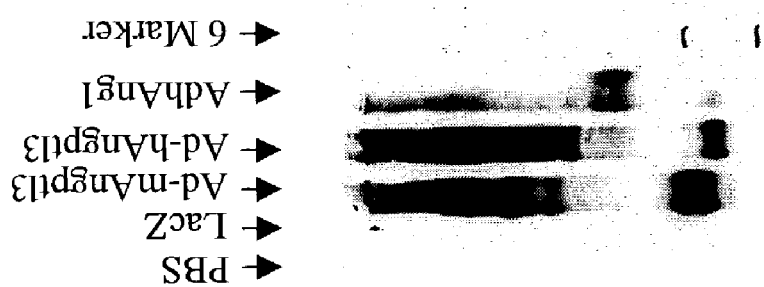
FIGS. 10A-B show the protective effect of murine Angptl3 in CC14 induced liver toxicity as assessed by serum levels of aspartate transferase (AST) at day 7 after adenoviral infection at day 0 and CC14 treatment at day 4.

For short-term analysis of liver protection from toxic injury, Adenoviral constructs was administered to 12 adult BalbC mice via tail vein injections which allows for continuous and robust expression of protein in the livers as early as 2 days for up to 3 weeks after treatment at a dose of $1 \times 10^9$ Pfu for mAngptl3 and LacZ encoding control virus, and $1 \times 10^9$ Pfus of VEGF encoding virus. 5 days after treatment with adenoviral vectors, the mice were subdivided into two subgroups (n=6) that were further subjected to treatment with: vehicle (olive oil) or CC14 (carbon tetra chloride), the potent hepatotoxic agent which induces liver damage. Both, vehicle and CC14 were given at 4 ml/kg by oral gavage. After 48 hours, animals were killed, blood was collected and tissues were harvested and fixed for analysis. The levels of construct expression in the mice were analyzed by western blot analysis at day 7 after adenoviral infection (FIG. 10A).

Results

Figure 10B:
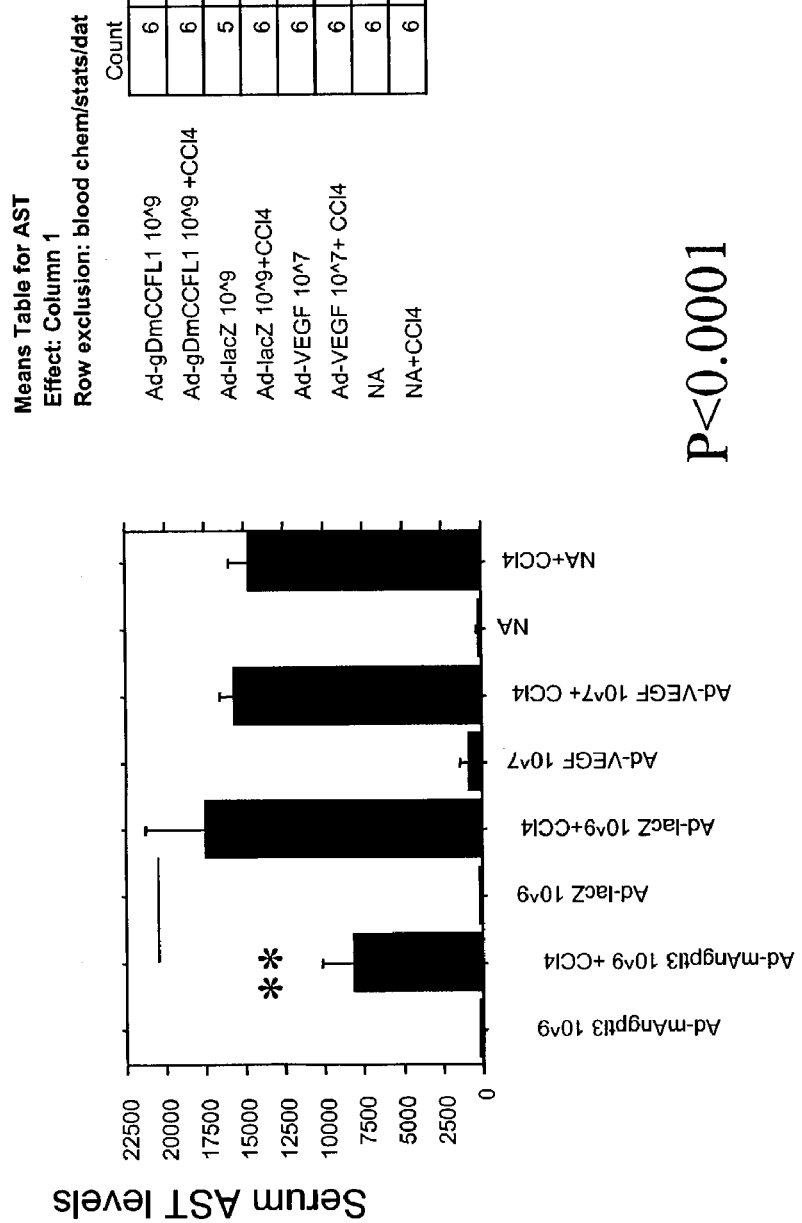

The protective effect of Angptl3 on CC14 induced hepatocyte necrosis was demonstrated by the significant, 2.1 fold reduction in the blood levels of aspartate transferase (AST), which is an indicator of liver failure, in the serum from mice treated with adenovirus encoding Angptl3, but not by any of the control constructs ($p<0.0001$) (FIG. 10B). Accordingly, transient administration of recombinant Angptl3 may be beneficial for the treatment of liver injuries.

2. Induced Liver Damage with Prolonged Intravenous Expression of Angptl3

In order to assess the long term effects of increased Angptl3 levels, mice that were treated with adenoviral vectors encoding Angptl3 as described above were characterized during a period of 2 weeks post viral transduction.

a. Blood Chemistry Analysis

Blood chemistry levels indicative for liver function was measured in serum samples taken from wild-type, C57Bl6 mice, during a period of 2 weeks post adenoviral transduction. Hematology Cell-Cyn 13700, and blood chemistry levels were determined on a Cobas Integra 400.

As shown in FIG. 11A, adenoviral vectors encoding Angptl3, but not control viruses encoding LacZ or Angiopoietin 1 (Ang1), induced a strong increase in serum ALT and AST levels. The increase in serum ALT and AST levels was comparable to levels of ALT and AST that are observed with carbon tetrachloride treatment. Accordingly, interference with Angptl3 activity may be potential treatments during inflammatory diseases of the liver or diseases of the heart.

Figure 11B:
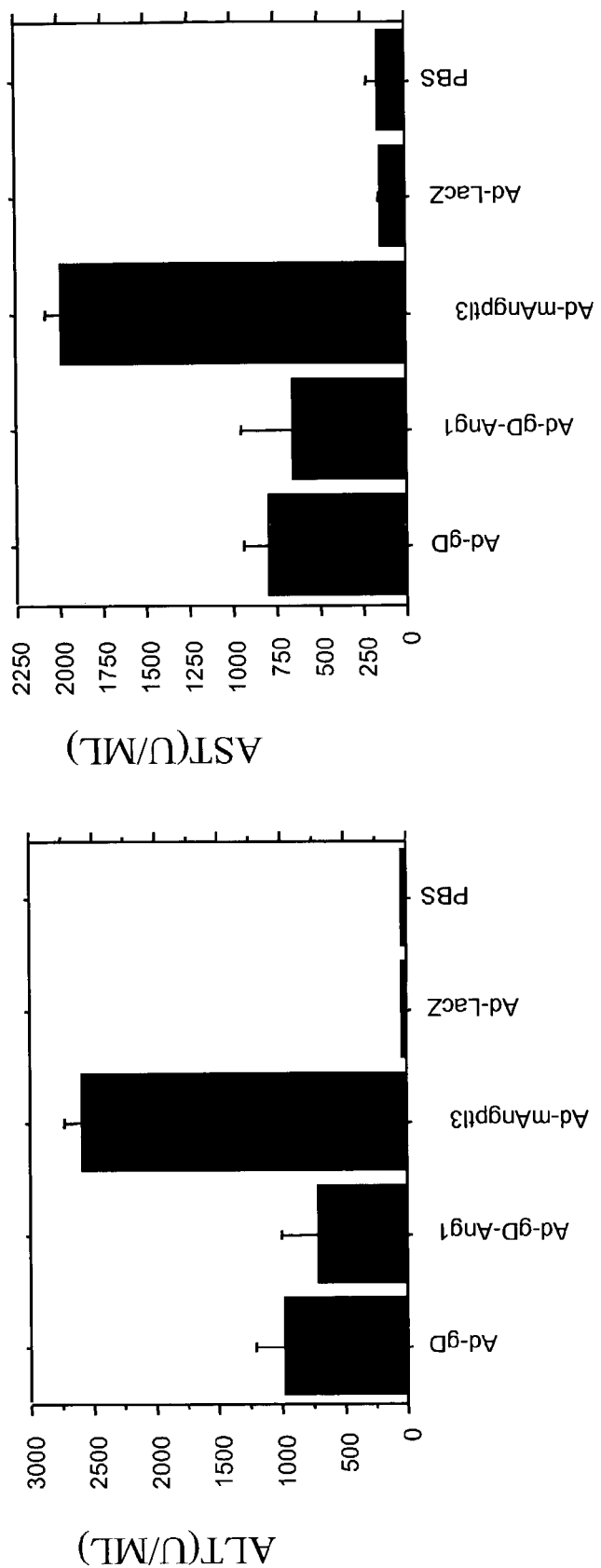

In order to further assess a potential contribution of the immune system, blood chemistry levels indicative for liver function was measured in immuno-compromised RAG2-knock out mice, which lack B- and T-cells and SCID mice, which lack B, T and natural killer (NK) cells. As shown in FIG. 11B, adenoviral vectors encoding Angptl3 induced AST and ALT levels in RAG2 mice, suggesting that the changes in liver function induced by Angptl3 occur irrespective of the presence of an intact immune system.

b. Hepatocyte Proliferation

To further characterize the effect of treatment with adenoviral vectors expressing Angptl3 on RAG2-knock out and SCID mice, cell proliferation in various formalin-fixed, BrdU incorporated organs, including kidney, heart, liver, lung and small intestine, of treated mice was quantitated in RAG2-knock out and SCID mice that were either treated with adenoviral vectors expressing Angptl3 or control adenoviral vectors. Cell proliferation was measured by performing BrDU staining which detects cells during the S phase of the cell cycle on paraffin-embedded sections that were taken from the control- or Angptl3-treated mice 14 days post adenoviral administration (IV). BrdU was administered intraperitoneally to animals at the dose of 100 mg/kg, 1 hour prior to sacrifice. After a 20 minute treatment with 0.05% trypsin at 37° C. and a 45 minute treatment with 95% formamide in 0.15M trisodium citrate at 70° C. for denaturing, tissues were stained with mouse antibodies to IdU/BrdU (Caltag) at a dilution of 1:1000 overnight at 4° C. A biotinylated horse antibody to mouse IgG (Vector) was used as the secondary reagent and detected by using the Vectastin ABC Standard Elite kit (Vector Laboratories). Mouse Isotype (ZYMED) was used as a negative control. Sections were then counterstained with hematoxylin. The total number of labeled nuclei in 10 independent, randomly selected fields using a 40× objective, were counted. Each filed covered an area of 0.063 mm².

As shown in Table 2, a greater than 10 fold induction of hepatoycte proliferation was observed in RAG2-knock out and SCID mice that were treated with adenoviral vectors expressing Angptl3.

TABLE 2

Increased BrDU staining in liver sections of Angptl3 treated RAG2 knock out or SCID beige mice relative to control treatment 14 days post treatment

| | RAG2 knock out mice | Scid beige nude mice |
|---|---|---|
| PBS | 13.0 ± 5.3 | 9.0 ± 6.2 |
| Ad-LacZ (1 × 10⁹ PFU) | 3.5 ± 1.3 | 3.3 ± 1.7 |
| Ad-Angptl3 (1 × 10⁹ PFU) | 81.2 ± 24.9 | 67.2 ± 20.1 | c. Histological Analysis

Histological analysis was performed on liver sections that were harvested from C57/B16 14 days after infection with adenoviral vectors. An increase in mitotic figure which are indicative of cell proliferation within hepatocytes and inflammatory infiltrates was observed in the liver sections that were isolated from mice treated with adenoviral vectors encoding Angptl3 when compared to livers that were isolated from control mice that were treated with adenoviral vectors encoding LacZ. The livers of Angptl3-treated animals were also significantly larger than livers of control-treated animals.

d. FACS Analysis

Although LFA1 and Mac-1 expressed on immune cells did not bind to recombinant Angptl3 (Camenisch et al., 2002) when tested by ELISA assays in vitro, other members of the integrin family that are expressed on immune cells may be involved with Angptl3.

In order to study the possibility that inflammatory cells contribute to the tissue damage observed in livers of mice treated with adenoviral vector expressing CCLF1, the amount of peripheral blood cells was determined by FACS for the presence of the various lineages by staining for cell type specific markers. No significant differences in the amounts of progenitors (Sca1), T-cells (CD4 and CD8), B-cells (B220), macrophage (Gr1/Mac1) and erythroid cells (Ter119) was detected in the mice treated with adenoviral vector expressing Angptl3 when compared to amounts detected in mice treated with control adenoviral vectors expressing LacZ or Ang1. Similarly, no difference in the amount of serum glycerides and cholesterol was observed between the treatment groups.

e. Cell Adhesion Analysis

To further investigate the cellular mechanism involved in mediating liver damage, cell adhesion experiments with hepatocytes and endothelial cells on Angptl3-coated tissue culture dishes were performed similar to cell adhesion assays described in Example 6.

96-well flat-bottomed plates (MaxiSorp, Nunc, Denmark) were coated overnight at 4° C. with the indicated concentrations of proteins and blocked with 3% BSA in PBS for 1 hour at 37° C. Primary human dermal endothelial cells (HMVECs) and freshly isolated murine hepatocytes that were prepared from the livers of adult C57/B16 mice using the method described in LeCouter et al (LeCouter et al., 2001) were harvested and diluted to 105 cells/ml in serum-free CS-C medium containing 1% BSA, 1 mM $CaCl_2$ and 1 mM $MgCl_2$ in the presence of 200 nM PMA. Qualitatively similar results with regard to cell binding were observed in the absence of PMA. Cell suspensions (104 cells/well) were added to the coated wells and the plates were incubated at 37° C. for selected times. Non-adherent cells were removed by PBS washes and cell attachment was measured using the PNAG method of Landegren (Landegren, 1984). Results were expressed at mean $OD_{405}$ values of triplicate wells.

Figure 13:
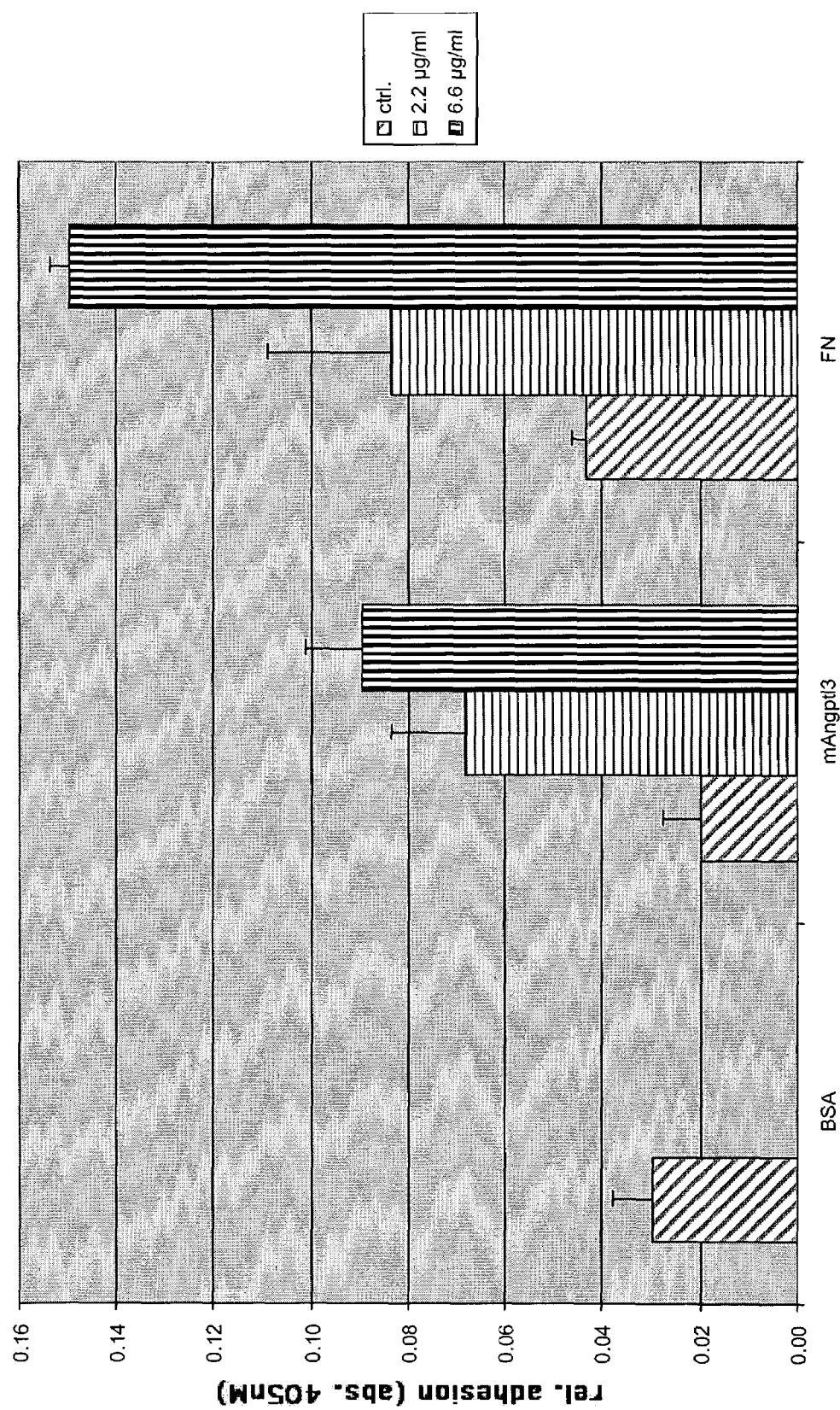
FIG. 13 shows the level of binding of freshly isolated murine hepatocytes to recombinant murine Angptl3 (mAngptl3). Hepatocyte adhesion to culture dishes coated at the indicated concentrations of recombinant mAngptl3, fibronectin or BSA control. Unspecific binding was blocked by 3% BSA at 37° C. for 1 hour, and wells were washed with PBS before cells were plated. The data shown represent means±SD of one representative experiment run in triplicates of a total three independent experiments.

As shown in FIG. 13, HMVEC adhesion to Angptl3-coated dishes was between 20% and 50% relative to the level of adhesion observed for fibronectin-coated plates. Coating-concentration dependent hepatocyte adhesion was also observed. Accordingly, hepatocytes and endothelial cells may be involved in mediating the biological effects observed in the liver of Angptl3 treated mice.

3. Increased Vascular Permeability with Intradermal Administration of Angptl3

To study the vascular changes induced by transient Angptl3 expression in adult mice, adenoviral expression vectors ($1\times10^{-9}$ PFUs) were administered in a total volume of 10 µl into the epidermal skin layer of the ears of adult FVB mice under anesthesia and further analyzed for changes in vascular permeability by using the Evans Blue assay. Briefly, mice were anesthetized from the beginning and throughout the entire Evans Blue assay. After onset of anesthesia, 100 µl of Evans Blue (1% solution in PBS) was administered intravenously to the mice via tail vein injection. After a period of 60 minutes post administration of Evan Blue, mice were perfused from the left ventricle with 1% paraformaldehyde in citrate buffer at a pH of 3.5 at a pressure of 120 mmHg. Ears were removed and weighed. Evans blue dye was extracted from the ears with 1 mL of formamide. The amount of extravasated Evan Blue was measured with a light spectrophotometer at 610 nm and expressed as the content dye per 1 mg of wet weight of tissue.

Results:

An increase in vascular permeability that was measured by Evans Blue assay as relative to the levels of vascular permeability in mice administered control adenoviral vectors expressing LacZ, was observed in the ears of mice that were intradermally administered adenoviral vectors expressing Angptl3 or VEGF (FIG. 12D), 6 days post administration.

B. Increased Vascular Permeability in Transgenic Mice Expressing-K5-mAngptl3

In an alternate method, the developmental effects of increased levels of Angptl3 expression in the skin were studied by generating transgenic mice that expressed murine Angptl3 under the control of a keratinocyte specific promoter, which is constitutively expressed during development and in adults.

1. Founder Transgenic Mice

Founder transgenic mice were made using K5-gD-mAng5, a construct that allows expression of Angptl3 under the control of the murine K5 promoter, as per standard procedures (Filvaroff et al., 2002). For generation of the K5-gD-mAng5 construct, the Angptl3 gene was cut out NotI-NotI and inserted into pNASSK5β NotI-NotI-SAP resulting in K5-gD-mAng5.

A total of 17 transgenic founder strains were generated. The mice pups were genotyped at 9 days of age by PCR of mouse tail DNA (QIAGEN, Santa Clarita, Calif.) using the following primer sets:

```
gD-mAng5.311.F:                    /
ATATGCCTTGGCGGATGC; and            (SEQ ID NO:32)

gD-mAng5.578.R:
ATGGACAAAATCTTTAAGTCCATGAC.        (SEQ ID NO:33)
```

At 8 weeks of age, biopsies of several tissues, including muscle, kidney, liver, spleen, skin, brain, thymus an intestine, were taken and subjected to real time RT-PCR for the determination of the levels of endogenous and transgene expression of Angptl3. For RT-PCR analysis, the following probes and primers which were designed such that endogenous and transgenic transcripts were measurable were used:

```
MMAng5.1165.FP:  FAM-CTCCCAGAGCACACAGACCTGATGTTTT-TAMRA  (SEQ ID NO: 34)

MMAng5.1144.F:   GCTGGCAATATCCCTGGG                       (SEQ ID NO: 35)

MMAng5.1223.R:   AGCTGTCCCTTTGCTCTGTGA                    (SEQ ID NO: 36)
```

Statistical analysis of differences between transgenic mice expressing Angptl3 under the murine K5 promoter was determined by a Student's t test with a value of P<0.05 considered to be statistically significant and as value of P<0.01 as highly significant.

2. Progeny Transgenic Mice

Based on gene expression analysis from skin biopsies of all the transgenic founder mice, the five most highly Angptl3-expressing founders were identified and selected for further breeding to C57/B16 mice. Genotype frequency analysis revealed normal Mendelian frequency distribution of the transgene and no significant postnatal lethality was observed to be associated with transgene expression.

a. Transgene Expression

RNA from various tissues indicated was isolated and the relative levels of transgene expression relative to endogenous expression, specifically in the liver, was assessed by real time RT-PCR.

As expected, increased levels of murine Angptl3 expression was observed in the skin of transgenic versus liter matched wild-type controls. Transgene expression of Angptl3 in the skin reached about 10% of the endogenous Angptl3 expression levels in the liver (FIG. 12A).

Further, moderate expression in the lung and the brain of 12 weeks old transgenic mice when compared to wild-type mice was observed. Accordingly, the expression in the lung and the brain may result from increased transcriptional activity of the K5 promoter in these tissues.

In support of the moderate Angptl3 expression found by Northern blot analysis in adult human kidneys (FIG. 8A), Taqman analysis of mouse kidney RNA revealed moderate endogenous expression levels of Angptl3.

Figure 12B:
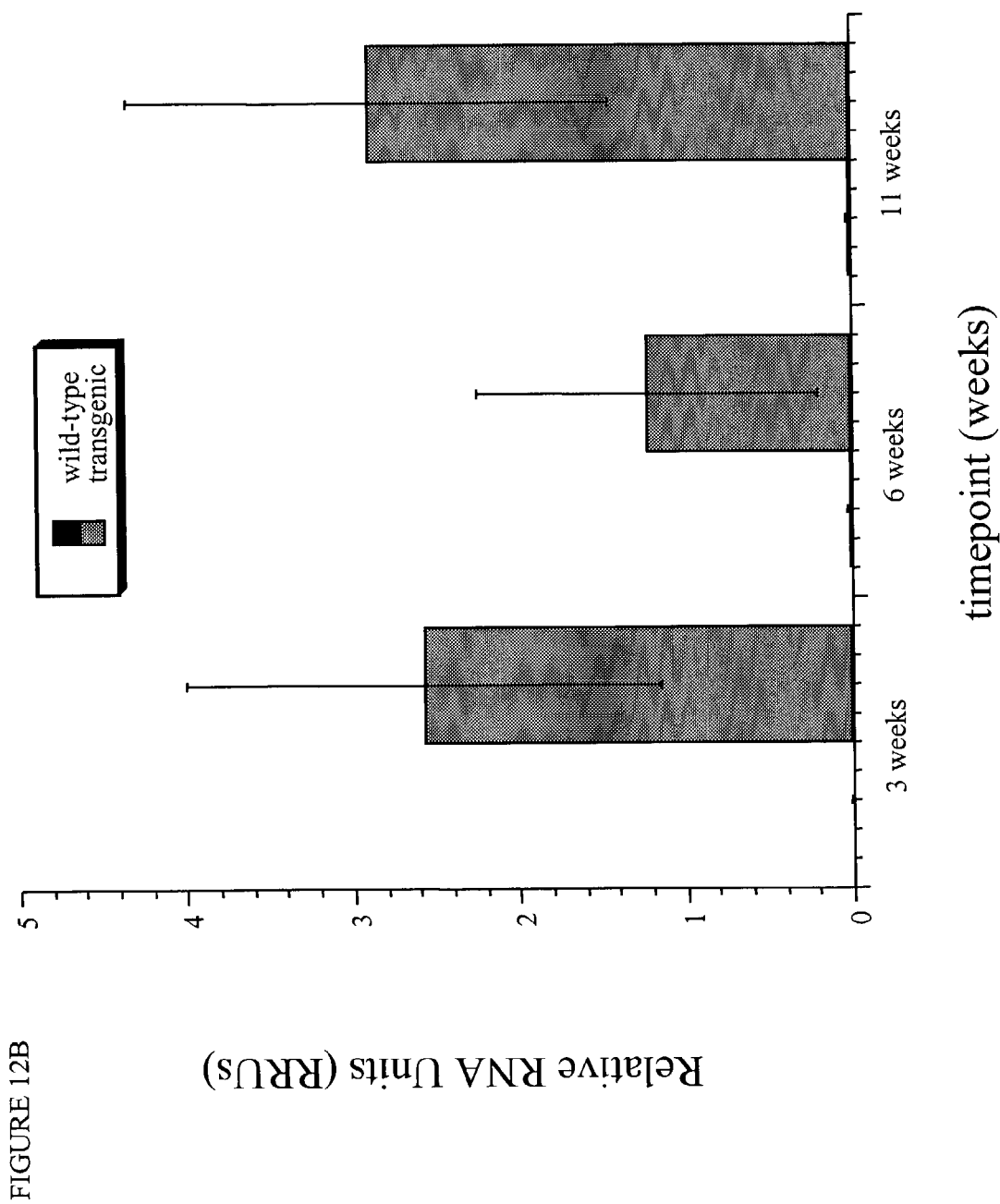

In order to monitor postnatal transgene expression over time, real time RT-PCR analysis was conducted with RNA isolated from skin biopsies of 3, 6 and 11 week old transgenic mice. As shown in FIG. 12B, consistent levels of transgene expression were observed in the skin of transgenic mice at all developmental stages tested.

b. Vascular Permeability

Figure 12C:
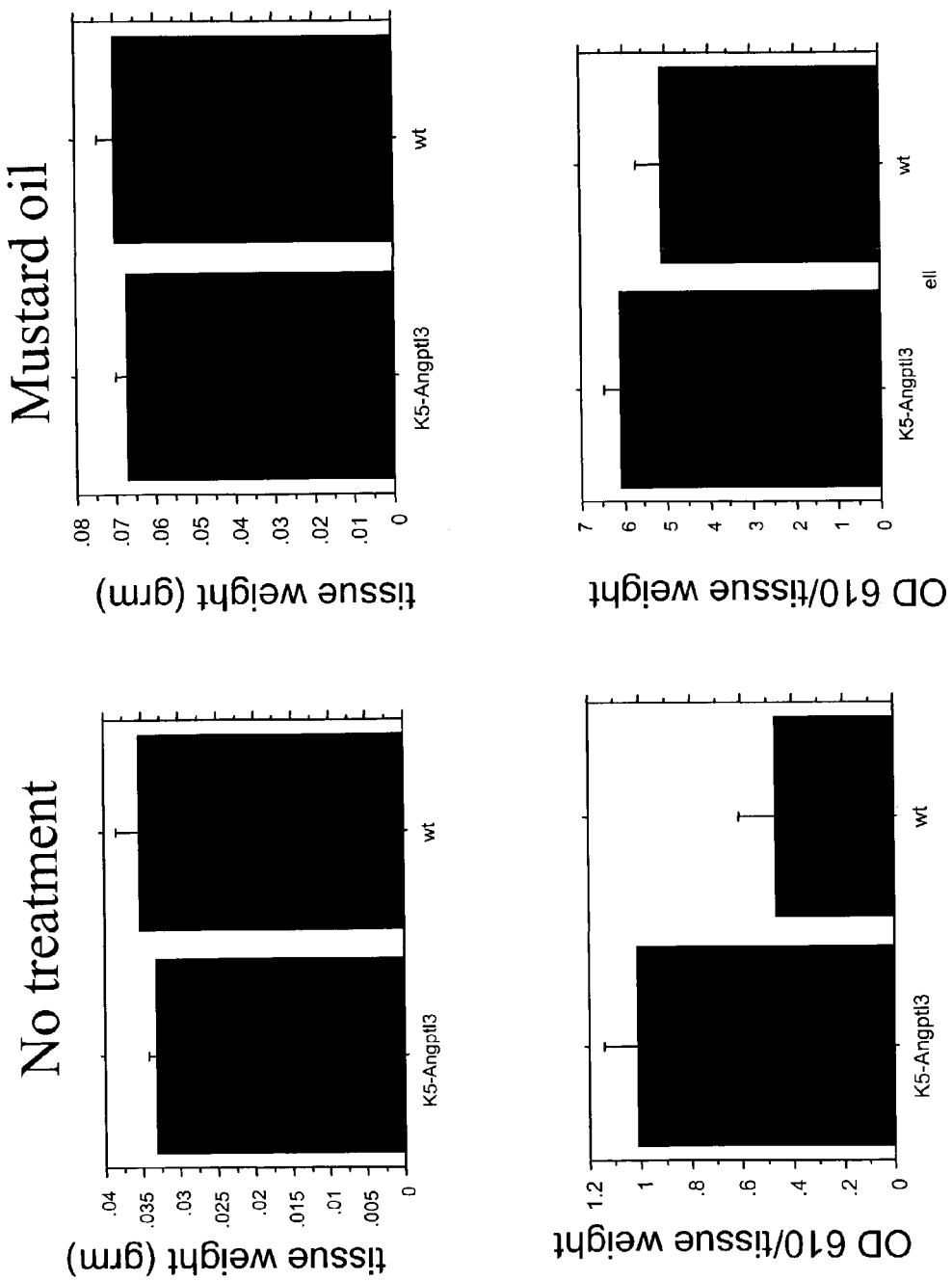
Figure 12D:
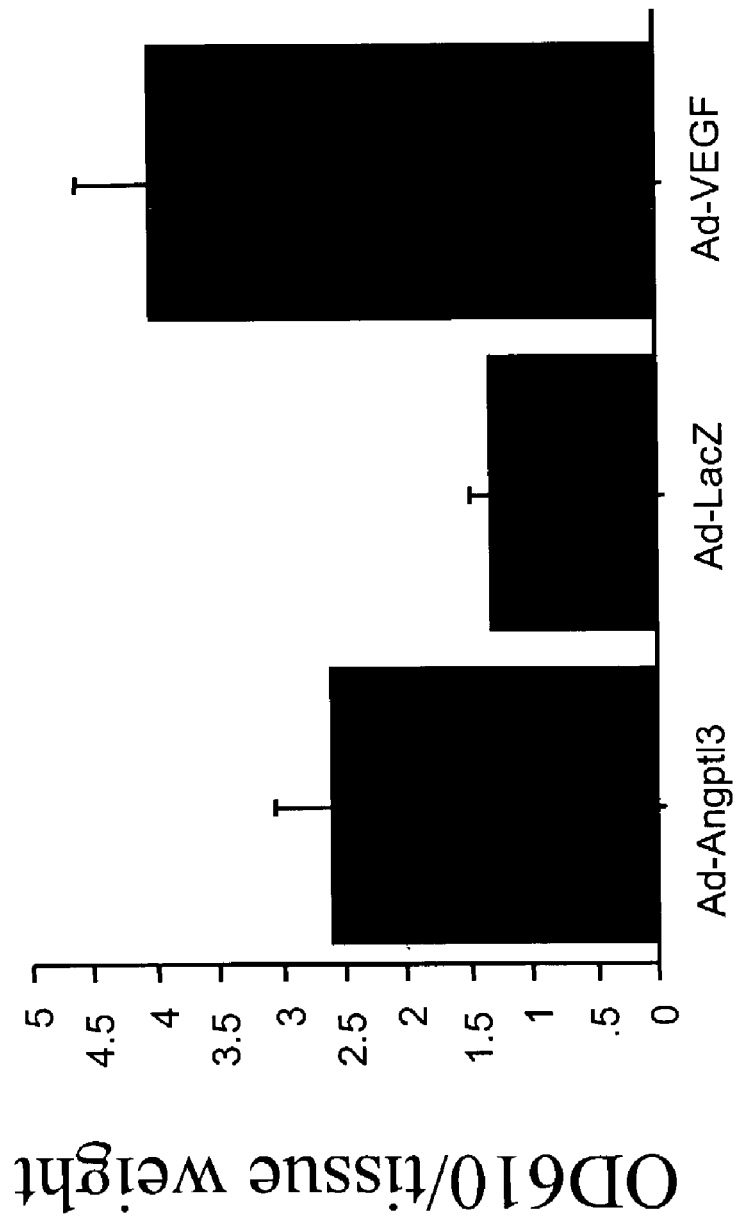

Based on the transgene expression data, 12 week old transgenic and wild-type liter matched wild-type controls were selected and subjected to an assay for vascular permeability using the Evans Blue assay similar as described above and previously for Ang1 and Ang2, two structurally related members of the angiopoietin family of angiogenic molecules (Maisonpierre et al., 1997; Thurston et al., 2000; Thurston et al., 1999). Vascular permeability was measured by the Evans Blue assay as described above. Both of the 11 week-old transgenic strains that were subjected to Evans Blue analysis had a significant increase, between 2- and 3-fold increase, in vascular permeability at basal levels (FIG. 12C) when compared to liter matched wild-type strains. However, the vascular permeability differences between the transgenic mice and the liter matched wild-type mice was less significant when the mice were challenged with mustard oil prior to subjection to Evans Blue assay analysis. Accordingly, the increase in vascular permeability in transgenic mice relative to their wild-type litter controls may suggest a role for Angptl3 in the regulation of vascular permeability.

DEPOSIT OF MATERIAL

As noted before, the following materials have been deposited with the American Type Culture Collection, 12301 Parklawn Drive, Rockville, Md., USA (ATCC):

| Material | ATCC Dep. No. | Deposit Date |
| --- | --- | --- |
| Angptl3-DNA16451-1078 | 209281 | Aug. 18, 1997 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of the deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and Commissioner's rules pursuant thereto (including 37 C.F.R. §1.14 with particular reference to 886 OG 683).

The assignee of the present application has agreed that if a culture of the materials on deposit should die to be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The present specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of the invention. The deposit of material herein does not constitute an admission that the written description is inadequate to enable the practice of any aspect of the invention, including the best more thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A method of treating inflammatory disease in a liver, comprising administering to said liver an antibody or fragment thereof that binds Angptl3 and inhibits interaction of Angptl3 with αvβ3 integrin, thereby inhibiting the inflammatory disease in the liver.

2. The method of claim 1, wherein Angptl3 comprises an amino acid sequence of SEQ ID NO: 2.

3. The method of claim 2, wherein the liver is human.

4. The method of claim 1, wherein the inflammatory liver disease is liver cirrhosis, liver fibrosis, or toxic metabolic liver damage.

5. The method of claim 1, wherein the antibody is a monoclonal antibody.

6. The method of claim 1, wherein the antibody fragment is a Fab, Fab', F(ab')$_2$, or Fv fragment.

7. The method of claim 1, wherein the antibody is a single-chain antibody.

8. The method of claim 5, wherein the monoclonal antibody is a chimeric antibody.

9. The method of claim 1, wherein the antibody is a humanized antibody.

10. The method of claim 1, wherein the antibody is a human antibody.

11. A method for treating inflammatory liver disease in a mammalian subject, comprising administering to said mammalian subject an antibody or fragment thereof that binds to Angptl3 and inhibits interaction of Angptl3 with αvβ3 integrin, thereby treating the inflammatory liver disease.

12. The method of claim 11, wherein the mammalian subject is human.

13. The method of claim 11, wherein Angptl3 comprises an amino acid sequence of SEQ ID NO: 2.

14. The method of claim 11, wherein the inflammatory liver disease is liver cirrhosis, liver fibrosis, or toxic metabolic liver damage.

15. The method of claim 11, wherein the antibody is a single-chain antibody.

16. The method of claim 11, wherein the antibody is a monoclonal antibody.

17. The method of claim 11, wherein the antibody fragment is a Fab, Fab', F(ab')$_2$, or Fv fragment.

* * * * *

SEQUENCE LISTING

```
<160> NUMBER OF SEQ ID NOS: 36

<210> SEQ ID NO 1
<211> LENGTH: 2042
<212> TYPE: DNA
<213> ORGANISM: Homo sapiens

<400> SEQUENCE: 1
gcggacgcgt gggtgaaatt gaaaatcaag ataaaaatgt tcacaattaa gctccttctt      60
tttattgttc ctctagttat ttcctccaga attgatcaag acaattcatc atttgattct     120
ctatctccag agccaaaatc aagatttgct atgttagacg atgtaaaaat tttagccaat     180
ggcctccttc agttgggaca tggtcttaaa gactttgtcc ataagacgaa gggccaaatt     240
aatgacatat ttcaaaaact caacatattt gatcagtctt tttatgatct atcgctgcaa     300
accagtgaaa tcaaagaaga agaaaaggaa ctgagaagaa ctacatataa actacaagtc     360
aaaaatgaag aggtaaagaa tatgtcactt gaactcaact caaaacttga aagcctccta     420
gaagaaaaaa ttctacttca acaaaaagtg aaatatttag aagagcaact aactaactta     480
```

-continued

```
attcaaaatc aacctgaaac tccagaacac ccagaagtaa cttcacttaa aacttttgta      540
gaaaaacaag ataatagcat caaagacctt ctccagaccg tggaagacca atataaacaa      600
ttaaaccaac agcatagtca ataaaaagaa atagaaaatc agctcagaag gactagtatt      660
caagaaccca cagaaatttc tctatcttcc aagccaagag caccaagaac tactcccttt      720
cttcagttga atgaaataag aaatgtaaaa catgatggca ttcctgctga atgtaccacc      780
atttataaca gaggtgaaca tacaagtggc atgtatgcca tcagacccag caactctcaa      840 gttttttcatg tctactgtga tgttatatca ggtagtccat ggacattaat tcaacatcga      900
atagatggat cacaaaactt caatgaaacg tgggagaact acaaatatgg ttttgggagg      960
cttgatggag aattttggtt gggcctagag aagatatact ccatagtgaa gcaatctaat     1020
tatgttttac gaattgagtt ggaagactgg aaagacaaca acattatat tgaatattct     1080 ttttacttgg gaaatcacga accaactat acgctacatc tagttgcgat tactggcaat     1140
gtccccaatg caatcccgga aaacaaagat ttggtgtttt ctacttggga tcacaaagca     1200
aaaggacact tcaactgtcc agagggttat tcaggaggct ggtggtggca tgatgagtgt     1260
ggagaaaaca acctaaatgg taaatataac aaaccaagag caaaatctaa gccagagagg     1320
agaagaggat tatcttggaa gtctcaaaat ggaaggttat actctataaa atcaaccaaa     1380
atgttgatcc atccaacaga ttcagaaagc tttgaatgaa ctgaggcaat ttaaaggcat     1440
atttaaccat taactcattc caagttaatg tggtctaata atctggtata aatccttaag     1500
agaaagcttg agaaatagat ttttttttatc ttaaagtcac tgtctatta agattaaaca     1560 tacaatcaca taaccttaaa gaataccgtt tacatttctc aatcaaaatt cttataatac     1620
tatttgtttt aaattttgtg atgtgggaat caattttaga tggtcacaat ctagattata     1680
atcaataggt gaacttatta ataactttt ctaaataaaa aatttagaga cttttatttt     1740
aaaaggcatc atatgagcta atatcacaac tttcccagtt taaaaaacta gtactcttgt     1800
taaaactcta aacttgacta aatacagagg actggtaatt gtacagttct taaatgttgt     1860
agtattaatt tcaaaactaa aaatcgtcag cacagagtat gtgtaaaaat ctgtaataca     1920 aattttttaaa ctgatgcttc attttgctac aaaataattt ggagtaaatg tttgatatga     1980
tttatttatg aaacctaatg aagcagaatt aaatactgta ttaaaataag ttcgctgtct     2040
tt                                                                    2042
```

<210> SEQ ID NO 2
<211> LENGTH: 460
<212> TYPE: PRT
<213> ORGANISM: Homo sapiens

<400> SEQUENCE: 2

```
Met Phe Thr Ile Lys Leu Leu Phe Ile Val Pro Leu Val Ile Ser
 1               5                  10                  15

Ser Arg Ile Asp Gln Asp Asn Ser Phe Asp Ser Leu Ser Pro Glu
                20                  25                  30

Pro Lys Ser Arg Phe Ala Met Leu Asp Asp Val Lys Ile Leu Ala Asn
                35                  40                  45

Gly Leu Leu Gln Leu Gly His Gly Leu Lys Asp Phe Val His Lys Thr
         50                  55                  60

Lys Gly Gln Ile Asn Asp Ile Phe Gln Lys Leu Asn Ile Phe Asp Gln
 65                  70                  75                  80

Ser Phe Tyr Asp Leu Ser Leu Gln Thr Ser Glu Ile Lys Glu Glu Glu
                85                  90                  95
```

-continued

```
Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
        130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
        210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
        290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
        370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
450                 455                 460
```

<210> SEQ ID NO 3
<211> LENGTH: 20
<212> TYPE: DNA
<213> ORGANISM: Homo sapiens

<400> SEQUENCE: 3
ccacgttggc ttgaaattga                                    20

```
<210> SEQ ID NO 4
<211> LENGTH: 50
<212> TYPE: DNA
<213> ORGANISM: Homo sapiens

<400> SEQUENCE: 4
cctccagaat tgatcaagac aattcatgat ttgattctct atctccagag            50

<210> SEQ ID NO 5
<211> LENGTH: 19
<212> TYPE: DNA
<213> ORGANISM: Homo sapiens

<400> SEQUENCE: 5
tcgtctaaca tagcaaatc                                             19

<210> SEQ ID NO 6
<211> LENGTH: 27
<212> TYPE: DNA
<213> ORGANISM: Bacteriophage

<400> SEQUENCE: 6
ggattctaat acgactcact atagggc                                    27

<210> SEQ ID NO 7
<211> LENGTH: 21
<212> TYPE: DNA
<213> ORGANISM: Homo sapiens

<400> SEQUENCE: 7
ggcattcctg ctgaatgtac c                                          21

<210> SEQ ID NO 8
<211> LENGTH: 27
<212> TYPE: DNA
<213> ORGANISM: Bacteriophage

<400> SEQUENCE: 8
ctatgaaatt aaccctcact aaaggga                                    27

<210> SEQ ID NO 9
<211> LENGTH: 21
<212> TYPE: DNA
<213> ORGANISM: Homo sapiens

<400> SEQUENCE: 9
accacactca tcatgccacc a                                          21

<210> SEQ ID NO 10
<211> LENGTH: 16
<212> TYPE: PRT
<213> ORGANISM: Homo sapiens

<400> SEQUENCE: 10

Tyr Ser Met Lys Lys Thr Thr Met Lys Ile Ile Pro Phe Asn Arg Leu
 1               5                  10                  15

<210> SEQ ID NO 11
<211> LENGTH: 20
<212> TYPE: DNA
<213> ORGANISM: Murine

<400> SEQUENCE: 11
```

```
gatgaccttc ctgccgactg                                              20
```

<210> SEQ ID NO 12
<211> LENGTH: 13
<212> TYPE: PRT
<213> ORGANISM: Homo sapiens

<400> SEQUENCE: 12

Gly Val Tyr Tyr Gln Gly Gly Thr Tyr Ser Lys Ala Ser
1               5                   10

<210> SEQ ID NO 13
<211> LENGTH: 19
<212> TYPE: DNA
<213> ORGANISM: Murine

<400> SEQUENCE: 13

```
gtcattccac caccagcca                                               19
```

<210> SEQ ID NO 14
<211> LENGTH: 13
<212> TYPE: PRT
<213> ORGANISM: Homo sapiens

<400> SEQUENCE: 14

Pro Trp Thr Leu Ile Gln His Arg Ile Asp Gly Ser Gln
1               5                   10

<210> SEQ ID NO 15
<211> LENGTH: 19
<212> TYPE: PRT
<213> ORGANISM: Homo sapiens

<400> SEQUENCE: 15

Tyr Ser Ile Lys Ser Thr Lys Met Leu Ile His Pro Thr Asp Ser Glu
1               5                   10                  15

Ser Phe Glu

<210> SEQ ID NO 16
<211> LENGTH: 17
<212> TYPE: PRT
<213> ORGANISM: Homo sapiens

<400> SEQUENCE: 16

Tyr Ser Ile Lys Ser Thr Lys Met Leu Ile His Pro Thr Asp Ser Glu
1               5                   10                  15

Ser

<210> SEQ ID NO 17
<211> LENGTH: 16
<212> TYPE: PRT
<213> ORGANISM: Homo sapiens

<400> SEQUENCE: 17

Gly Lys Tyr Asn Lys Pro Arg Ala Lys Ser Lys Pro Glu Arg Arg Arg
1               5                   10                  15

<210> SEQ ID NO 18
<211> LENGTH: 14
<212> TYPE: PRT
<213> ORGANISM: Homo sapiens

<400> SEQUENCE: 18

-continued

```
Gly Lys Tyr Asn Lys Pro Arg Ala Lys Ser Lys Pro Glu Arg
1               5                   10
```

<210> SEQ ID NO 19
<211> LENGTH: 13
<212> TYPE: PRT
<213> ORGANISM: Homo sapiens

<400> SEQUENCE: 19

```
Gly Lys Tyr Asn Lys Pro Arg Ala Lys Ser Lys Pro Glu
1               5                   10
```

<210> SEQ ID NO 20
<211> LENGTH: 13
<212> TYPE: PRT
<213> ORGANISM: Artificial Sequence
<220> FEATURE:
<223> OTHER INFORMATION: Peptide comprising inverted human sequence.

<400> SEQUENCE: 20

```
Gln Ser Gly Asp Ile Arg His Gln Ile Leu Thr Trp Pro
1               5                   10
```

<210> SEQ ID NO 21
<211> LENGTH: 13
<212> TYPE: PRT
<213> ORGANISM: Artificial Sequence
<220> FEATURE:
<223> OTHER INFORMATION: Peptide comprising scrambled human sequence.

<400> SEQUENCE: 21

```
Pro Gln Trp Ser Thr Gly Leu Asp Ile Ile Gln Arg His
1               5                   10
```

<210> SEQ ID NO 22
<211> LENGTH: 17
<212> TYPE: PRT
<213> ORGANISM: Artificial Sequence
<220> FEATURE:
<223> OTHER INFORMATION: Peptide comprising inverted human sequence.

<400> SEQUENCE: 22

```
Ser Glu Ser Asp Thr Pro His Ile Leu Met Lys Thr Ser Lys Ile Ser
1               5                   10                  15

Tyr
```

<210> SEQ ID NO 23
<211> LENGTH: 17
<212> TYPE: PRT
<213> ORGANISM: Artificial Sequence
<220> FEATURE:
<223> OTHER INFORMATION: Peptide comprising scrambled human sequence.

<400> SEQUENCE: 23

```
Tyr Ser Ser Glu Ile Ser Lys Asp Ser Thr Thr Pro Lys His Met Ile
1               5                   10                  15

Leu
```

<210> SEQ ID NO 24
<211> LENGTH: 14
<212> TYPE: PRT
<213> ORGANISM: Artificial Sequence
<220> FEATURE:
<223> OTHER INFORMATION: Peptide comprising inverted human sequence.

```
<400> SEQUENCE: 24

Arg Glu Pro Lys Ser Lys Ala Arg Pro Lys Asn Tyr Lys Gly
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Peptide comprising scrambled human sequence.

<400> SEQUENCE: 25

Gly Arg Lys Glu Tyr Pro Asn Lys Lys Ser Pro Lys Arg Ala
1               5                   10

<210> SEQ ID NO 26
<211> LENGTH: 13
<212> TYPE: PRT
<213> ORGANISM: Homo sapiens

<400> SEQUENCE: 26

Gly Trp Thr Val Phe Gln Lys Arg Leu Asp Gly Ser Val
1               5                   10

<210> SEQ ID NO 27
<211> LENGTH: 242
<212> TYPE: PRT
<213> ORGANISM: Homo sapiens

<400> SEQUENCE: 27

Lys Asp Cys Gln Asp Ile Ala Asn Lys Gly Ala Lys Gln Ser Gly Leu
1               5                   10                  15

Tyr Phe Ile Lys Pro Leu Lys Ala Asn Gln Gln Phe Leu Val Tyr Cys
                20                  25                  30

Glu Ile Asp Gly Ser Gly Asn Gly Trp Thr Val Phe Gln Lys Arg Leu
            35                  40                  45

Asp Gly Ser Val Asp Phe Lys Lys Asn Trp Ile Gln Tyr Lys Glu Gly
        50                  55                  60

Phe Gly His Leu Ser Pro Thr Gly Thr Thr Glu Phe Trp Leu Gly Asn
65                  70                  75                  80

Glu Lys Ile His Leu Ile Ser Thr Gln Ser Ala Ile Pro Tyr Ala Leu
                85                  90                  95

Arg Val Glu Leu Glu Asp Trp Asn Gly Arg Thr Ser Thr Ala Asp Tyr
            100                 105                 110

Ala Met Phe Lys Val Gly Pro Glu Ala Asp Lys Tyr Arg Leu Thr Tyr
        115                 120                 125

Ala Tyr Phe Ala Gly Gly Asp Ala Gly Asp Ala Phe Asp Gly Phe Asp
    130                 135                 140

Phe Gly Asp Asp Pro Ser Asp Lys Phe Phe Thr Ser His Asn Gly Met
145                 150                 155                 160

Gln Phe Ser Thr Trp Asp Asn Asp Asn Asp Lys Phe Glu Gly Asn Cys
                165                 170                 175

Ala Glu Gln Asp Gly Ser Gly Trp Trp Met Asn Lys Cys His Ala Gly
            180                 185                 190

His Leu Asn Gly Val Tyr Tyr Gln Gly Gly Thr Tyr Ser Lys Ala Ser
        195                 200                 205

Thr Pro Asn Gly Tyr Asp Asn Gly Ile Ile Trp Ala Thr Trp Lys Thr
    210                 215                 220
```

Arg Trp Tyr Ser Met Lys Lys Thr Thr Met Lys Ile Ile Pro Phe Asn
225                 230                 235                 240

Arg Leu

<210> SEQ ID NO 28
<211> LENGTH: 215
<212> TYPE: PRT
<213> ORGANISM: Homo sapiens

<400> SEQUENCE: 28

Ala Glu Cys Thr Thr Ile Tyr Asn Arg Gly Glu His Thr Ser Gly Met
1               5                   10                  15

Tyr Ala Ile Arg Pro Ser Asn Ser Gln Val Phe His Val Tyr Cys Asp
            20                  25                  30

Val Ile Ser Gly Ser Pro Trp Thr Leu Ile Gln His Arg Ile Asp Gly
        35                  40                  45

Ser Gln Asn Phe Asn Glu Thr Trp Glu Asn Tyr Lys Tyr Gly Phe Gly
    50                  55                  60

Arg Leu Asp Gly Glu Phe Trp Leu Gly Leu Glu Lys Ile Tyr Ser Ile
65                  70                  75                  80

Val Lys Gln Ser Asn Tyr Val Leu Arg Ile Glu Leu Glu Asp Trp Lys
                85                  90                  95

Asp Asn Lys His Tyr Ile Glu Tyr Ser Phe Tyr Leu Gly Asn His Glu
            100                 105                 110

Thr Asn Tyr Thr Leu His Leu Val Ala Ile Thr Gly Asn Val Pro Asn
        115                 120                 125

Ala Ile Pro Glu Asn Lys Asp Leu Val Phe Ser Thr Trp Asp His Lys
    130                 135                 140

Ala Lys Gly His Phe Asn Cys Pro Glu Gly Tyr Ser Gly Gly Trp Trp
145                 150                 155                 160

Trp His Asp Glu Cys Gly Glu Asn Asn Leu Asn Gly Lys Tyr Asn Lys
                165                 170                 175

Pro Arg Ala Lys Ser Lys Pro Glu Arg Arg Arg Gly Leu Ser Trp Lys
            180                 185                 190

Ser Gln Asn Gly Arg Leu Tyr Ser Ile Lys Ser Thr Lys Met Leu Ile
        195                 200                 205

His Pro Thr Asp Ser Glu Ser
    210                 215

<210> SEQ ID NO 29
<211> LENGTH: 215
<212> TYPE: PRT
<213> ORGANISM: Homo sapiens

<400> SEQUENCE: 29

Arg Asp Cys Ala Asp Val Tyr Gln Ala Gly Phe Asn Lys Ser Gly Ile
1               5                   10                  15

Tyr Thr Ile Tyr Ile Asn Asn Met Pro Glu Pro Lys Lys Val Phe Cys
            20                  25                  30

Asn Met Asp Val Asn Gly Gly Trp Thr Val Ile Gln His Arg Glu
        35                  40                  45

Asp Gly Ser Leu Asp Phe Gln Arg Gly Trp Lys Glu Tyr Lys Met Gly
    50                  55                  60

Phe Gly Asn Pro Ser Gly Glu Tyr Trp Leu Gly Asn Glu Phe Ile Phe
65                  70                  75                  80

Ala Ile Thr Ser Gln Arg Gln Tyr Met Leu Arg Ile Glu Leu Met Asp

-continued

```
                 85                  90                  95
Trp Glu Gly Asn Arg Ala Tyr Ser Gln Tyr Asp Arg Phe His Ile Gly
            100                 105                 110
Asn Glu Lys Gln Asn Tyr Arg Leu Tyr Leu Lys Gly His Thr Gly Thr
        115                 120                 125
Ala Gly Lys Gln Ser Ser Leu Ile Leu His Gly Ala Asp Phe Ser Thr
    130                 135                 140
Lys Asp Ala Asp Asn Asp Asn Cys Met Cys Lys Cys Ala Leu Met Leu
145                 150                 155                 160
Thr Gly Gly Trp Trp Phe Asp Ala Cys Gly Pro Ser Asn Leu Asn Gly
                165                 170                 175
Met Phe Tyr Thr Ala Gly Gln Asn His Gly Lys Leu Asn Gly Ile Lys
            180                 185                 190
Trp His Tyr Phe Lys Gly Pro Ser Tyr Ser Leu Arg Ser Thr Thr Met
        195                 200                 205
Met Ile Arg Pro Leu Asp Phe
    210                 215
```

<210> SEQ ID NO 30
<211> LENGTH: 215
<212> TYPE: PRT
<213> ORGANISM: Homo sapiens

<400> SEQUENCE: 30

```
Arg Asp Cys Ala Glu Val Phe Lys Ser Gly His Thr Thr Asn Gly Ile
1               5                   10                  15
Tyr Thr Leu Thr Phe Pro Asn Ser Thr Glu Glu Ile Lys Ala Tyr Cys
            20                  25                  30
Asp Met Glu Ala Gly Gly Gly Gly Trp Thr Ile Ile Gln Arg Arg Glu
        35                  40                  45
Asp Gly Ser Val Asp Phe Gln Arg Thr Trp Lys Glu Tyr Lys Val Gly
    50                  55                  60
Phe Gly Asn Pro Ser Gly Glu Tyr Trp Leu Gly Asn Glu Phe Val Ser
65                  70                  75                  80
Gln Leu Thr Asn Gln Gln Arg Tyr Val Leu Lys Ile His Leu Lys Asp
                85                  90                  95
Trp Glu Gly Asn Glu Ala Tyr Ser Leu Tyr Glu His Phe Tyr Leu Ser
            100                 105                 110
Ser Glu Glu Leu Asn Tyr Arg Ile His Leu Lys Gly Leu Thr Gly Thr
        115                 120                 125
Ala Gly Lys Ile Ser Ser Ile Ser Gln Pro Gly Asn Asp Phe Ser Thr
    130                 135                 140
Lys Asp Gly Asp Asn Asp Lys Cys Ile Cys Lys Cys Ser Gln Met Leu
145                 150                 155                 160
Thr Gly Gly Trp Trp Phe Asp Ala Cys Gly Pro Ser Asn Leu Asn Gly
                165                 170                 175
Met Tyr Tyr Pro Gln Arg Gln Asn Thr Asn Lys Phe Asn Gly Ile Lys
            180                 185                 190
Trp Tyr Tyr Trp Lys Gly Ser Gly Tyr Ser Leu Lys Ala Thr Thr Met
        195                 200                 205
Met Ile Arg Pro Ala Asp Phe
    210                 215
```

<210> SEQ ID NO 31
<211> LENGTH: 215

```
<212> TYPE: PRT
<213> ORGANISM: Homo sapiens

<400> SEQUENCE: 31

Gln Asp Cys Ala Glu Ile Gln Arg Ser Gly Ala Ser Ala Ser Gly Val
 1               5                  10                  15

Tyr Thr Ile Gln Val Ser Asn Ala Thr Lys Pro Arg Lys Val Phe Cys
             20                  25                  30

Asp Leu Gln Ser Ser Gly Gly Arg Trp Thr Leu Ile Gln Arg Arg Glu
         35                  40                  45

Asn Gly Thr Val Asn Phe Gln Arg Asn Trp Lys Asp Tyr Lys Gln Gly
     50                  55                  60

Phe Gly Asp Pro Ala Gly Glu His Trp Leu Gly Asn Glu Val His
 65                  70                  75                  80

Gln Leu Thr Arg Arg Ala Ala Tyr Ser Leu Arg Val Glu Leu Gln Asp
                 85                  90                  95

Trp Glu Gly His Glu Ala Tyr Ala Gln Tyr Glu His Phe His Leu Gly
            100                 105                 110

Ser Glu Asn Gln Leu Tyr Arg Leu Ser Val Val Gly Tyr Ser Gly Ser
        115                 120                 125

Ala Gly Arg Gln Ser Ser Leu Val Leu Gln Asn Thr Ser Phe Ser Thr
    130                 135                 140

Leu Asp Ser Asp Asn Asp His Cys Leu Cys Lys Cys Ala Gln Val Met
145                 150                 155                 160

Ser Gly Gly Trp Trp Phe Asp Ala Cys Gly Leu Ser Asn Leu Asn Gly
                165                 170                 175

Val Tyr Tyr His Ala Pro Asp Asn Lys Tyr Lys Met Asp Gly Ile Arg
            180                 185                 190

Trp His Tyr Phe Lys Gly Pro Ser Tyr Ser Leu Arg Ala Ser Arg Met
        195                 200                 205

Met Ile Arg Pro Leu Asp Ile
    210                 215

<210> SEQ ID NO 32
<211> LENGTH: 18
<212> TYPE: DNA
<213> ORGANISM: Murine

<400> SEQUENCE: 32
atatgccttg gcggatgc                                                 18

<210> SEQ ID NO 33
<211> LENGTH: 26
<212> TYPE: DNA
<213> ORGANISM: Murine

<400> SEQUENCE: 33
atggacaaaa tctttaagtc catgac                                        26

<210> SEQ ID NO 34
<211> LENGTH: 28
<212> TYPE: DNA
<213> ORGANISM: Murine

<400> SEQUENCE: 34
ctcccagagc acacagacct gatgtttt                                      28

<210> SEQ ID NO 35
```

```
-continued

<211> LENGTH: 18
<212> TYPE: DNA
<213> ORGANISM: Murine

<400> SEQUENCE: 35
gctggcaata tccctggg                                                   18

<210> SEQ ID NO 36
<211> LENGTH: 21
<212> TYPE: DNA
<213> ORGANISM: Murine

<400> SEQUENCE: 36
agctgtccct ttgctctgtg a                                               21
```